US009278986B2

(12) United States Patent
Lee et al.

(10) Patent No.: US 9,278,986 B2
(45) Date of Patent: Mar. 8, 2016

(54) CARBAZOLE-BASED PHOSPHINE OXIDE COMPOUND, AND ORGANIC ELECTROLUMINESCENT DEVICE INCLUDING THE SAME

(75) Inventors: Jun-Yeob Lee, Seongnam-si (KR); Soon-Ok Jeon, Seoul (KR); Kyoung-Soo Yook, Yongin-si (KR); Oh-Young Kim, Yongin-si (KR)

(73) Assignee: SK CHEMICALS CO., LTD., Seongnam-si, Gyeonggido (KR)

( * ) Notice: Subject to any disclaimer, the term of this patent is extended or adjusted under 35 U.S.C. 154(b) by 1109 days.

(21) Appl. No.: 13/322,187

(22) PCT Filed: Nov. 16, 2009

(86) PCT No.: PCT/KR2009/006717
§ 371 (c)(1),
(2), (4) Date: Nov. 23, 2011

(87) PCT Pub. No.: WO2010/137779
PCT Pub. Date: Dec. 2, 2010

(65) Prior Publication Data
US 2012/0068168 A1    Mar. 22, 2012

(30) Foreign Application Priority Data

May 27, 2009 (KR) ......................... 10-2009-0046425
Oct. 30, 2009 (KR) ......................... 10-2009-0104025

(51) Int. Cl.
*H01L 51/54* (2006.01)
*C07F 9/60* (2006.01)
(Continued)

(52) U.S. Cl.
CPC .............. *C07F 9/5728* (2013.01); *C09K 11/06* (2013.01); *H01L 51/0072* (2013.01);
(Continued)

(58) Field of Classification Search
None
See application file for complete search history.

(56) References Cited

U.S. PATENT DOCUMENTS

2007/0166568 A1 *  7/2007  Boerner ............... 428/690
2008/0241518 A1   10/2008  Satou et al.

FOREIGN PATENT DOCUMENTS

| JP | 2004-204140 A |   | 7/2004 |
| JP | 2007109988 A | * | 4/2007 |
| JP | 2009227604 A | * | 10/2009 |
| KR | 10-2005-0037337 A |   | 4/2005 |

OTHER PUBLICATIONS

Machine English translation of JP 2007-109988 A. Apr. 16, 2015.*
(Continued)

*Primary Examiner* — J. L. Yang
(74) *Attorney, Agent, or Firm* — Lucas & Mercanti, LLP

(57) ABSTRACT

The present invention relates to a carbazole-based phosphine oxide compound, and an organic electroluminescent device including the same. According to the present invention, provided are a compound for an organic electroluminescent device which can improve the thermal stability and efficiency characteristics which are unstable and low, respectively, corresponding to problems of known compounds for organic electroluminescent devices, and particularly, can implement excellent efficiency characteristics in a pure blue phosphorescent device, by using the carbazole-based phosphine oxide compound of the compound for the organic electroluminescent device, and the organic electroluminescent device. According to one aspect of the present invention, the carbazole-based phosphine oxide compound of the compound for the organic electroluminescent device is provided, and the organic electroluminescent device containing the same which can implement thermal stability and high efficiency characteristics is also provided.

13 Claims, 6 Drawing Sheets

(51) Int. Cl.
  *C07F 9/572* (2006.01)
  *C09K 11/06* (2006.01)
  *H01L 51/00* (2006.01)
  *H05B 33/14* (2006.01)
  *H01L 51/50* (2006.01)

(52) U.S. Cl.
  CPC ....... *H05B 33/14* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1044* (2013.01); *C09K 2211/1088* (2013.01); *H01L 51/0081* (2013.01); *H01L 51/0085* (2013.01); *H01L 51/0094* (2013.01); *H01L 51/5016* (2013.01)

(56) References Cited

OTHER PUBLICATIONS

Machine English translation of JP 2009-227604 A. Apr. 16, 2015.*

Cai, et al., 'Electron and hole transport in a wide bandgap organic phosphine oxide for blue electrophosphorescence', Applied Physics Letters, Feb. 2008, vol. 92, pp. 083308-1-083308-3. See abstract, figure 1, chemical compound MPO12.

Hsu, et al., 'Phosphine-Oxide-Containing Bipolar Host Materials for Blue Electrophosphorescent Devices', Chemistry of Materials, Feb. 2009, vol. 21, pp. 1017-1022. See scheme 1, chemical compound PCF.

* cited by examiner

CARBAZOLE-BASED PHOSPHINE OXIDE COMPOUND, AND ORGANIC ELECTROLUMINESCENT DEVICE INCLUDING THE SAME

CROSS-REFERENCE TO RELATED APPLICATIONS

This application is a 371 of PCT/KR2009/006717, filed on Nov. 16, 2009, which claims the benefit of Korean Patent Application Nos. 10-2009-0046425, filed on May 27, 2009, and 10-2009-0104025, filed on Oct. 30, 2009, the contents of each of which are incorporated herein by reference.

TECHNICAL FIELD

The present invention relates to a carbarzole-based phosphine oxide compound, which is capable of improving thermal stability of a conventional organic electroluminescent device and increasing efficiency characteristics of the organic electroluminescent device, in particular, a pure blue phosphorescent device, and to an organic electroluminescent device including the same.

BACKGROUND ART

Organic electroluminescent devices have a simpler structure, various processing advantages, higher luminance, superior viewing angle, quicker response rate, and a lower operating voltage than other flat panel display devices such as liquid crystal displays (LCDs), plasma display panels (PDPs), field emission displays (FEDs), etc., and thus many attempts are being made to use them as a light source of flat panel displays such as wall-mountable TVs and so on or of the backlight units of displays, illuminators, advertisement boards and the like.

Typically, when direct-current voltage is applied to an organic electroluminescent device, holes injected from an anode and electrons injected from a cathode recombine to form electron-hole pairs, namely, excitons, after which the excitons return to a stable ground state and the corresponding energy is transferred to a light-emitting material and is thereby converted into light.

In the effort to increase efficiency and stability of an organic electroluminescent device, an organic electroluminescent device operating at low voltage was reported to be made by forming a tandem thin organic film between two opposite electrodes by C. W. Tang et al. in Eastman Kodak (C. W. Tang, S. A. Vanslyke, Applied Physics Letters, vol. 51, pp. 913, 1987), and thorough research into organic materials for organic electroluminescent devices with multilayered thin-film structures is ongoing. The lifetime of such a tandem organic electroluminescent device is closely related to the stability of the thin film and the material. For example, when the thermal stability of the material is lowered, the material may crystallize at high temperature or the operating temperature, undesirably shortening the lifetime of the device.

A variety of known compounds function as the conventional host materials of organic electroluminescent devices. These include triazine-based compounds, oxadiazole-based compounds, benzimidazole-based compounds, phenyl pyridine-based compounds, and silicon-based compounds. However, such compounds are problematic because superior efficiency characteristics cannot be achieved in the organic electroluminescent devices, and host materials able to exhibit superior characteristics in blue phosphorescent devices are considerably limited. Hence, the development of novel compounds to solve such problems is required.

As a novel host material, a novel phosphine oxide based compound has been reported. With this compound, however, it is difficult to attain high efficiency.

Korean Patent Publication No. 10-2006-0109524 discloses an arylphosphine oxide-based compound, an arylphosphine sulfide-based compound or an arylphosphine selenide-based compound and an organic electroluminescent device using the same, but is problematic because high efficiency cannot be obtained in a pure blue phosphorescent device.

Applied Physics Letter (Appl. Phys. Lett. 92, 083308, 2008) discloses a blue phosphorescent device using a phosphine oxide compound having a fluorene structure, but the quantum efficiency of the device is only about 9%, undesirably resulting in low device efficiency.

Accordingly, the present invention has been made keeping in mind the above problems occurring in the related art and the present invention is intended to develop a novel host material, namely, a phosphine oxide compound having a carbazole structure, and apply it as the host material of an organic electroluminescent device.

DISCLOSURE

Technical Problem

In order to solve problems of thermal instability and low efficiency of conventional organic electroluminescent devices, the present invention adopts a carbazole-based phosphine oxide compound, which exhibits high thermal stability and superior hole transport characteristics and thereby may be applied to a hole transport layer and also may be applied as a host material for any light-emitting layer from red to blue phosphorescence, and furthermore may achieve high efficiency characteristics in a pure blue phosphorescent device, and thus an object of the present invention is to provide a carbazole-based phosphine oxide compound and an organic electroluminescent device including the same.

Technical Solution

Accordingly, the present invention provides a compound for an organic electroluminescent device, represented by Chemical Formula 1 below:

[Chemical Formula 1]

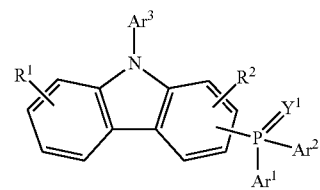

wherein $Y^1$ represents an oxygen atom, a sulfur atom or a selenium atom, $Ar^1$ and $Ar^2$ are identical or different substituents and each represent a substituted or unsubstituted aryl group having 6 to 50 ring carbons, or a substituted or unsubstituted heteroaryl group having 5 to 50 ring atoms, $Ar^3$ represents a substituted or unsubstituted aryl group having 6 to 50 ring carbons, or a substituted or unsubstituted heteroaryl group having 5 to 50 ring atoms, and part or all of $R^1$ and $R^2$ are independently a hydrogen atom, or $R^1$ and $R^2$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or, the substituted or unsubstituted cycloalkyl group having 3 to 50 carbons forms a saturated or unsaturated ring independently or with an adjacent group, wherein the group suitable for substitution on the $Ar^1$ to $Ar^3$, $R^1$ or $R^2$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 2 below:

[Chemical Formula 2]

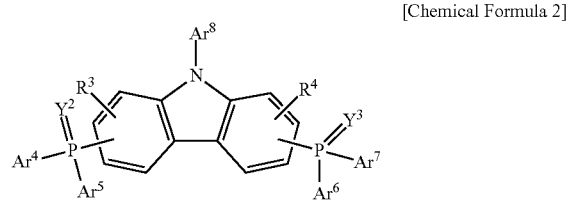

wherein $Y^2$ and $Y^3$ are identical or different substituents and each represent an oxygen atom, a sulfur atom or a selenium atom, $Ar^4$ to $Ar^7$ are identical or different substituents and each represent a substituted or unsubstituted aryl group having 6 to 50 ring carbons, or a substituted or unsubstituted heteroaryl group having 5 to 50 ring atoms, $Ar^8$ represents a substituted or unsubstituted aryl group having 6 to 50 ring carbons, or a substituted or unsubstituted heteroaryl group having 5 to 50 ring atoms, and part or all of $R^3$ and $R^4$ are independently a hydrogen atom, or $R^3$ and $R^4$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^4$ to $Ar^8$, $R^3$ or $R^4$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 3 below:

[Chemical Formula 3]

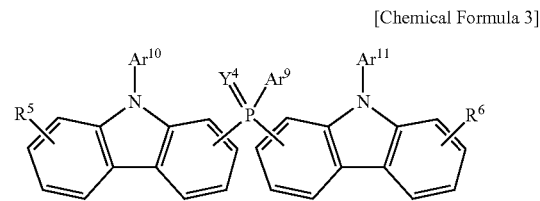

wherein $Y^4$ represents an oxygen atom, a sulfur atom or a selenium atom, $Ar^9$ represents a substituted or unsubstituted aryl group having 6 to 50 ring carbons, or a substituted or unsubstituted heteroaryl group having 5 to 50 ring atoms, $Ar^{10}$ and $Ar^{11}$ are identical or different substituents and each represent a substituted or unsubstituted aryl group having 6 to 50 ring carbons, or a substituted or unsubstituted heteroaryl group having 5 to 50 ring atoms, and part or all of $R^5$ and $R^6$ are independently a hydrogen atom, or $R^5$ and $R^6$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted, aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^9$ to $Ar^{11}$, $R^5$ or $R^6$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 4 below:

[Chemical Formula 4]

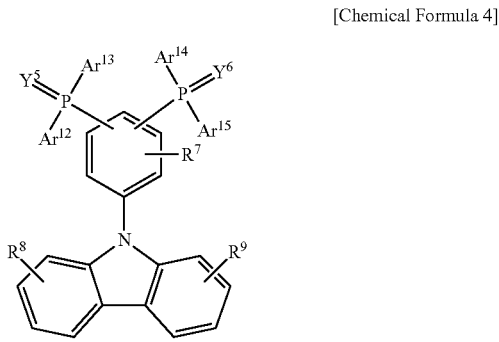

wherein $Y^5$ and $Y^6$ are identical or different substituents and each represent an oxygen atom, a sulfur atom or a selenium atom, $Ar^{12}$ to $Ar^{15}$ are identical or different substituents and each represent a substituted or unsubstituted aryl group having 6 to 50 ring carbons, or a substituted or unsubstituted heteroaryl group having 5 to 50 ring atoms, and part or all of $R^7$ to $R^9$ are independently a hydrogen atom, or $R^7$ to $R^9$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a group suitable for substitution on the $Ar^{12}$ to $Ar^{15}$ and $R^7$ to $R^9$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 5 below:

[Chemical Formula 5]

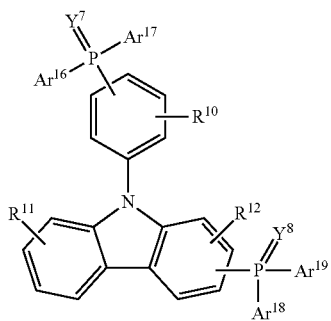

wherein $Y^7$ and $Y^8$ are identical or different substituents and each represent an oxygen atom, a sulfur atom or a selenium'atom, $Ar^{16}$ to $Ar^{19}$ are identical or different substituents and each represent a substituted or unsubstituted aryl group having 6 to 50 ring carbons, or a substituted or unsubstituted heteroaryl group having 5 to 50 ring atoms, and part or all of $R^{10}$ to $R^{12}$ are independently a hydrogen atom, or $R^{10}$ to $R^{12}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a group suitable for substitution on the $Ar^{16}$ to $Ar^{19}$ and $R^{10}$ to $R^{12}$ is a halogen atom, a cyano group, a nitro group, an aryl group having 6 to 50 ring carbons, a heteroaryl group having 5 to ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 6 below:

[Chemical Formula 6]

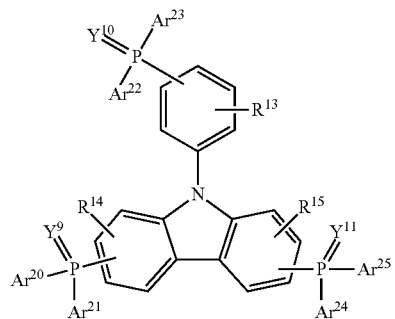

wherein $Y^9$ to $Y^{11}$ are identical or different substituents and each represent an oxygen atom, a sulfur atom or a selenium atom, $Ar^{20}$ to $Ar^{25}$ are identical or different substituents and each represent a substituted or unsubstituted aryl group having 6 to 50 ring carbons, or a substituted or unsubstituted heteroaryl group having 5 to 50 ring atoms, and part or all of $R^{13}$ to $R^{15}$ are independently a hydrogen atom, or $R^{13}$ to $R^{15}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a group suitable for substitution on the $Ar^{20}$ to $Ar^{25}$ and $R^{13}$ to $R^{15}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 7 below:

[Chemical Formula 7]

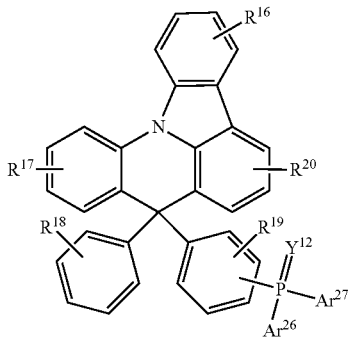

wherein $Y^{12}$ represents an oxygen atom, a sulfur atom or a selenium atom, $Ar^{26}$ and $Ar^{27}$ are identical or different substituents and each represent a substituted or unsubstituted aryl group having 6 to 50 ring carbons, or a substituted or unsubstituted heteroaryl group having 5 to 50 ring atoms, and part or all of $R^{16}$ to $R^{20}$ are independently a hydrogen atom, or $R^{16}$ to $R^{20}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^{26}$, $Ar^{27}$ and $R^{16}$ to $R^{20}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides a compound for an organic electroluminescent device, represented by Chemical Formula 8 below:

[Chemical Formula 8]

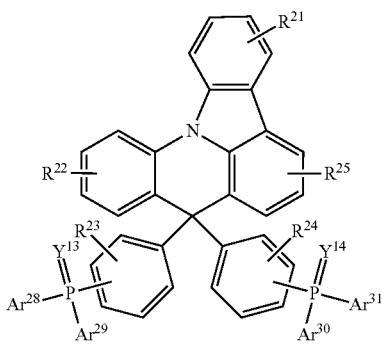

wherein $Y^{13}$ and $Y^{14}$ are identical or different substituents and each represent an oxygen atom, a sulfur atom or a selenium atom, $Ar^{28}$ to $Ar^{31}$ are identical or different substituents and each represent a substituted or unsubstituted aryl group having 6 to 50 ring carbons, or a substituted or unsubstituted heteroaryl group having 5 to 50 ring atoms, and part or all of $R^{21}$ to $R^{25}$ are independently a hydrogen atom, or $R^{21}$ to $R^{25}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having, 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a group suitable for substitution on the $Ar^{28}$ to $Ar^{31}$ and $R^{21}$ to $R^{25}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

In addition, the present invention provides an organic electroluminescent device, comprising:

a first electrode;

a second electrode; and a single organic layer or a plurality of organic layers having at least one light-emitting layer, formed between the first electrode and the second electrode, wherein the organic layer includes the compound for an organic electroluminescent device as above.

As such, the light-emitting layer may include the compound for an organic electroluminescent device according to the present invention. Furthermore, the organic layer may include a hole transport layer including the compound for an organic electroluminescent device according to the present invention.

BEST MODE

Figure 1:
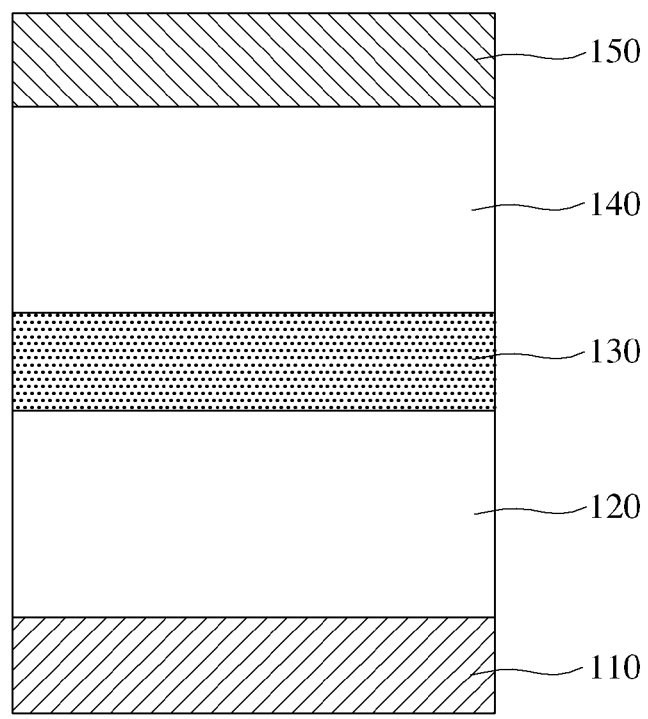
FIG. 1 is a schematic view showing the structure of an organic electroluminescent device according to the present invention.

Hereinafter, a detailed description will be given of a carbazole-based phosphine oxide compound and an organic electroluminescent (EL) device including the same according to preferred embodiments of the present invention with reference to the following chemical formulas or the appended drawings.

In the present invention, with the goal of overcoming the Problems of the low efficiency of conventional organic EL devices, phosphine oxide compounds having a carbazole structure were developed and applied to the host material for a light-emitting layer of an organic EL device.

The carbazole structure has a triplet energy gap of 3.2 eV and may be applied to any light-emitting layer from red phosphorescence to blue phosphorescence, and also has very superior thermal stability and is thus advantageous in terms of stability of the device. Furthermore, the carbazole structure may have very good hole transport characteristics and may thus be utilized as a material for a hole transport layer.

The phosphine oxide structure has superior electron transport characteristics and is advantageous in terms of stability of the device.

Thus, a combination of the carbazole structure and the phosphine oxide structure, which are both units having superior electron and hole transport characteristics and high triplet energy, achieves superior characteristics that are adapted to a host material for a light-emitting layer.

In the present invention, the carbazole-based phosphine oxide compound having the phosphine oxide structure and the carbazole structure was used as a host for a light-emitting layer of an organic EL device. The carbazole structure functions to adjust the triplet energy of an organic material, and the phosphine oxide structure plays a role in improving electron transport characteristics. Hence, the compound according to the present invention is applied to the host of a phosphorescent material by the use of high triplet energy of the carbazole structure, and can be employed as a host material having high charge mobility thanks to the hole transport characteristics of the carbazole structure and the electron transport characteristics of the phosphine oxide structure.

Below is a description of the carbazole-based phosphine oxide according to the present invention and the organic EL device including the same.

The present invention provides a compound for an organic EL device, including a carbazole-based phosphine oxide compound, a carbazole-based phosphine sulfide compound or a carbazole-based phosphine selenide compound (hereinafter which is simply referred to as a carbazole-based phosphine oxide compound), as represented by Chemical Formula 1 below.

[Chemical Formula 1]

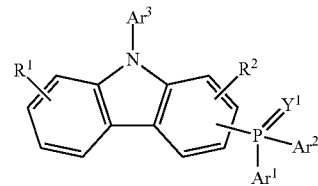

In Chemical Formula 1, $Y^1$ represents an oxygen atom, a sulfur atom or a selenium atom, $Ar^1$ and $Ar^2$ are identical or different substituents and each represent a substituted or unsubstituted aryl group having 6 to 50 ring carbons, or a substituted or unsubstituted heteroaryl group having 5 to 50 ring atoms, $Ar^3$ represents a substituted or unsubstituted aryl group having 6 to 50 ring carbons, or a substituted or unsubstituted heteroaryl group having 5 to 50 ring atoms, and part or all of $R^1$ and $R^2$ are independently a hydrogen atom, or $R^1$ and $R^2$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^1$ to $Ar^3$, $R^1$ or $R^2$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 1, $Y^1$ represents an oxygen atom, $Ar^1$ and $Ar^2$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $Ar^3$ represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^1$ and $R^2$ are independently a hydrogen atom, or $R^1$ and $R^2$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^1$ to $Ar^3$, $R^1$ or $R^2$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

Also, according to the present invention, a compound for an organic EL device may be provided, wherein in Chemical Formual 1, $Y^1$ represents an oxygen atom, $Ar^1$ and $Ar^2$ each represent a phenyl group, $Ar^3$ represents a phenyl group, and $R^1$ and $R^2$ each represent a phenyl group.

In addition, the present invention provides a compound for an organic EL device represented by Chemical Formula 2 below.

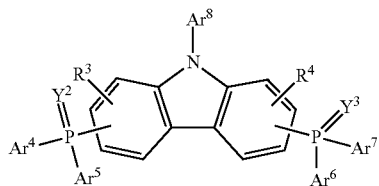

[Chemical Formula 2]

In Chemical Formula 2, $Y^2$ and $Y^3$ are identical or different substituents and each represent an oxygen atom, a sulfur atom or a selenium atom, $Ar^4$ to $Ar^7$ are identical or different substituents and each represent a substituted or unsubstituted aryl group having 6 to 50 ring carbons, or a substituted or unsubstituted heteroaryl group having 5 to 50 ring atoms, $Ar^8$ represents a substituted or unsubstituted aryl group having 6 to 50 ring carbons, or a substituted or unsubstituted heteroaryl group having 5 to 50 ring atoms, and part or all of $R^3$ and $R^4$ are independently a hydrogen atom, or $R^3$ and $R^4$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^4$ to $Ar^8$, $R^3$ or $R^4$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 2, $Y^2$ and $Y^3$ represent an oxygen atom, $Ar^4$ to $Ar^7$ are identical or different substituents and each represent a substituted or unsubstituted phenyl group having 6 to carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $Ar^8$ represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^3$ and $R^4$ are independently a hydrogen atom, or $R^3$ and $R^4$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^4$ to $Ar^8$, $R^3$ or $R^4$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

In addition, the present invention provides a compound for an organic EL device represented by Chemical Formula 3 below.

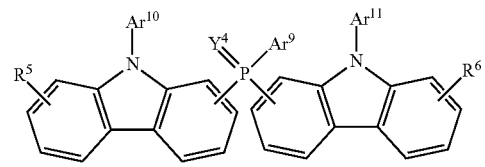

[Chemical Formula 3]

In Chemical Formula 3, $Y^4$ represents an oxygen atom, a sulfur atom or a selenium atom, $Ar^9$ represents a substituted or unsubstituted aryl group having 6 to 50 ring carbons, or a substituted or unsubstituted heteroaryl group having 5 to 50 ring atoms, $Ar^{10}$ and $Ar^{11}$ are identical or different substituents and each represent a substituted or unsubstituted aryl group having 6 to 50 ring carbons, or a substituted or unsubstituted heteroaryl group having 5 to 50 ring atoms, and part or all of $R^5$ and $R^6$ are independently a hydrogen atom, or $R^5$ and $R^6$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^9$ to $Ar^{11}$, $R^5$ or $R^6$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 3, $Y^4$ represents an oxygen atom, $Ar^9$ represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $Ar^{10}$ and $Ar^{11}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^5$ and $R^6$ are independently a hydrogen atom, or $R^5$ and $R^6$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^9$ to $Ar^{11}$, $R^5$ and $R^6$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

In addition, the present invention provides a compound for an organic EL device represented by Chemical Formula 4 below.

[Chemical Formula 4]

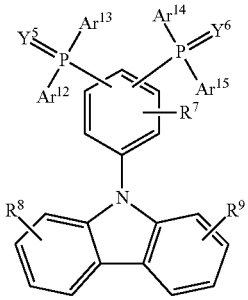

In Chemical Formula 4, $Y^5$ and $Y^6$ are identical or different substituents and each represent an oxygen atom, a sulfur atom or a selenium atom, $Ar^{12}$ to $Ar^{15}$ are identical or different substituents and each represent a substituted or unsubstituted aryl group having 6 to 50 ring carbons, or a substituted or unsubstituted heteroaryl group having 5 to 50 ring atoms, and part or all of $R^7$ to $R^9$ are independently a hydrogen atom, or $R^7$ to $R^9$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^{12}$ to $Ar^{15}$ and $R^7$ to $R^9$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 4, $Y^5$ and $Y^6$ represent an oxygen atom, $Ar^{12}$ to $Ar^{15}$ are identical or different substituents and each represent a substituted or unsubstituted phenyl group having 6 to carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^7$ to $R^9$ are independently a hydrogen atom, or $R^7$ to $R^9$ are identical or different substituents and each represent a halogen atom, a cyano group; a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^{12}$ to $Ar^{15}$ and $R^7$ to $R^9$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

In addition, the present invention provides a compound for an organic EL device represented by Chemical Formula 5 below.

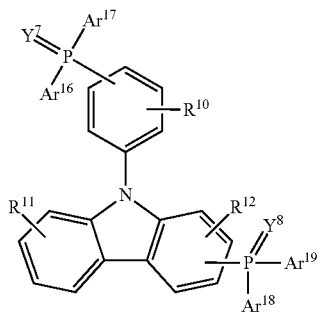

[Chemical Formula 5]

In Chemical Formula 5, $Y^7$ and $Y^8$ are identical or different substituents and each represent an oxygen atom, a sulfur atom or a selenium'atom, $Ar^{18}$ to $Ar^{19}$ are identical or different substituents and each represent a substituted or unsubstituted aryl group having 6 to 50 ring carbons, or a substituted or unsubstituted heteroaryl group having 5 to 50 ring atoms, and part or all of $R^{10}$ to $R^{12}$ are independently a hydrogen atom, or $R^{10}$ to $R^{12}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^{16}$ to $Ar^{19}$ and $R^{10}$ to $R^{12}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 5, $Y^7$ and $Y^8$ each represent an oxygen atom, $Ar^{16}$ to $Ar^{19}$ are identical or different substituents and each represent a substituted or unsubstituted phenyl group having 6 to carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{10}$ to $R^{12}$ are independently a hydrogen atom, or $R^{10}$ to $R^{12}$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^{16}$ to $Ar^{19}$ and $R^{10}$ to $R^{12}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

In addition, the present invention provides a compound for an organic EL device represented by Chemical Formula 6 below.

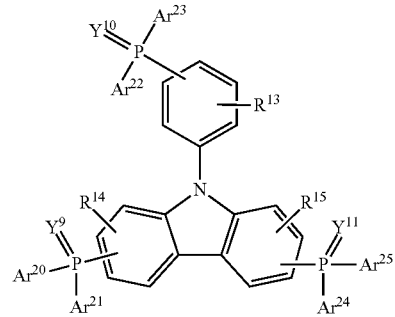

[Chemical Formula 6]

In Chemical Formula 6, $Y^9$ to $Y^{11}$ are identical or different substituents and each represent an oxygen atom, a sulfur atom or a selenium atom, $Ar^{20}$ to $Ar^{25}$ are identical or different substituents and each represent a substituted or unsubstituted aryl group having 6 to 50 ring carbons, or a substituted or unsubstituted heteroaryl group having 5 to 50 ring atoms, and part or all of $R^{13}$ to $R^{15}$ are independently a hydrogen atom, or $R^{13}$ to $R^{15}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^{20}$ to $Ar^{25}$ and $R^{13}$ to $R^{15}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 6, $Y^9$ to $Y^{11}$ each represent an oxygen atom, $Ar^{20}$ to $Ar^{25}$ are identical or different substituents and each represent a substituted or unsubstituted phenyl group having 6 to carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{13}$ to $R^{15}$ are independently a hydrogen atom, or $R^{13}$ to $R^{15}$ are identical, or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^{20}$ to $Ar^{25}$ and $R^{13}$ to $R^{15}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

In addition, the present invention provides a compound for an organic EL device represented by Chemical Formula 7 below.

[Chemical Formula 7]

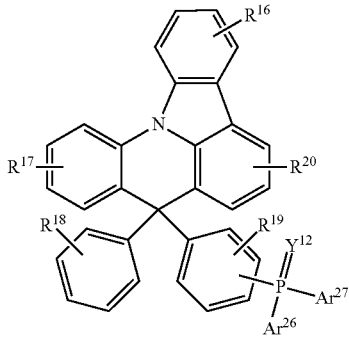

In Chemical Formula 7, $Y^{12}$ represents an oxygen atom, a sulfur atom or a selenium atom, $Ar^{26}$ and $Ar^{27}$ are identical or different substituents and each represent a substituted or unsubstituted aryl group having 6 to 50 ring carbons, or a substituted or unsubstituted heteroaryl group having 5 to 50 ring atoms, and part or all of $R^{16}$ to $R^{20}$ are independently a hydrogen atom, or $R^{16}$ to $R^{20}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^{26}$, $Ar^{27}$ and $R^{16}$ to $R^{20}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 7, $Y^{12}$ represents an oxygen atom, $Ar^{26}$ and $Ar^{27}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{16}$ to $R^{20}$ are independently a hydrogen atom, or $R^{16}$ to $R^{20}$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^{26}$, $Ar^{27}$ and $R^{16}$ to $R^{20}$ is a halogen atom, a cyano group, a nitro group, an aryl group having 6 to 34 carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

In addition, the present invention provides a compound for an organic EL device represented by Chemical Formula 8 below.

[Chemical Formula 8]

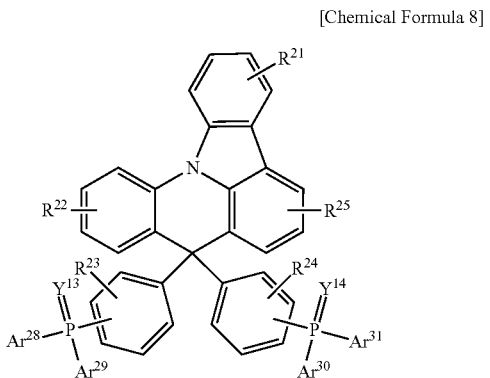

In Chemical Formula 8, $Y^{13}$ and $Y^{14}$ are identical or different substituents and each represent an oxygen atom, a sulfur atom or a selenium atom, $Ar^{28}$ to $Ar^{31}$ are identical or different substituents and each represent a substituted or unsubstituted aryl group having 6 to 50 carbons, or a substituted or unsubstituted heteroaryl group having 5 to 50 ring atoms, and part or all of $R^{21}$ to $R^{25}$ are independently a hydrogen atom, or $R^{21}$ to $R^{25}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein the group suitable for substitution on the $Ar^{28}$ to $Ar^{31}$ and $R^{21}$ to $R^{25}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

According to the present invention, a compound for an organic EL device may be provided, wherein in Chemical Formula 8, $Y^{13}$ and $Y^{14}$ each represent an oxygen atom, $Ar^{28}$ to $Ar^{31}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{21}$ to $R^{25}$ are independently a hydrogen atom, or $R^{21}$ to $R^{25}$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein the group suitable for substitution on the $Ar^{28}$ to $Ar^{31}$ and $R^{21}$ to $R^{25}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

Specific examples of the substituted or unsubstituted aryl group having 6 to 50 ring carbons on the $Ar^1$ to $Ar^{31}$ and $R^1$ to $R^{25}$ include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl -2-yl, m-terphenyl-4-yl, m-terphenyl-3-yl, m-terphenyl -2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4-methylbiphenylyl or 4-tert-butyl-p-terphenyl -4-yl.

Specific examples of the aromatic heterocyclic group having 5 to 50 ring atoms on the $Ar^1$ to $Ar^{31}$ and $R^1$ to $R^{25}$ include 1-pyrolyl, 2-pyrolyl, 3-pyrolyl, pyrazinyl, pyrimidyl, pyridazyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, qunolyl, 3-qunolyl, 4-qunolyl, 5-qunolyl, 6-qunolyl, 7-qunolyl, 8-qunolyl, 1-isoqunolyl, 3-isoqunolyl, 4-isoqunolyl, 5-isoqunolyl, 6-isoqunolyl, 7-isoqunolyl, 8-isoqunolyl, 2-quinoxalinyl, 5-quinoxalinyl, 6-quinoxalinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8- phenanthrolin-7-yl, 2,8-phenanthrolin-9-yl, 2,8-phenanthrolinyl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrol-1-yl, 2-methylpyrol-3-yl, 2-methylpyrol-4-yl, 2-methylpyrol-5-yl, 3-methylpyrol-1-yl, 3-methylpyrol-2-yl, 3-methylpyrol-4-yl, 3-methylpyrol-5-yl, 2-tert-butylpyrol-4-yl, 3-(2-phenylpropyl)pyrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl.

On the $R^1$ to $R^{25}$, specific examples of the substituted or unsubstituted alkyl group having 1 to 50 carbons and the substituted or unsubstituted cycloalkyl group having 3 to 50 carbons include methyl, ethyl, n-propyl, n-pentyl, n-butyl, n-hexyl, n-heptyl, n-octyl, n-decanyl, n-eicosanyl isopropyl, sec-butyl, isobutyl, tert-butyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-tert-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-tert-butyl, 1,2,3-trichloropropyl, bromomethyl, bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-tert-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-tert-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl, 2-norbornyl, etc.

On the $R^1$ to $R^{25}$, specific examples of the substituted or unsubstituted thio group having 1 to 50 carbons include methylthio, ethylthio, propylthio, butylthio, pentylthio, hexylthio, tri(isopropyl)thio, tri(isobutyl)thio, tri(tert-butyl)thio, tri(2-butyl)thio, phenylthio, naphthylthio, biphenylthio, (3-methylphenyl)thio, (4-methylnaphthyl)thio, (2-methylbiphenyl)thio, etc.

On the $R^1$ to $R^{25}$ specific examples of the substituted or unsubstituted silyl group having 1 to 50 carbons include trimethylsilyl, triethylsilyl, tributylsilyl, tri(isopropyl)silyl, tri(isobutyl)silyl, tri(tert-butyl)silyl, tri(2-butyl)silyl, triphenylsilyl, trinaphthylsilyl, tribiphenylsilyl, tri(3-methylphenyl)silyl, tri(4-methylnaphthyl)silyl, tri(2-methylbiphenyl)silyl, phenylmethylsilyl, phenylethylsilyl, naphthylmethylsilyl, naphthylethylsilyl, biphenylmethylsilyl, 3-methyl-phenylmethylsilyl, phenyl(isopropyl)silyl, naphthyl(isopropyl)silyl or biphenyl(isopropyl)silyl.

Below the structural formulas of Compounds 1 to 194 which are examples of the compound for an organic EL device according to the present invention are shown in Tables 1 to 22, but the present invention is not limited to such compounds.

TABLE 1

| Compound | Structural Formula |
|---|---|
| 1 | |
| 2 | |
| 3 | |
| 4 | |

TABLE 1-continued
| Compound | Structural Formula |
|---|---|
| 5 | 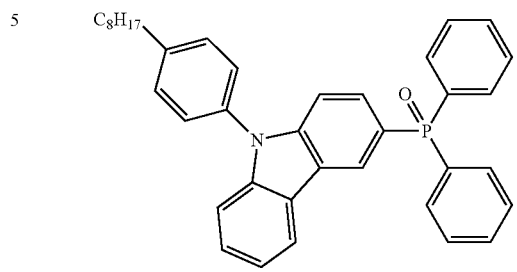 |
| 6 | 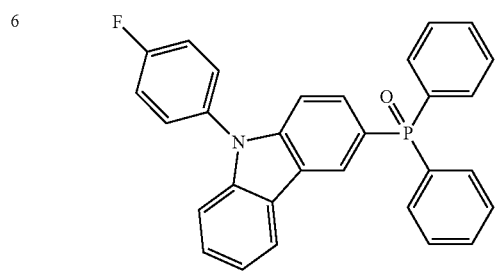 |
| 7 | 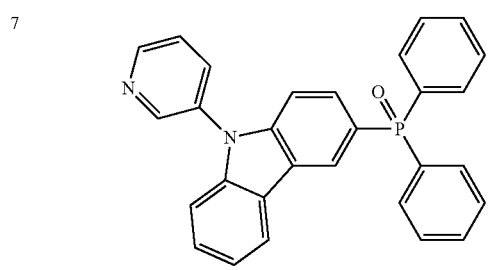 |
| 8 | 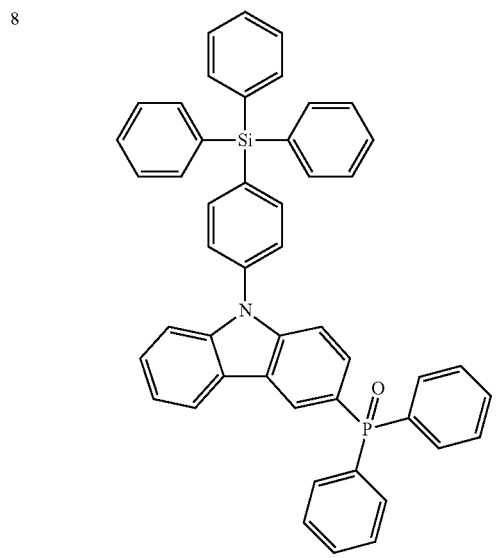 |
| 9 | 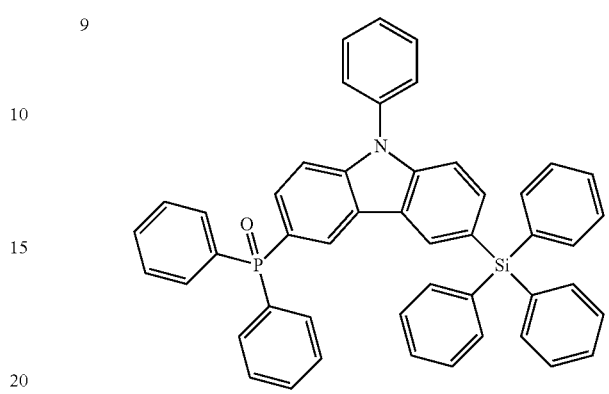 |
| 10 | 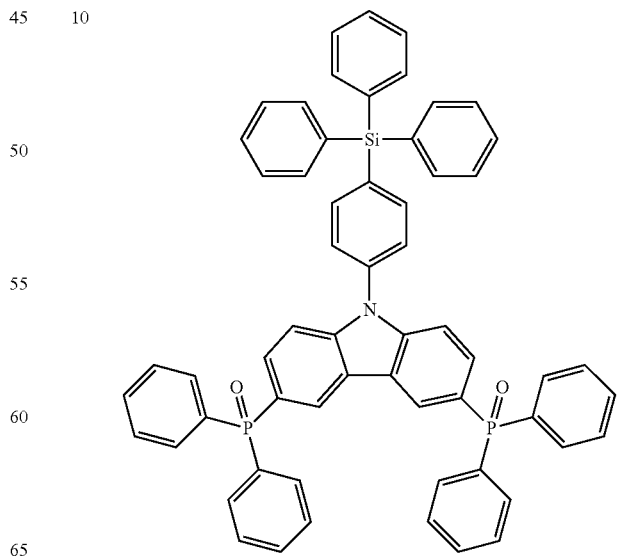 |

TABLE 2
| Compound | Structural Formula |
|---|---|
| 11 | 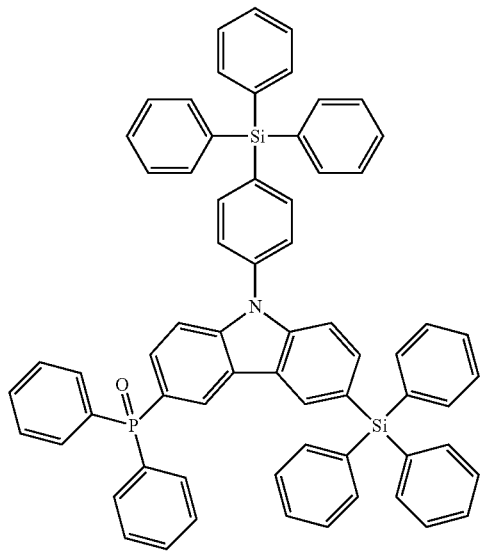 [SMILES: O=P(c1ccccc1)(c1ccccc1)c1ccc2c(c1)c1cc([Si](c3ccccc3)(c3ccccc3)c3ccccc3)ccc1n2-c1ccc([Si](c2ccccc2)(c2ccccc2)c2ccccc2)cc1] |
| 12 | 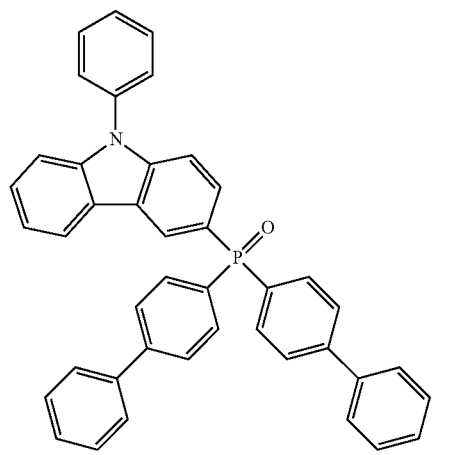 [SMILES: O=P(c1ccc(-c2ccccc2)cc1)(c1ccc(-c2ccccc2)cc1)c1ccc2c(c1)c1ccccc1n2-c1ccccc1] |
| 13 | 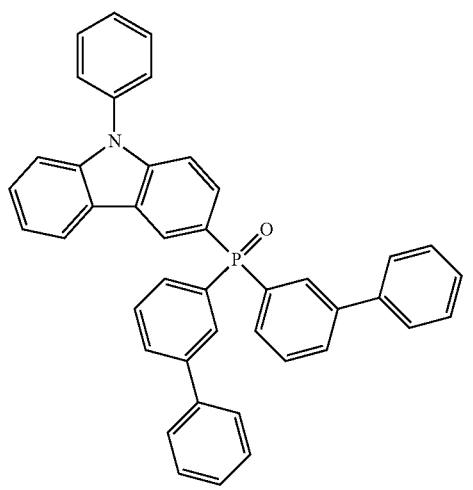 [SMILES: O=P(c1cccc(-c2ccccc2)c1)(c1cccc(-c2ccccc2)c1)c1ccc2c(c1)c1ccccc1n2-c1ccccc1] |
TABLE 2-continued
| Compound | Structural Formula |
|---|---|
| 14 | 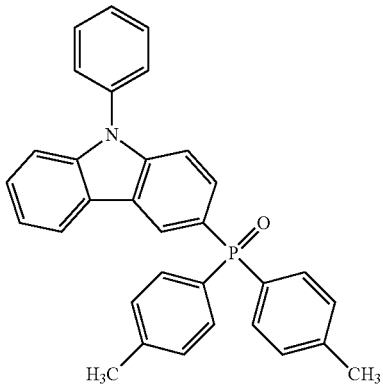 [SMILES: Cc1ccc(P(=O)(c2ccc(C)cc2)c2ccc3c(c2)c2ccccc2n3-c2ccccc2)cc1] |
| 15 | 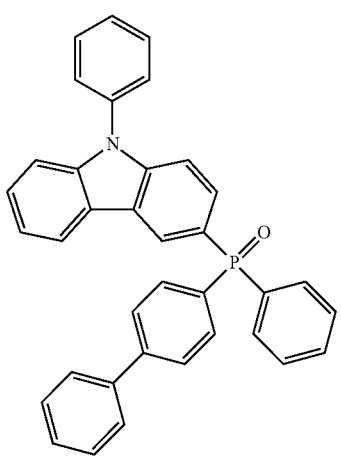 [SMILES: O=P(c1ccccc1)(c1ccc(-c2ccccc2)cc1)c1ccc2c(c1)c1ccccc1n2-c1ccccc1] |
| 16 | 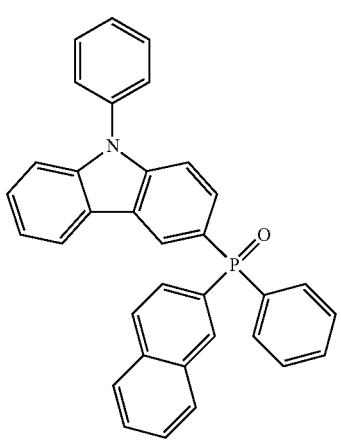 [SMILES: O=P(c1ccccc1)(c1ccc2ccccc2c1)c1ccc2c(c1)c1ccccc1n2-c1ccccc1] |

TABLE 2-continued

| Compound | Structural Formula |
|---|---|
| 17 | |
| 18 | |

TABLE 3

| Compound | Structural Formula |
|---|---|
| 19 | |
| 20 | |

TABLE 3-continued
| Compound | Structural Formula |
| --- | --- |
| 21 | 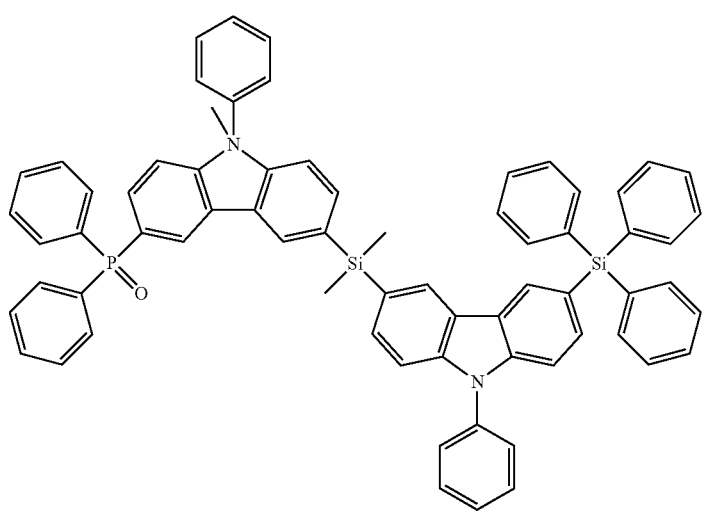 |
| 22 | 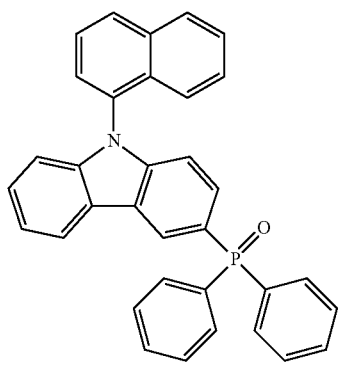 [SMILES: O=P(c1ccccc1)(c1ccccc1)c1ccc2c(c1)c1ccccc1n2-c1cccc2ccccc12] |
| 23 | 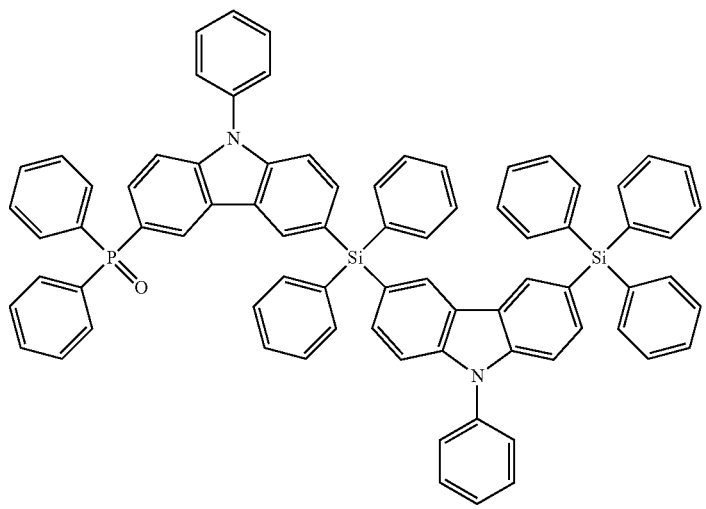 [SMILES: O=P(c1ccccc1)(c1ccccc1)c1ccc2c(c1)c1cc([Si](c3ccccc3)(c3ccccc3)c3ccc4c(c3)c3cc([Si](c5ccccc5)(c5ccccc5)c5ccccc5)ccc3n4-c3ccccc3)ccc1n2-c1ccccc1] |

TABLE 3-continued
| Compound | Structural Formula |
|---|---|
| 24 | 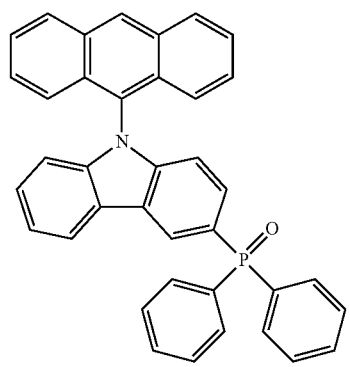 [SMILES: O=P(c1ccccc1)(c1ccccc1)c1ccc2c(c1)c1ccccc1n2-c1c2ccccc2cc2ccccc12] |
| 25 | 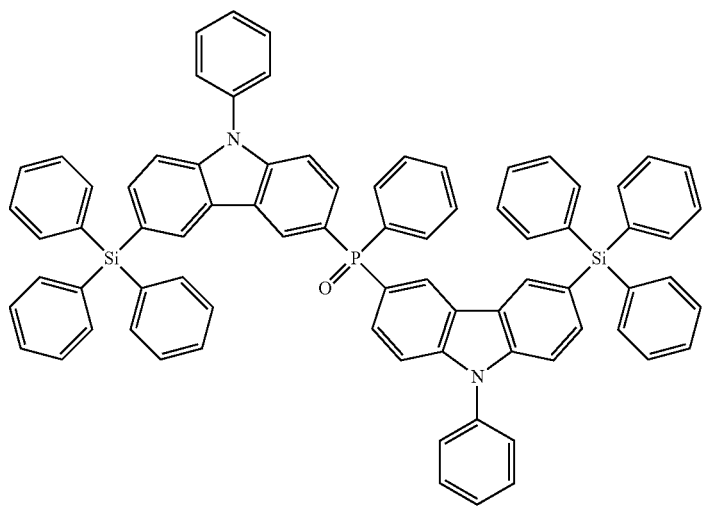 [SMILES: O=P(c1ccccc1)(c1ccc2c(c1)c1cc([Si](c3ccccc3)(c3ccccc3)c3ccccc3)ccc1n2-c1ccccc1)c1ccc2c(c1)c1cc([Si](c3ccccc3)(c3ccccc3)c3ccccc3)ccc1n2-c1ccccc1] |
| 26 | 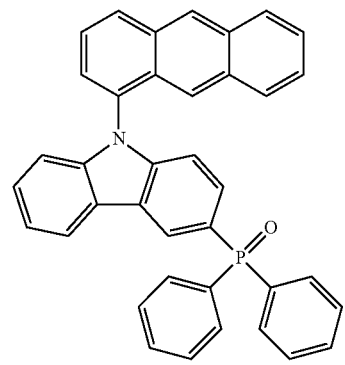 [SMILES: O=P(c1ccccc1)(c1ccccc1)c1ccc2c(c1)c1ccccc1n2-c1cccc2cc3ccccc3cc12] |

TABLE 3-continued
| Compound | Structural Formula |
|---|---|
| 27 | 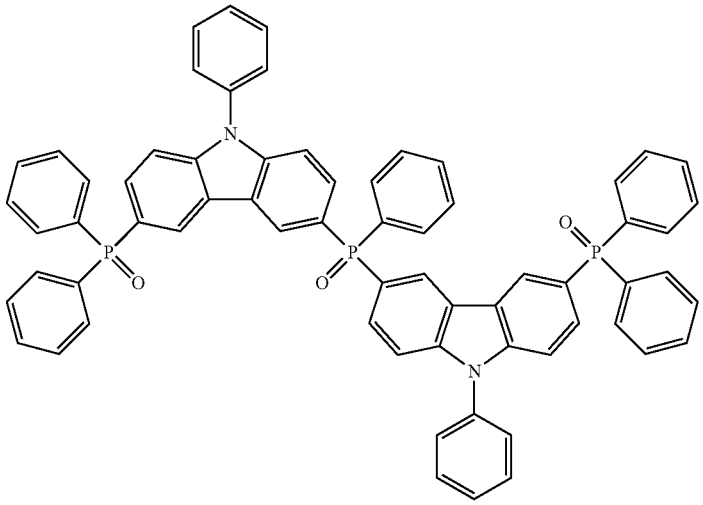 [SMILES: O=P(c1ccccc1)(c1ccccc1)c1ccc2c(c1)c1cc(P(=O)(c3ccccc3)c3ccc4c(c3)c3cc(P(=O)(c5ccccc5)c5ccccc5)ccc3n4-c3ccccc3)ccc1n2-c1ccccc1] |
| 28 | 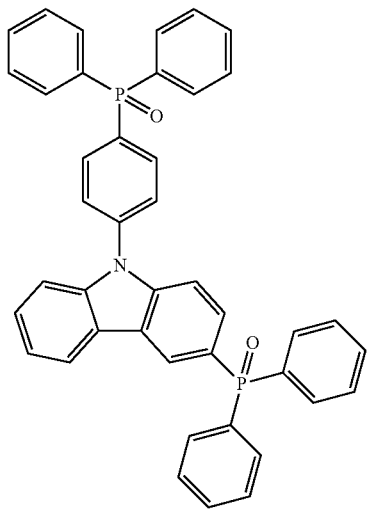 [SMILES: O=P(c1ccccc1)(c1ccccc1)c1ccc(-n2c3ccccc3c3cc(P(=O)(c4ccccc4)c4ccccc4)ccc32)cc1] |

TABLE 4
| Compound | Structural Formula |
| --- | --- |
| 29 | 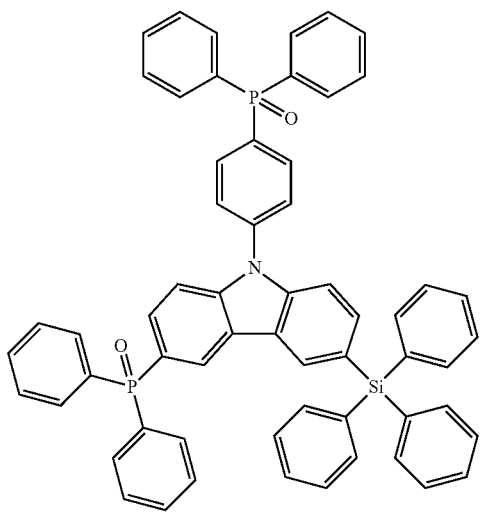 [SMILES: O=P(c1ccccc1)(c1ccccc1)c1ccc(-n2c3ccc([Si](c4ccccc4)(c4ccccc4)c4ccccc4)cc3c3cc(P(=O)(c4ccccc4)c4ccccc4)ccc32)cc1] |
| 30 | 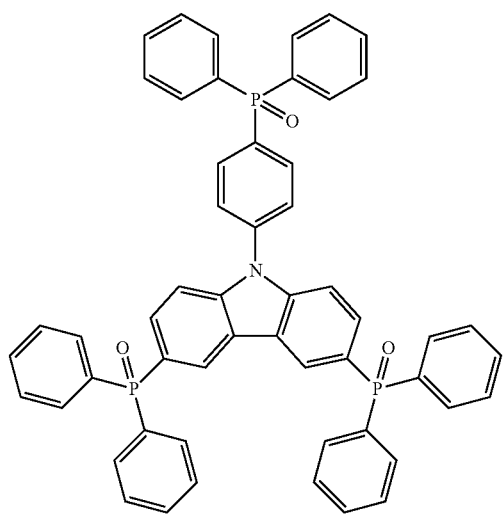 [SMILES: O=P(c1ccccc1)(c1ccccc1)c1ccc(-n2c3ccc(P(=O)(c4ccccc4)c4ccccc4)cc3c3cc(P(=O)(c4ccccc4)c4ccccc4)ccc32)cc1] |
| 31 | 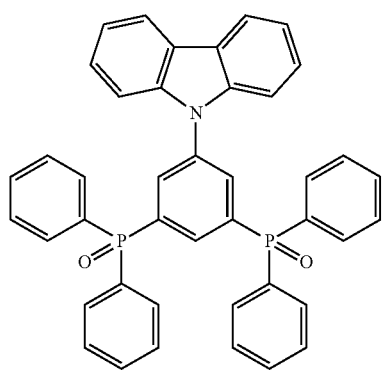 [SMILES: O=P(c1ccccc1)(c1ccccc1)c1cc(-n2c3ccccc3c3ccccc32)cc(P(=O)(c2ccccc2)c2ccccc2)c1] |

TABLE 4-continued
| Compound | Structural Formula |
|---|---|
| 32 | 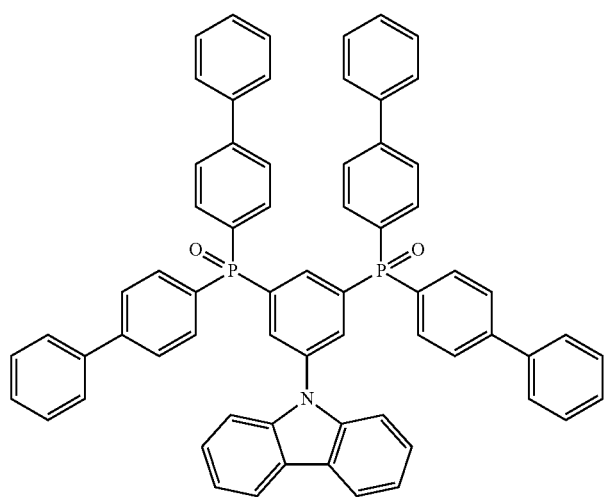 [SMILES: O=P(c1ccc(-c2ccccc2)cc1)(c1ccc(-c2ccccc2)cc1)c1cc(-n2c3ccccc3c3ccccc32)cc(P(=O)(c2ccc(-c3ccccc3)cc2)c2ccc(-c3ccccc3)cc2)c1] |
| 33 | 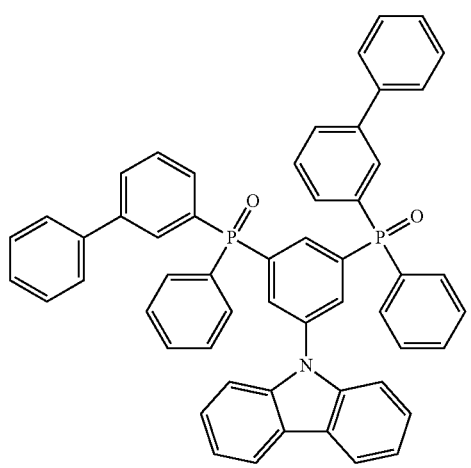 [SMILES: O=P(c1ccccc1)(c1cccc(-c2ccccc2)c1)c1cc(-n2c3ccccc3c3ccccc32)cc(P(=O)(c2ccccc2)c2cccc(-c3ccccc3)c2)c1] |
| 34 | 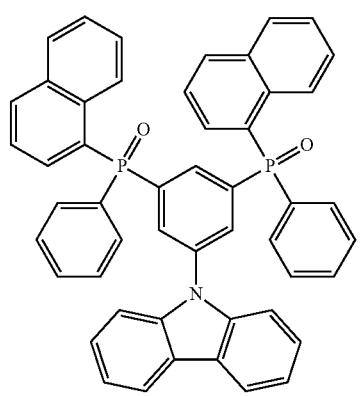 [SMILES: O=P(c1ccccc1)(c1cc(-n2c3ccccc3c3ccccc32)cc(P(=O)(c2ccccc2)c2cccc3ccccc23)c1)c1cccc2ccccc12] |

TABLE 4-continued
| Compound | Structural Formula |
| --- | --- |
| 35 | 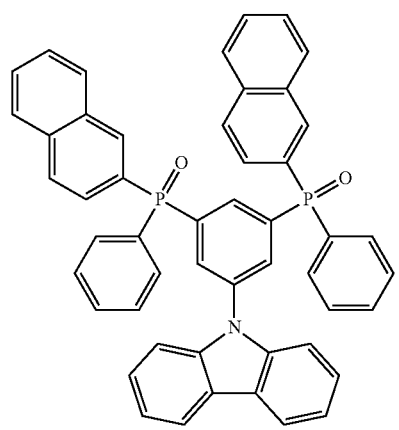 [SMILES: O=P(c1ccccc1)(c1cc(-n2c3ccccc3c3ccccc32)cc(P(=O)(c2ccccc2)c2ccc3ccccc3c2)c1)c1ccc2ccccc2c1] |
| 36 | |
| 37 | |

TABLE 4-continued
| Compound | Structural Formula |
|---|---|
| 38 | |
TABLE 5
| Compound | Structural Formula |
|---|---|
| 39 | |
| 40 | 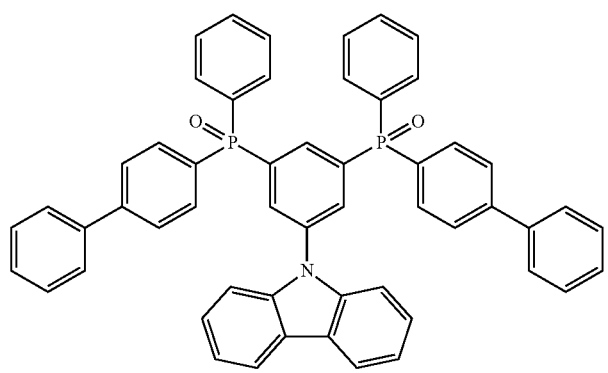 [SMILES: O=P(c1ccccc1)(c1ccc(-c2ccccc2)cc1)c1cc(-n2c3ccccc3c3ccccc32)cc(P(=O)(c2ccccc2)c2ccc(-c3ccccc3)cc2)c1] |

TABLE 5-continued
| Compound | Structural Formula |
|---|---|
| 41 | 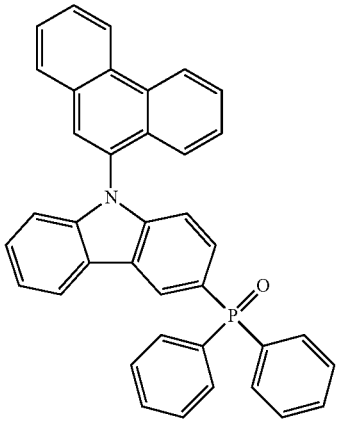 [SMILES: O=P(c1ccccc1)(c1ccccc1)c1ccc2c(c1)c1ccccc1n2-c1cc2ccccc2c2ccccc12] |
| 42 | 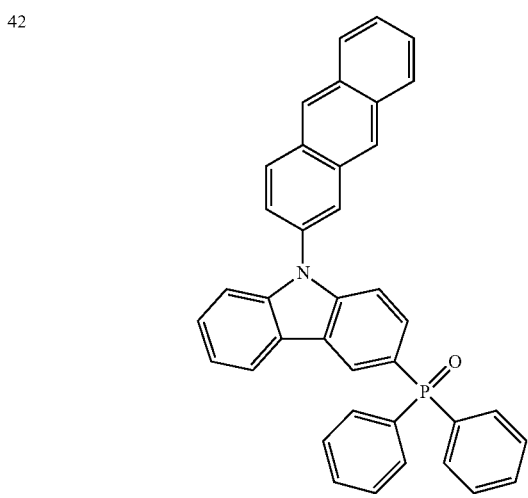 |
| 43 | 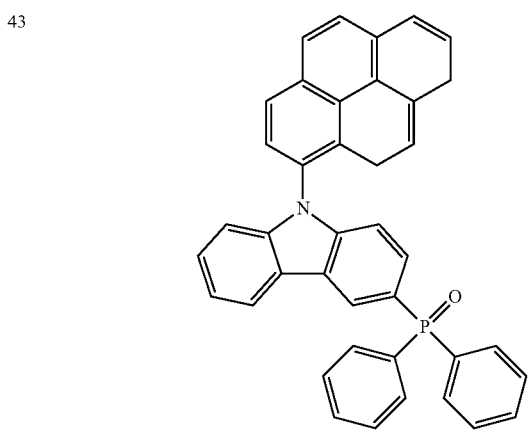 |

TABLE 5-continued
| Compound | Structural Formula |
|---|---|
| 44 | 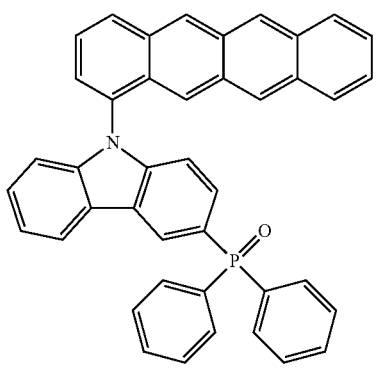 [SMILES: O=P(c1ccccc1)(c1ccccc1)c1ccc2c(c1)c1ccccc1n2-c1cccc2cc3cc4ccccc4cc3cc12] |
| 45 | 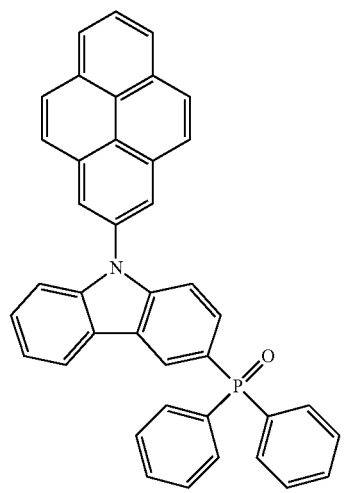 [SMILES: O=P(c1ccccc1)(c1ccccc1)c1ccc2c(c1)c1ccccc1n2-c1cc2ccc3cccc4ccc(c1)c2c34] |
| 46 | 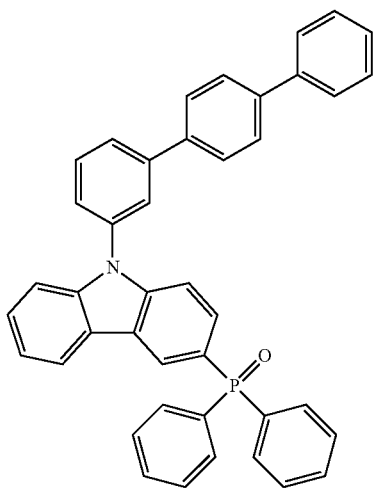 [SMILES: O=P(c1ccccc1)(c1ccccc1)c1ccc2c(c1)c1ccccc1n2-c1cccc(-c2ccc(-c3ccccc3)cc2)c1] |

TABLE 5-continued

| Compound | Structural Formula |
|---|---|
| 47 | (structure: carbazole N-substituted with meta-terphenyl group; 3-position bears diphenylphosphine oxide) |
| 48 | (structure: carbazole N-substituted with 4'-tert-butyl-biphenyl-3-yl group; 3-position bears diphenylphosphine oxide) |

TABLE 6

| Compound | Structural Formula |
|---|---|
| 49 | (structure: carbazole N-substituted with a biphenyl-phenyl group (ortho-linked terphenyl); 3-position bears diphenylphosphine oxide) |
| 50 | (structure: carbazole N-substituted with 4'-methyl-biphenyl-3-yl group; 3-position bears diphenylphosphine oxide) |

TABLE 6-continued
| Compound | Structural Formula |
| --- | --- |
| 51 | 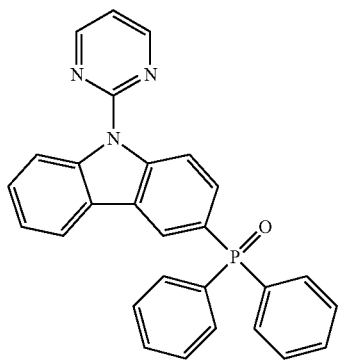 |
| 52 | 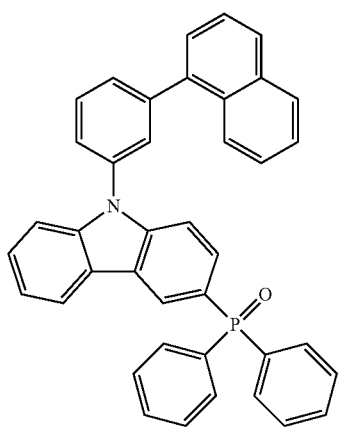 [SMILES: O=P(c1ccccc1)(c1ccccc1)c1ccc2c(c1)c1ccccc1n2-c1cccc(-c2cccc3ccccc23)c1] |
| 53 | 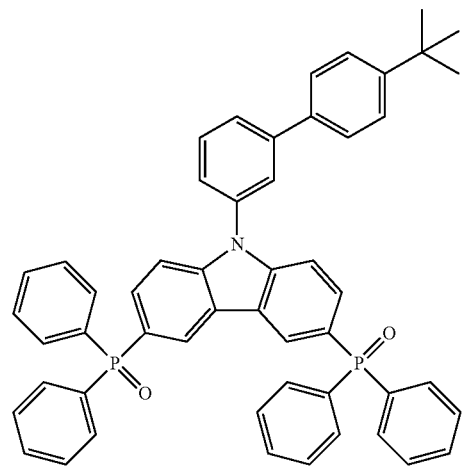 [SMILES: CC(C)(C)c1ccc(-c2cccc(-n3c4ccc(P(=O)(c5ccccc5)c5ccccc5)cc4c4cc(P(=O)(c5ccccc5)c5ccccc5)ccc43)c2)cc1] |
| 54 | 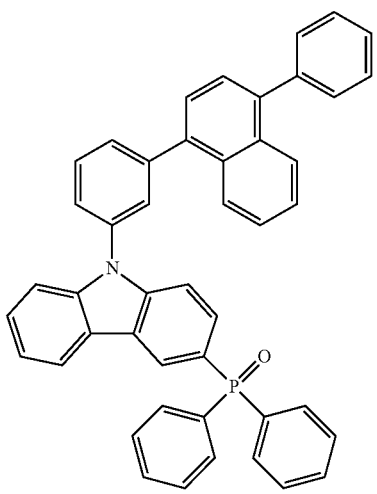 [SMILES: O=P(c1ccccc1)(c1ccccc1)c1ccc2c(c1)c1ccccc1n2-c1cccc(-c2ccc(-c3ccccc3)c3ccccc23)c1] |
| 55 | 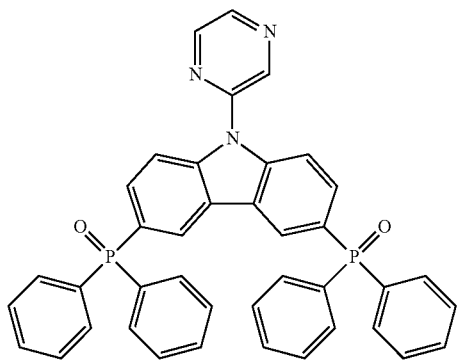 [SMILES: O=P(c1ccccc1)(c1ccccc1)c1ccc2c(c1)c1cc(P(=O)(c3ccccc3)c3ccccc3)ccc1n2-c1cnccn1] |
| 56 | 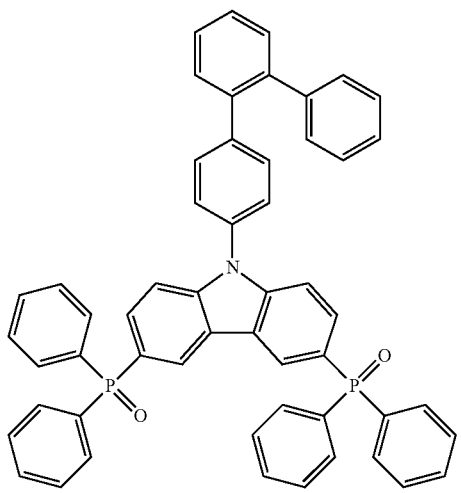 [SMILES: O=P(c1ccccc1)(c1ccccc1)c1ccc2c(c1)c1cc(P(=O)(c3ccccc3)c3ccccc3)ccc1n2-c1ccc(-c2ccccc2-c2ccccc2)cc1] |

TABLE 6-continued
| Compound | Structural Formula |
|---|---|
| 57 | 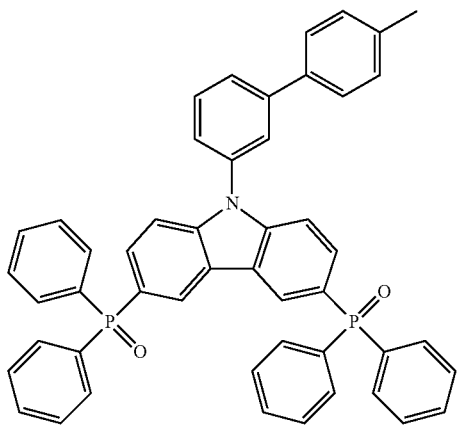 [SMILES: Cc1ccc(-c2cccc(-n3c4ccc(P(=O)(c5ccccc5)c5ccccc5)cc4c4cc(P(=O)(c5ccccc5)c5ccccc5)ccc43)c2)cc1] |
| 58 | 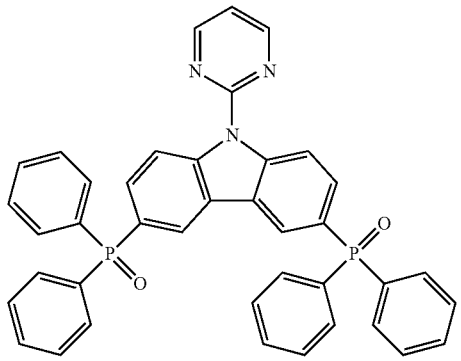 [SMILES: O=P(c1ccccc1)(c1ccccc1)c1ccc2c(c1)c1cc(P(=O)(c3ccccc3)c3ccccc3)ccc1n2-c1ncccn1] |
TABLE 7
| Compound | Structural Formula |
|---|---|
| 59 | 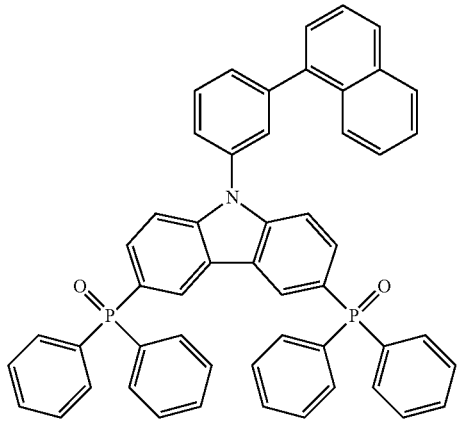 [SMILES: O=P(c1ccccc1)(c1ccccc1)c1ccc2c(c1)c1cc(P(=O)(c3ccccc3)c3ccccc3)ccc1n2-c1cccc(-c2cccc3ccccc23)c1] |
TABLE 7-continued
| Compound | Structural Formula |
|---|---|
| 60 | 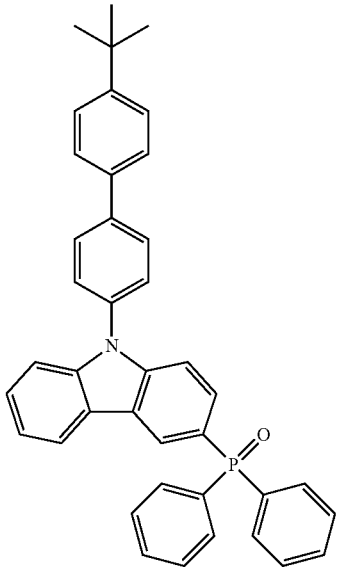 [SMILES: CC(C)(C)c1ccc(-c2ccc(-n3c4ccccc4c4cc(P(=O)(c5ccccc5)c5ccccc5)ccc43)cc2)cc1] |
| 61 | 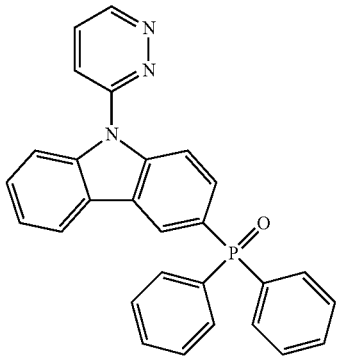 [SMILES: O=P(c1ccccc1)(c1ccccc1)c1ccc2c(c1)c1ccccc1n2-c1cccnn1] |
| 62 | 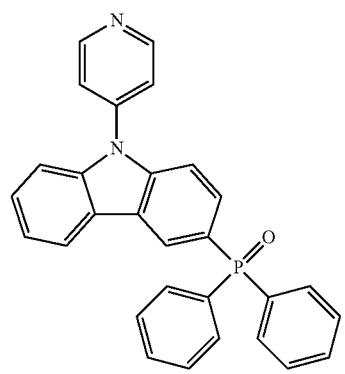 [SMILES: O=P(c1ccccc1)(c1ccccc1)c1ccc2c(c1)c1ccccc1n2-c1ccncc1] |

TABLE 7-continued

| Compound | Structural Formula |
|---|---|
| 63 | |
| 64 | |
| 65 | |
| 66 | |

TABLE 7-continued

| Compound | Structural Formula |
|---|---|
| 67 | |
| 68 | |

TABLE 8

| Compound | Structural Formula |
|---|---|
| 69 | |
| 70 | |

TABLE 8-continued

| Compound | Structural Formula |
|---|---|
| 71 | |
| 72 | |
| 73 | |
| 74 | |

TABLE 8-continued

| Compound | Structural Formula |
|---|---|
| 75 | |
| 76 | |
| 77 | |

TABLE 8-continued

| Compound | Structural Formula |
|---|---|
| 78 | |

TABLE 9

| Compound | Structural Formula |
|---|---|
| 79 | |
| 80 | |

TABLE 9-continued

| Compound | Structural Formula |
|---|---|
| 81 | |
| 82 | |
| 83 | |
| 84 | |

TABLE 9-continued
| Compound | Structural Formula |
|---|---|
| 85 | 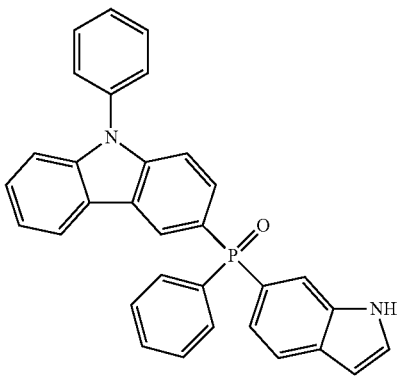 [SMILES: O=P(c1ccccc1)(c1ccc2cc[nH]c2c1)c1ccc2c(c1)c1ccccc1n2-c1ccccc1] |
| 86 | 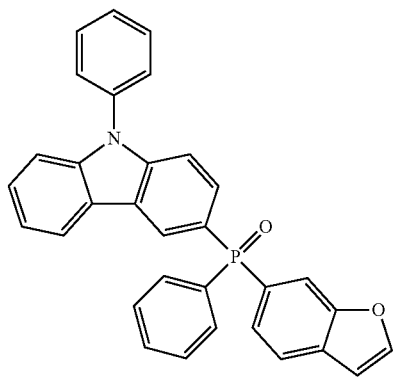 [SMILES: O=P(c1ccccc1)(c1ccc2ccoc2c1)c1ccc2c(c1)c1ccccc1n2-c1ccccc1] |
| 87 | 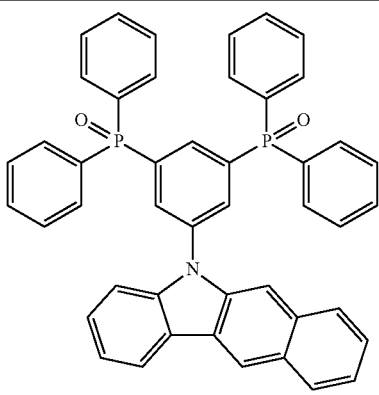 |
| 88 | 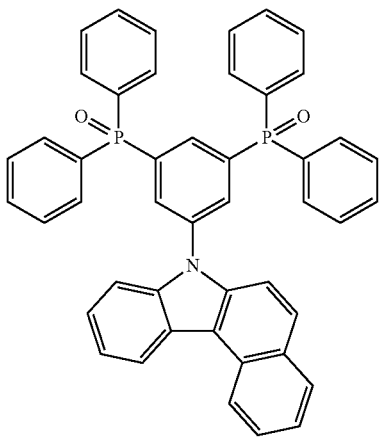 [SMILES: O=P(c1ccccc1)(c1ccccc1)c1cc(-n2c3ccccc3c3c4ccccc4ccc32)cc(P(=O)(c2ccccc2)c2ccccc2)c1] |
TABLE 10
| Compound | Structural Formula |
|---|---|
| 89 | 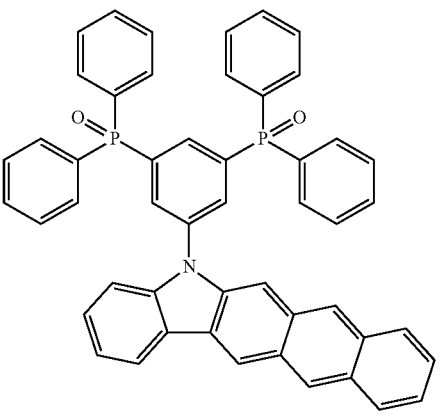 [SMILES: O=P(c1ccccc1)(c1ccccc1)c1cc(-n2c3ccccc3c3cc4cc5ccccc5cc4cc32)cc(P(=O)(c2ccccc2)c2ccccc2)c1] |

TABLE 10-continued

| Compound | Structural Formula |
|---|---|
| 90 | |
| 91 | |
| 92 | |
| 93 | |

TABLE 10-continued

| Compound | Structural Formula |
| --- | --- |
| 94 | |
| 95 | |
| 96 | |
| 97 | |

TABLE 10-continued
| Compound | Structural Formula |
| --- | --- |
| 98 | |
TABLE 11
| Compound | Structural Formula |
| --- | --- |
| 99 | 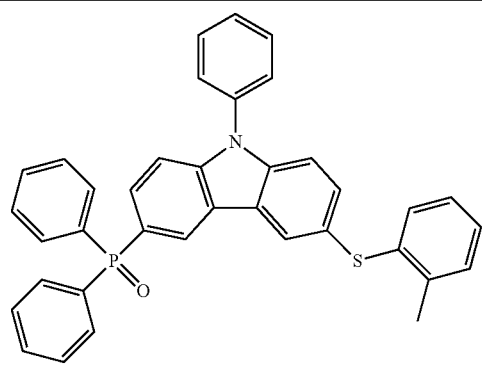 |
| 100 | |
| 101 | 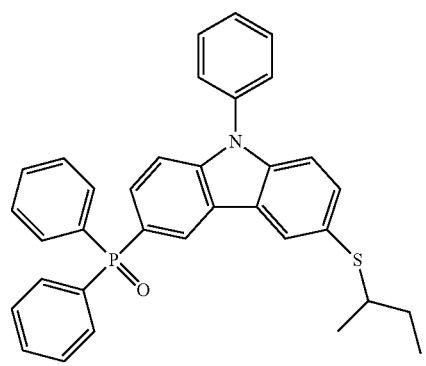 [SMILES: CCC(C)Sc1ccc2c(c1)c1cc(P(=O)(c3ccccc3)c3ccccc3)ccc1n2-c1ccccc1] |
TABLE 11-continued
| Compound | Structural Formula |
| --- | --- |
| 102 | 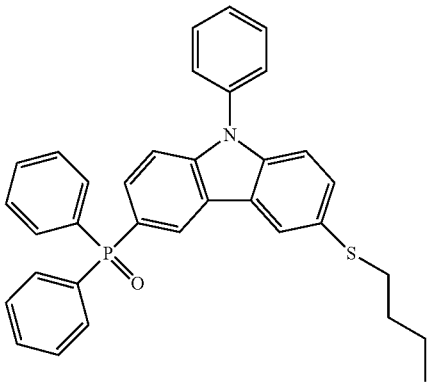 [SMILES: CCCCSc1ccc2c(c1)c1cc(P(=O)(c3ccccc3)c3ccccc3)ccc1n2-c1ccccc1] |
| 103 | 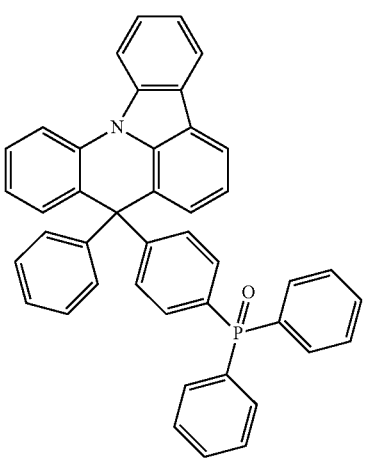 [SMILES: O=P(c1ccccc1)(c1ccccc1)c1ccc(C2(c3ccccc3)c3ccccc3-n3c4ccccc4c4cccc2c43)cc1] |
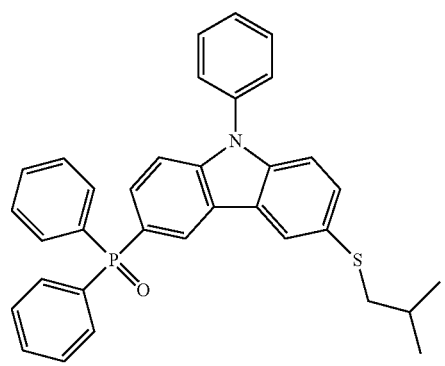

TABLE 11-continued

| Compound | Structural Formula |
|---|---|
| 104 | |
| 105 | |
| 106 | |
| 107 | |
| 108 | |

TABLE 12
| Compound | Structural Formula |
|---|---|
| 109 | 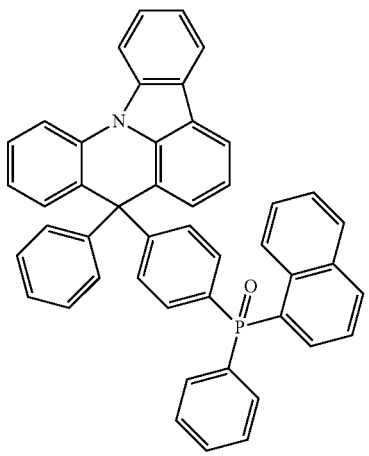 [SMILES: O=P(c1ccccc1)(c1ccc(C2(c3ccccc3)c3ccccc3-n3c4ccccc4c4cccc2c43)cc1)c1cccc2ccccc12] |
| 110 | 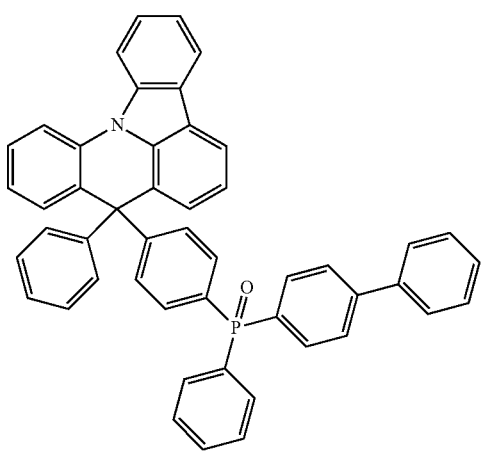 [SMILES: O=P(c1ccccc1)(c1ccc(-c2ccccc2)cc1)c1ccc(C2(c3ccccc3)c3ccccc3-n3c4ccccc4c4cccc2c43)cc1] |
| 111 | 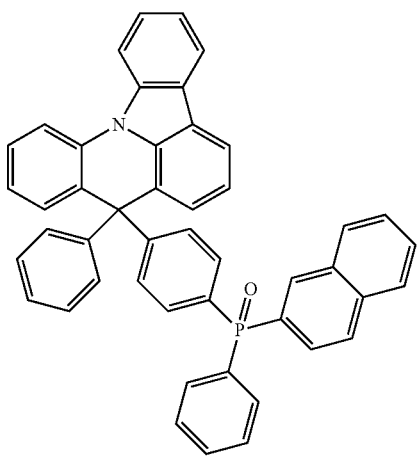 [SMILES: O=P(c1ccccc1)(c1ccc(C2(c3ccccc3)c3ccccc3-n3c4ccccc4c4cccc2c43)cc1)c1ccc2ccccc2c1] |
TABLE 12-continued
| Compound | Structural Formula |
|---|---|
| 112 | 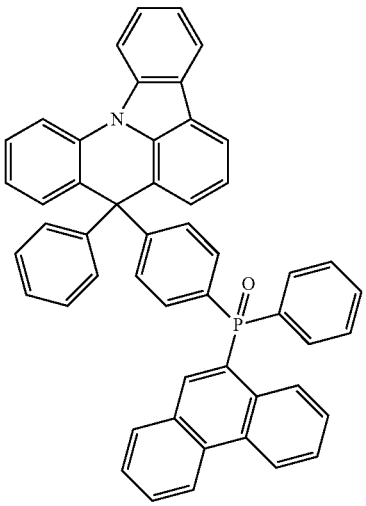 [SMILES: O=P(c1ccccc1)(c1ccc(C2(c3ccccc3)c3ccccc3-n3c4ccccc4c4cccc2c43)cc1)c1cc2ccccc2c2ccccc12] |
| 113 | 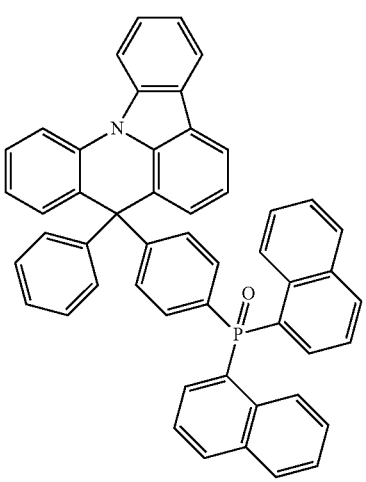 [SMILES: O=P(c1ccc(C2(c3ccccc3)c3ccccc3-n3c4ccccc4c4cccc2c43)cc1)(c1cccc2ccccc12)c1cccc2ccccc12] |
| 114 | 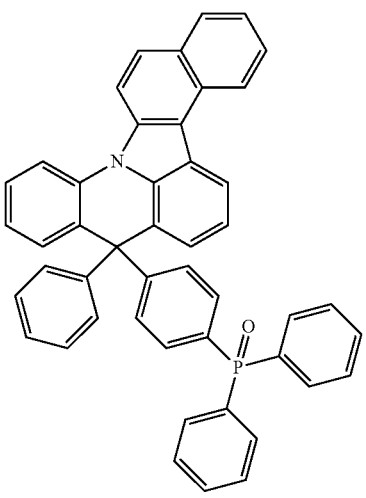 [SMILES: O=P(c1ccccc1)(c1ccccc1)c1ccc(C2(c3ccccc3)c3ccccc3-n3c4ccc5ccccc5c4c4cccc2c43)cc1] |

TABLE 12-continued
| Compound | Structural Formula |
|---|---|
| 115 | 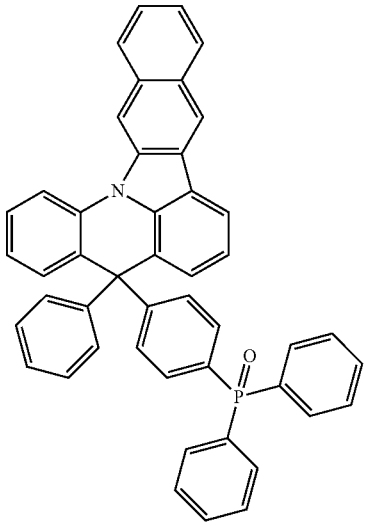 [SMILES: O=P(c1ccccc1)(c1ccccc1)c1ccc(C2(c3ccccc3)c3ccccc3-n3c4cc5ccccc5cc4c4cccc2c43)cc1] |
| 116 | 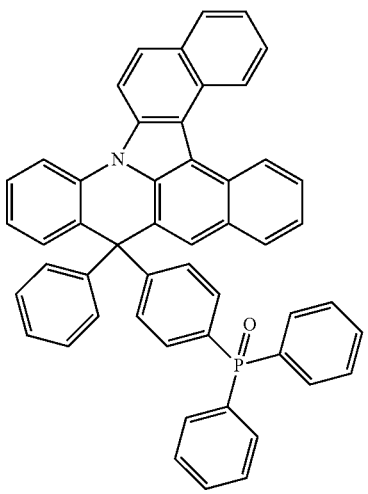 [SMILES: O=P(c1ccccc1)(c1ccccc1)c1ccc(C2(c3ccccc3)c3ccccc3-n3c4ccc5ccccc5c4c4c5ccccc5cc2c43)cc1] |
TABLE 13
| Compound | Structural Formula |
|---|---|
| 117 | 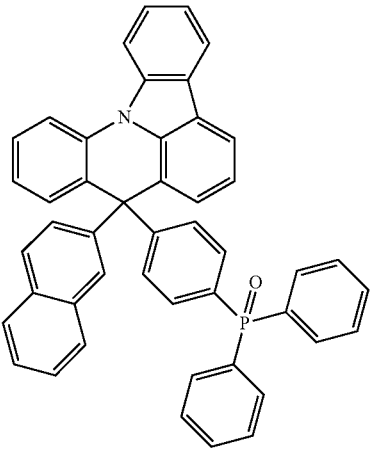 [SMILES: O=P(c1ccccc1)(c1ccccc1)c1ccc(C2(c3ccc4ccccc4c3)c3ccccc3-n3c4ccccc4c4cccc2c43)cc1] |
| 118 | 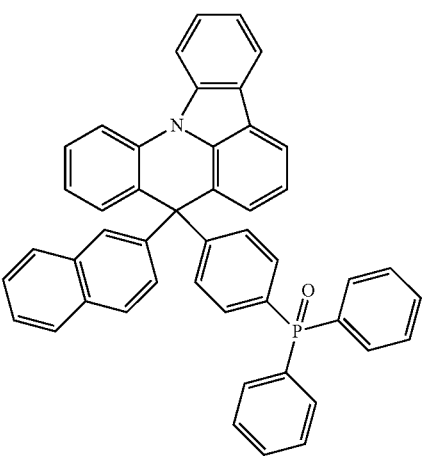 [SMILES: O=P(c1ccccc1)(c1ccccc1)c1ccc(C2(c3ccc4ccccc4c3)c3ccccc3-n3c4ccccc4c4cccc2c43)cc1] |
| 119 | 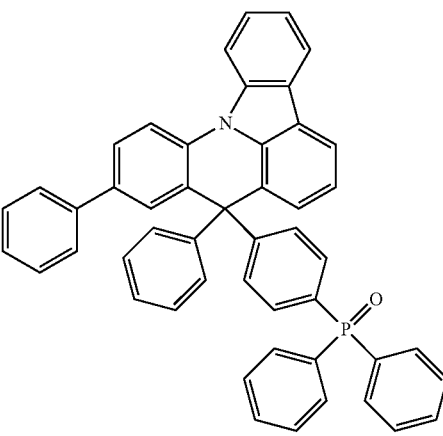 |

TABLE 13-continued
| Compound | Structural Formula |
|---|---|
| 120 | 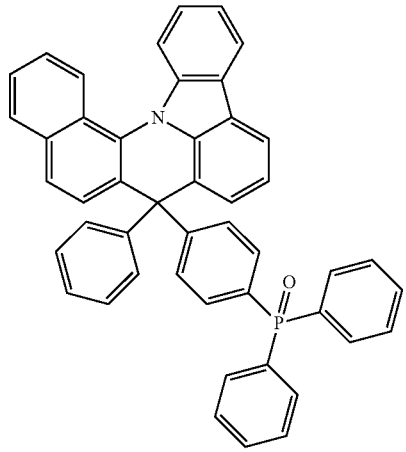 [SMILES: O=P(c1ccccc1)(c1ccccc1)c1ccc(C2(c3ccccc3)c3ccc4ccccc4c3-n3c4ccccc4c4cccc2c43)cc1] |
| 121 | 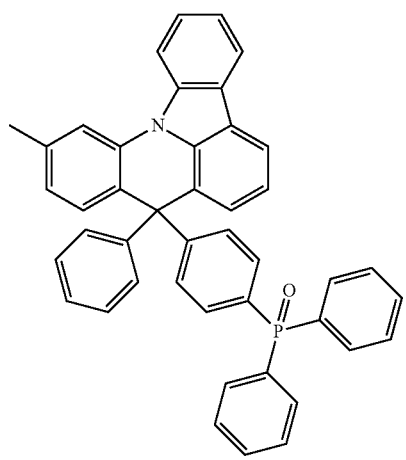 [SMILES: Cc1ccc2c(c1)-n1c3ccccc3c3cccc(c31)C2(c1ccccc1)c1ccc(P(=O)(c2ccccc2)c2ccccc2)cc1] |
| 122 | 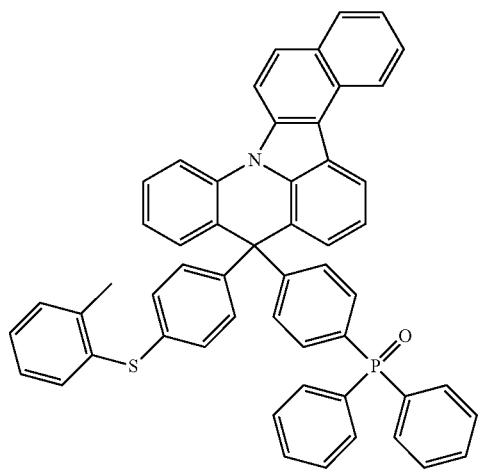 [SMILES: Cc1ccccc1Sc1ccc(C2(c3ccc(P(=O)(c4ccccc4)c4ccccc4)cc3)c3ccccc3-n3c4ccc5ccccc5c4c4cccc2c43)cc1] |
TABLE 13-continued
| Compound | Structural Formula |
|---|---|
| 121 | 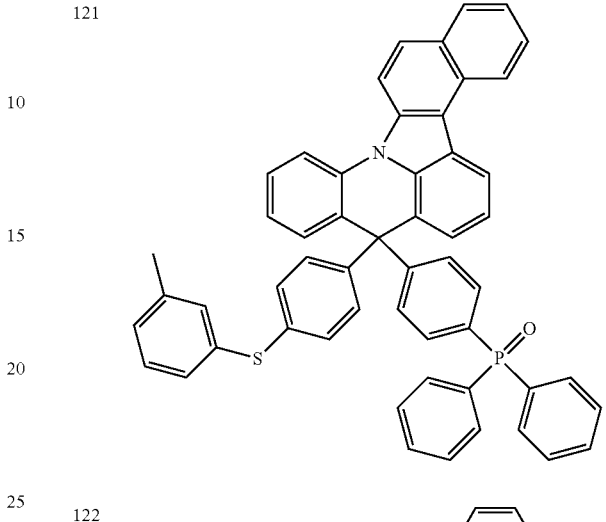 |
| 122 | 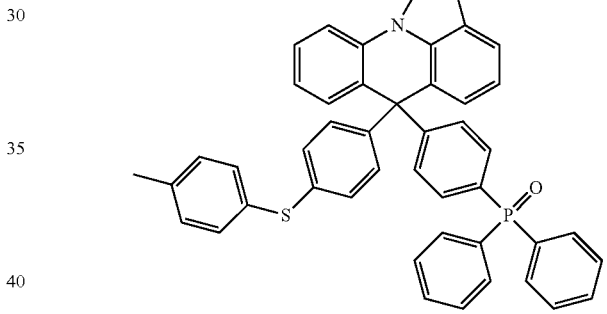 |
TABLE 14
| Compound | Structural Formula |
|---|---|
| 123 | 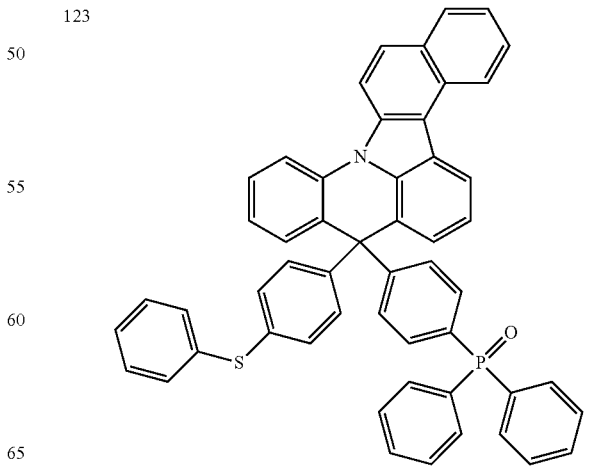 |

TABLE 14-continued
| Compound | Structural Formula |
|---|---|
| 124 | 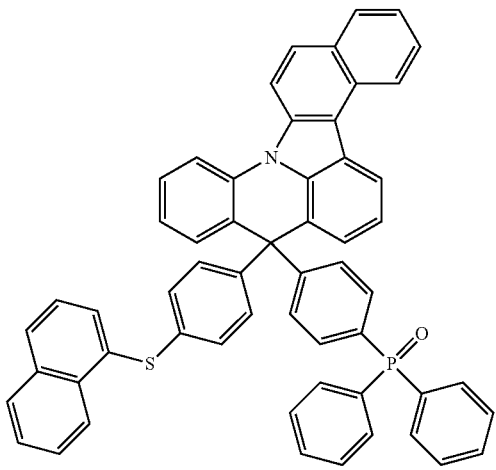 [SMILES: O=P(c1ccccc1)(c1ccccc1)c1ccc(C2(c3ccc(Sc4cccc5ccccc45)cc3)c3ccccc3-n3c4ccc5ccccc5c4c4cccc2c43)cc1] |
| 125 | 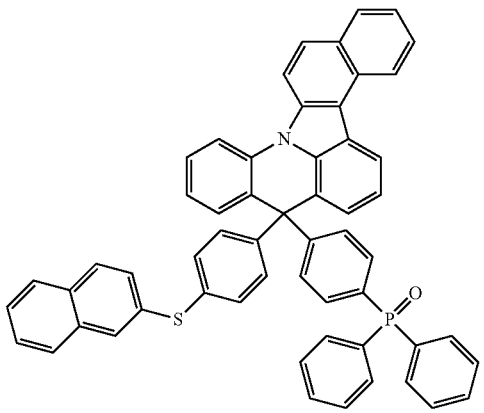 [SMILES: O=P(c1ccccc1)(c1ccccc1)c1ccc(C2(c3ccc(Sc4ccc5ccccc5c4)cc3)c3ccccc3-n3c4ccc5ccccc5c4c4cccc2c43)cc1] |
| 126 | 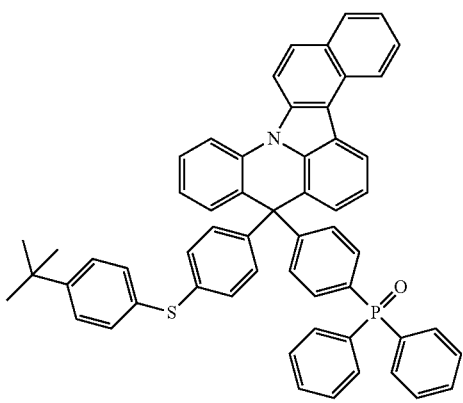 [SMILES: CC(C)(C)c1ccc(Sc2ccc(C3(c4ccc(P(=O)(c5ccccc5)c5ccccc5)cc4)c4ccccc4-n4c5ccc6ccccc6c5c5cccc3c54)cc2)cc1] |
| 127 | 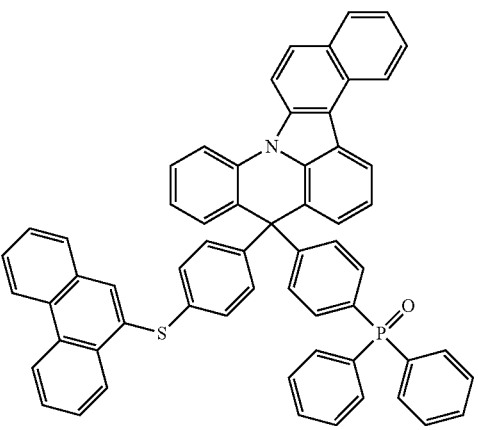 [SMILES: O=P(c1ccccc1)(c1ccccc1)c1ccc(C2(c3ccc(Sc4cc5ccccc5c5ccccc45)cc3)c3ccccc3-n3c4ccc5ccccc5c4c4cccc2c43)cc1] |
| 128 | 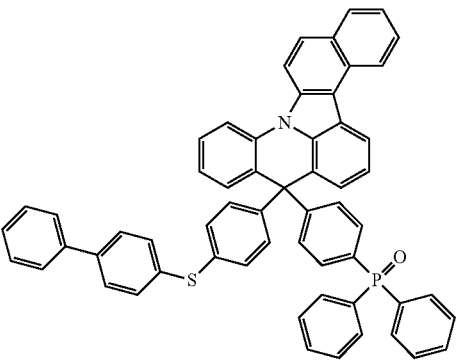 [SMILES: O=P(c1ccccc1)(c1ccccc1)c1ccc(C2(c3ccc(Sc4ccc(-c5ccccc5)cc4)cc3)c3ccccc3-n3c4ccc5ccccc5c4c4cccc2c43)cc1] |
| 129 | 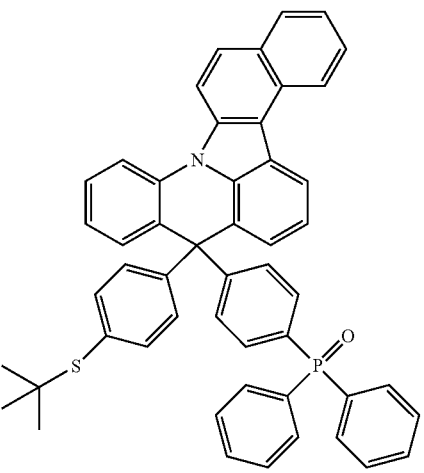 [SMILES: CC(C)(C)Sc1ccc(C2(c3ccc(P(=O)(c4ccccc4)c4ccccc4)cc3)c3ccccc3-n3c4ccc5ccccc5c4c4cccc2c43)cc1] |

TABLE 14-continued
| Compound | Structural Formula |
|---|---|
| 130 | 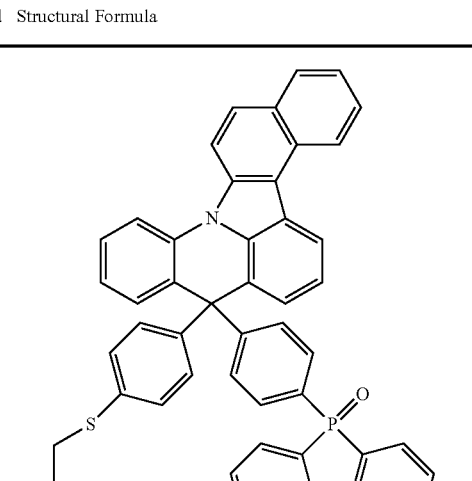 |
TABLE 15
| Compound | Structural Formula |
|---|---|
| 131 | |
| 132 | |
| 133 | |
| 134 | |
| 135 | |

TABLE 15-continued
| Compound | Structural Formula |
|---|---|
| 136 | 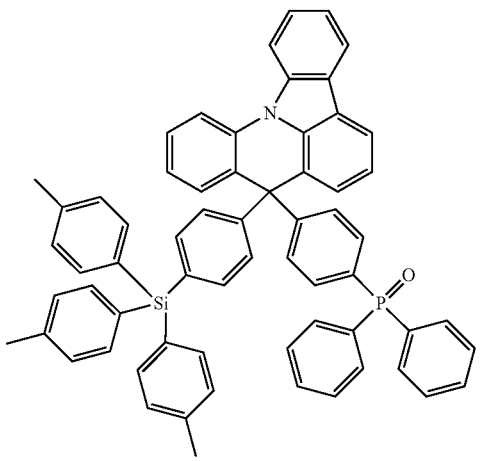 [SMILES: Cc1ccc([Si](c2ccc(C)cc2)(c2ccc(C)cc2)c2ccc(C3(c4ccc(P(=O)(c5ccccc5)c5ccccc5)cc4)c4ccccc4-n4c5ccccc5c5cccc3c54)cc2)cc1] |
| 137 | 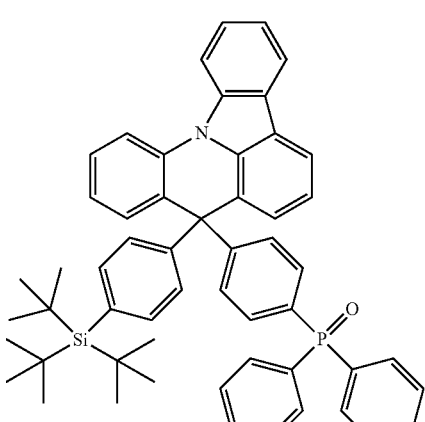 |
| 138 | 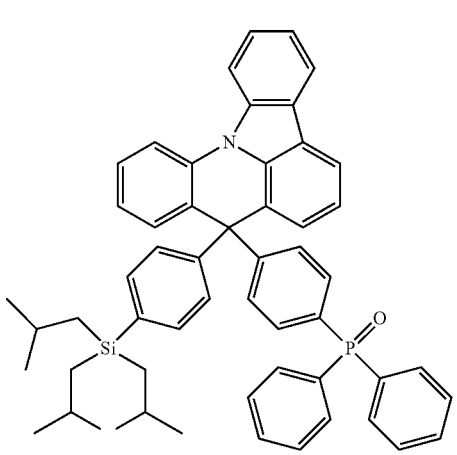 [SMILES: CC(C)C[Si](CC(C)C)(CC(C)C)c1ccc(C2(c3ccc(P(=O)(c4ccccc4)c4ccccc4)cc3)c3ccccc3-n3c4ccccc4c4cccc2c43)cc1] |
TABLE 16
| Compound | Structural Formula |
|---|---|
| 139 | 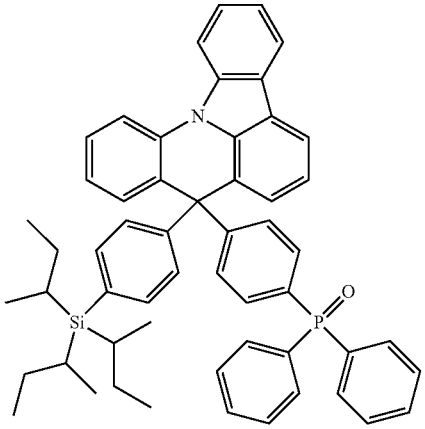 [SMILES: CCC(C)[Si](c1ccc(C2(c3ccc(P(=O)(c4ccccc4)c4ccccc4)cc3)c3ccccc3-n3c4ccccc4c4cccc2c43)cc1)(C(C)CC)C(C)CC] |
| 140 | 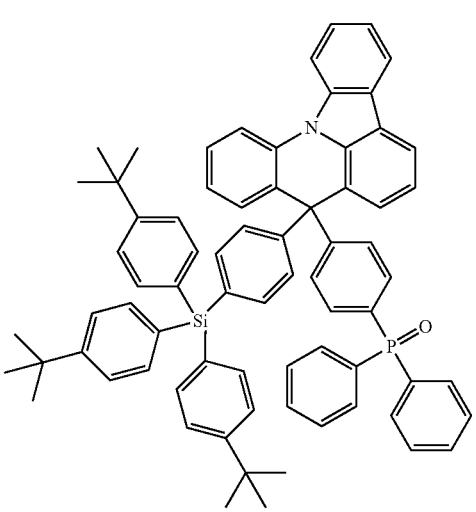 [SMILES: CC(C)(C)c1ccc([Si](c2ccc(C(C)(C)C)cc2)(c2ccc(C(C)(C)C)cc2)c2ccc(C3(c4ccc(P(=O)(c5ccccc5)c5ccccc5)cc4)c4ccccc4-n4c5ccccc5c5cccc3c54)cc2)cc1] |
| 141 | 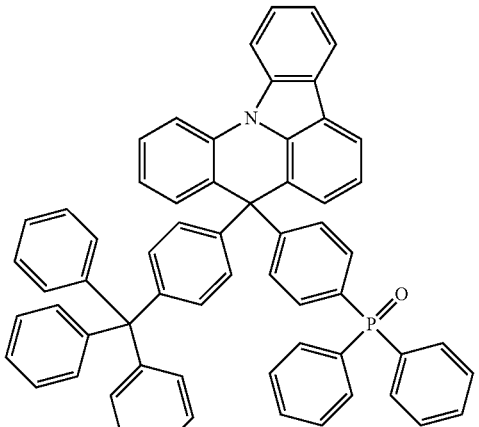 |

TABLE 16-continued
| Compound | Structural Formula |
|---|---|
| 142 | 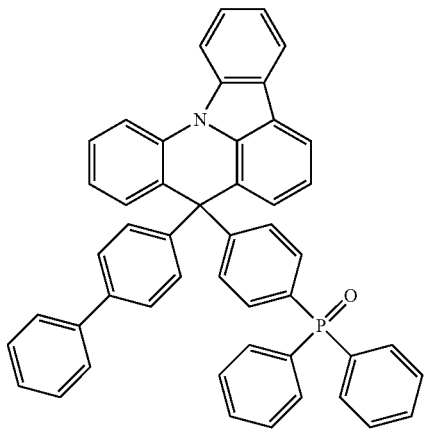 [SMILES: O=P(c1ccccc1)(c1ccccc1)c1ccc(C2(c3ccc(-c4ccccc4)cc3)c3ccccc3-n3c4ccccc4c4cccc2c43)cc1] |
| 143 | 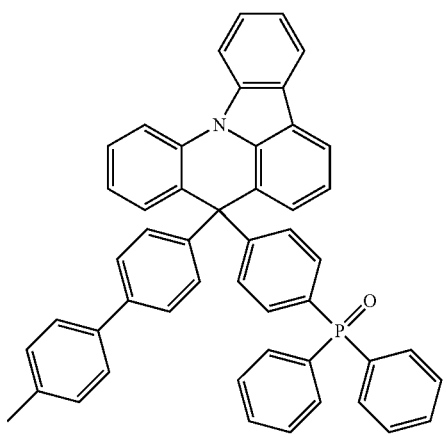 [SMILES: Cc1ccc(-c2ccc(C3(c4ccc(P(=O)(c5ccccc5)c5ccccc5)cc4)c4ccccc4-n4c5ccccc5c5cccc3c54)cc2)cc1] |
| 144 | 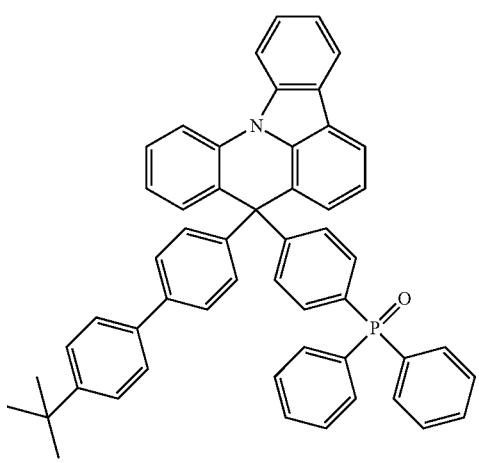 [SMILES: CC(C)(C)c1ccc(-c2ccc(C3(c4ccc(P(=O)(c5ccccc5)c5ccccc5)cc4)c4ccccc4-n4c5ccccc5c5cccc3c54)cc2)cc1] |
| 145 | 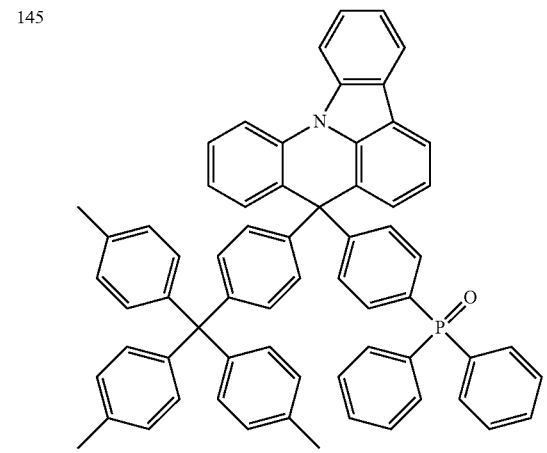 |
| 146 | 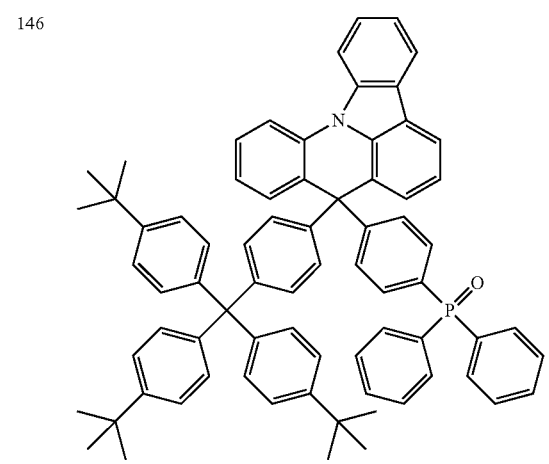 |
TABLE 17
| Compound | Structural Formula |
|---|---|
| 147 | 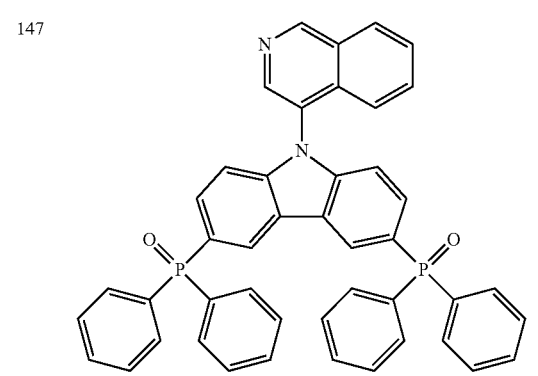 |

TABLE 17-continued
| Compound | Structural Formula |
|---|---|
| 148 | 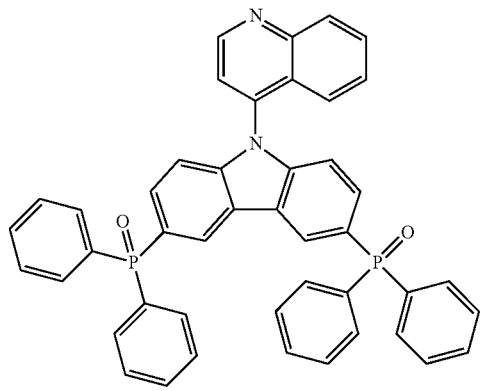 [SMILES: O=P(c1ccccc1)(c1ccccc1)c1ccc2c(c1)c1cc(P(=O)(c3ccccc3)c3ccccc3)ccc1n2-c1ccnc2ccccc12] |
| 149 | 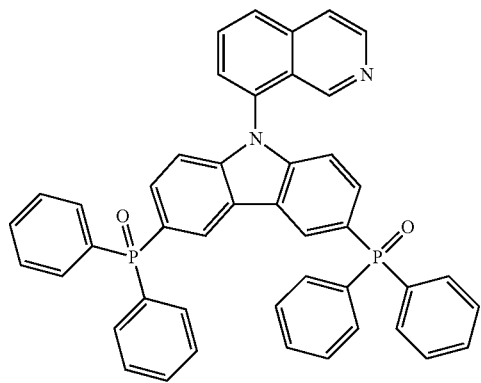 [SMILES: O=P(c1ccccc1)(c1ccccc1)c1ccc2c(c1)c1cc(P(=O)(c3ccccc3)c3ccccc3)ccc1n2-c1cccc2ccncc12] |
| 150 | 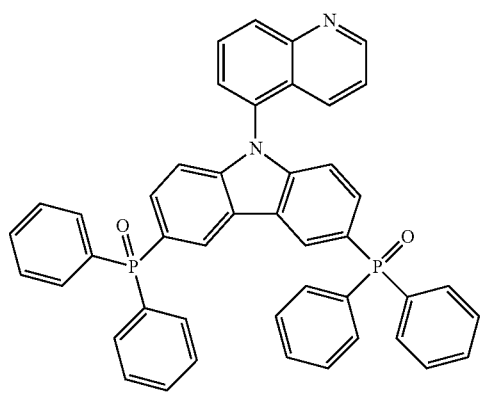 [SMILES: O=P(c1ccccc1)(c1ccccc1)c1ccc2c(c1)c1cc(P(=O)(c3ccccc3)c3ccccc3)ccc1n2-c1cccc2ncccc12] |
| 151 | 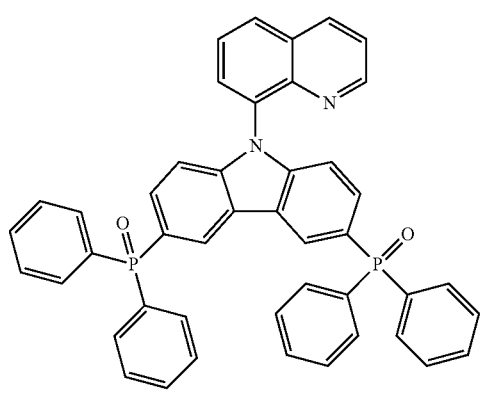 [SMILES: O=P(c1ccccc1)(c1ccccc1)c1ccc2c(c1)c1cc(P(=O)(c3ccccc3)c3ccccc3)ccc1n2-c1cccc2cccnc12] |
TABLE 17-continued
| Compound | Structural Formula |
|---|---|
| 152 | |
| 153 | |
| 154 | |

TABLE 18
| Compound | Structural Formula |
|---|---|
| 155 | 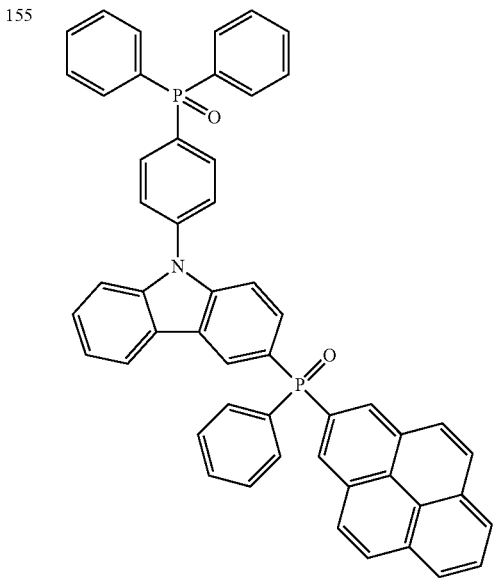 |
| 156 | 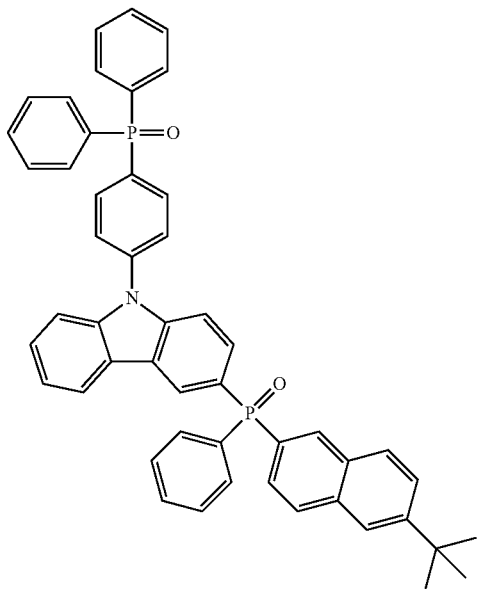 [SMILES: CC(C)(C)c1ccc2cc(P(=O)(c3ccccc3)c3ccc4c(c3)c3ccccc3n4-c3ccc(P(=O)(c4ccccc4)c4ccccc4)cc3)ccc2c1] |
TABLE 18-continued
| Compound | Structural Formula |
|---|---|
| 157 | |
| 158 | 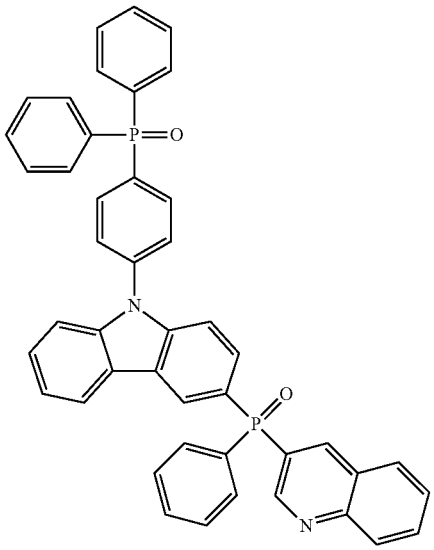 [SMILES: O=P(c1ccccc1)(c1ccccc1)c1ccc(-n2c3ccccc3c3cc(P(=O)(c4ccccc4)c4cnc5ccccc5c4)ccc32)cc1] |

TABLE 18-continued
| Compound | Structural Formula |
|---|---|
| 159 | 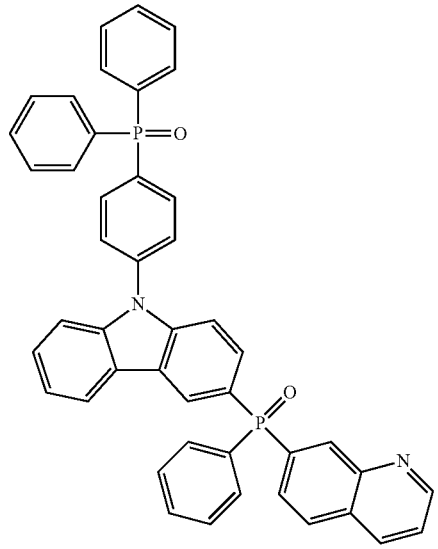 [SMILES: O=P(c1ccccc1)(c1ccccc1)c1ccc(-n2c3ccccc3c3cc(P(=O)(c4ccccc4)c4ccc5cccnc5c4)ccc32)cc1] |
| 160 | 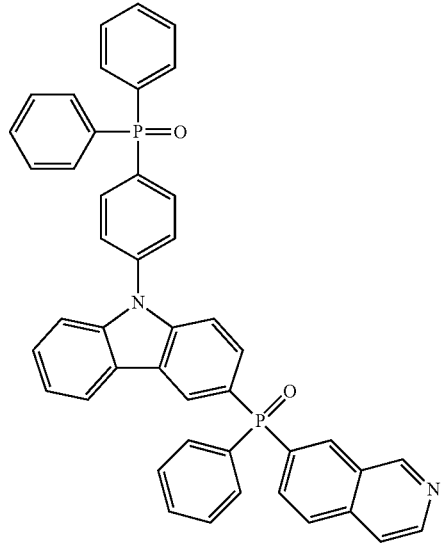 [SMILES: O=P(c1ccccc1)(c1ccccc1)c1ccc(-n2c3ccccc3c3cc(P(=O)(c4ccccc4)c4ccc5ccncc5c4)ccc32)cc1] |
| 161 | 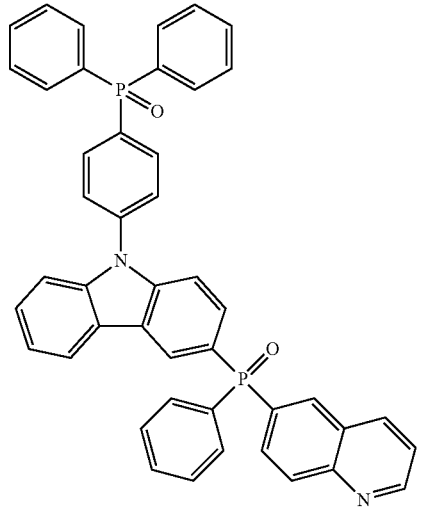 [SMILES: O=P(c1ccccc1)(c1ccccc1)c1ccc(-n2c3ccccc3c3cc(P(=O)(c4ccccc4)c4ccc5ncccc5c4)ccc32)cc1] |
TABLE 18-continued
| Compound | Structural Formula |
|---|---|
| 162 | 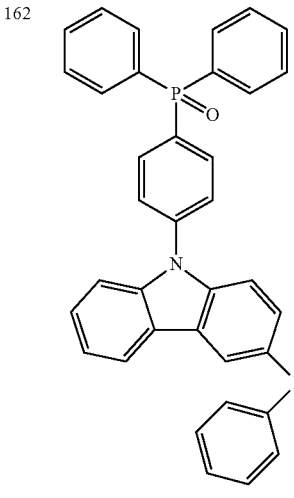 |
TABLE 19
| Compound | Structural Formula |
|---|---|
| 163 | 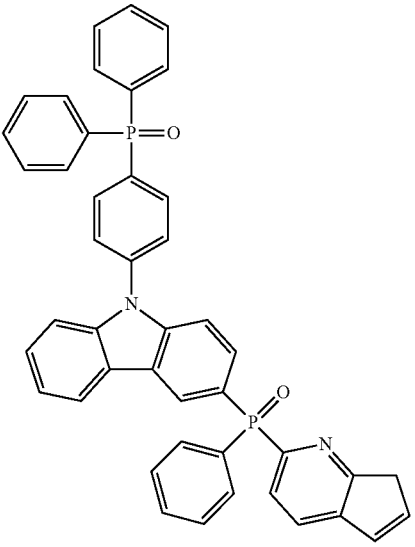 [SMILES: O=P(c1ccccc1)(c1ccccc1)c1ccc(-n2c3ccccc3c3cc(P(=O)(c4ccccc4)c4ccc5c(n4)CC=C5)ccc32)cc1] |

TABLE 19-continued
| Compound | Structural Formula |
|---|---|
| 164 | 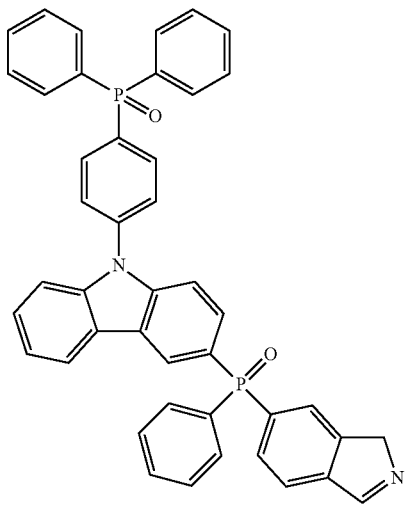 [SMILES: O=P(c1ccccc1)(c1ccccc1)c1ccc(-n2c3ccccc3c3cc(P(=O)(c4ccccc4)c4ccc5c(c4)CN=C5)ccc32)cc1] |
| 165 | 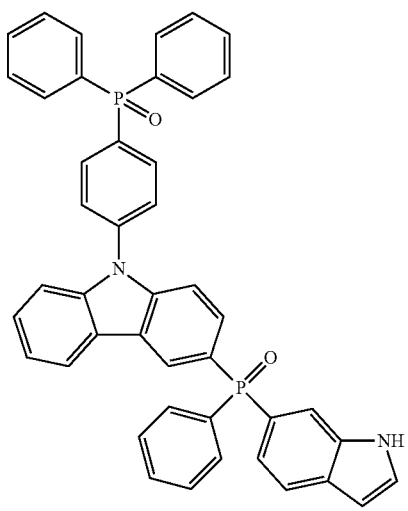 [SMILES: O=P(c1ccccc1)(c1ccccc1)c1ccc(-n2c3ccccc3c3cc(P(=O)(c4ccccc4)c4ccc5cc[nH]c5c4)ccc32)cc1] |
| 166 | 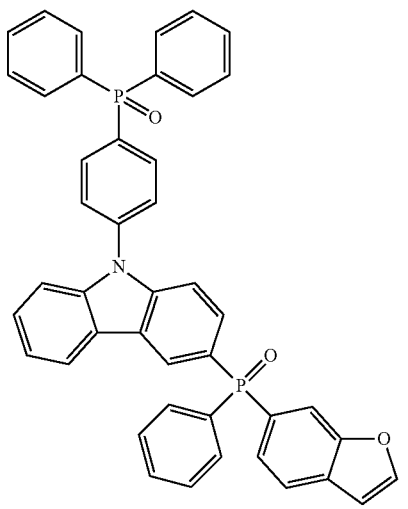 [SMILES: O=P(c1ccccc1)(c1ccccc1)c1ccc(-n2c3ccccc3c3cc(P(=O)(c4ccccc4)c4ccc5ccoc5c4)ccc32)cc1] |
| 167 | 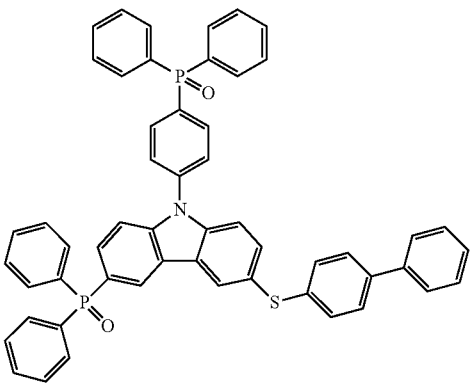 [SMILES: O=P(c1ccccc1)(c1ccccc1)c1ccc(-n2c3ccc(Sc4ccc(-c5ccccc5)cc4)cc3c3cc(P(=O)(c4ccccc4)c4ccccc4)ccc32)cc1] |
| 168 | 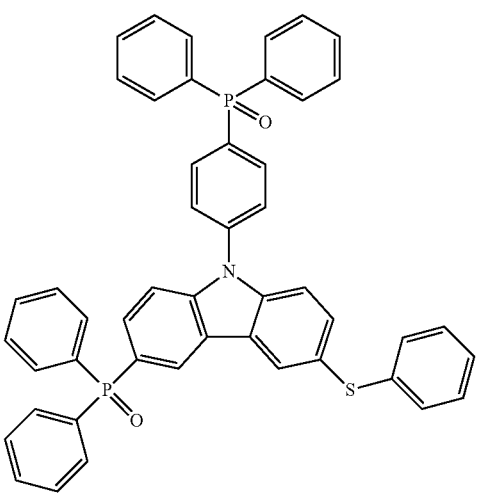 [SMILES: O=P(c1ccccc1)(c1ccccc1)c1ccc(-n2c3ccc(Sc4ccccc4)cc3c3cc(P(=O)(c4ccccc4)c4ccccc4)ccc32)cc1] |
| 169 | 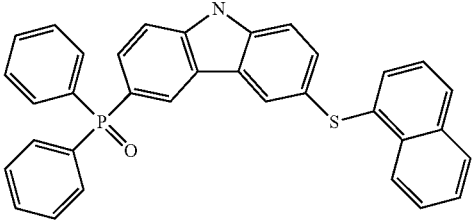 |

TABLE 19-continued

| Compound | Structural Formula |
|---|---|
| 170 | (structure) |

TABLE 20

| Compound | Structural Formula |
|---|---|
| 171 | (structure) |
| 172 | (structure) |
| 173 | (structure) |

TABLE 20-continued
| Compound | Structural Formula |
|---|---|
| 174 | 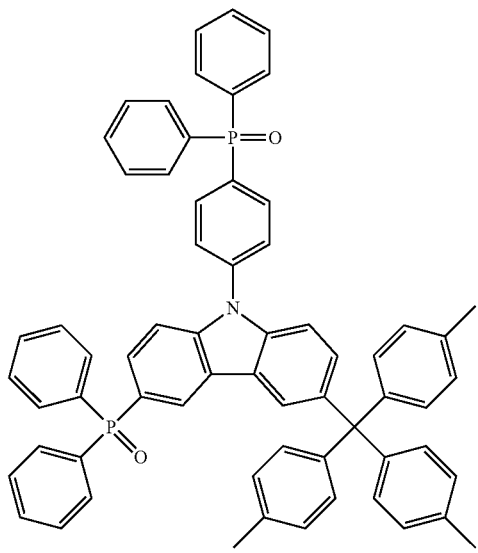 [SMILES: Cc1ccc(C(c2ccc(C)cc2)(c2ccc(C)cc2)c2ccc3c(c2)c2cc(P(=O)(c4ccccc4)c4ccccc4)ccc2n3-c2ccc(P(=O)(c3ccccc3)c3ccccc3)cc2)cc1] |
| 175 | 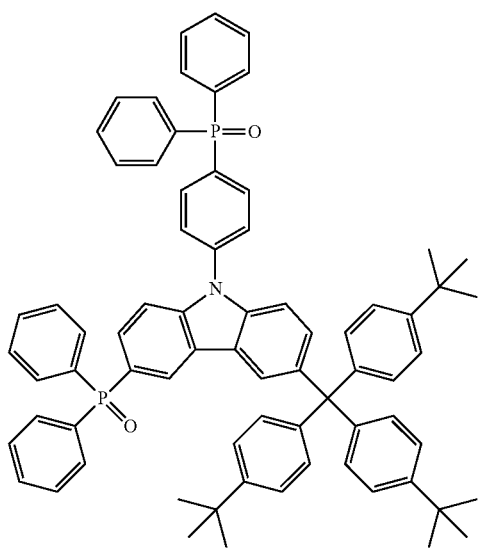 [SMILES: CC(C)(C)c1ccc(C(c2ccc(C(C)(C)C)cc2)(c2ccc(C(C)(C)C)cc2)c2ccc3c(c2)c2cc(P(=O)(c4ccccc4)c4ccccc4)ccc2n3-c2ccc(P(=O)(c3ccccc3)c3ccccc3)cc2)cc1] |
| 176 | 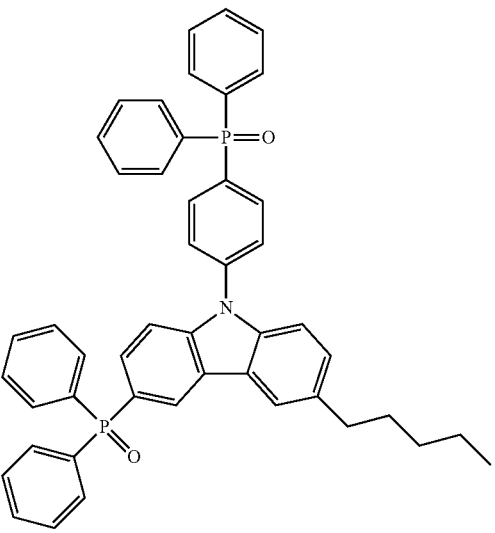 [SMILES: CCCCCc1ccc2c(c1)c1cc(P(=O)(c3ccccc3)c3ccccc3)ccc1n2-c1ccc(P(=O)(c2ccccc2)c2ccccc2)cc1] |
| 177 | 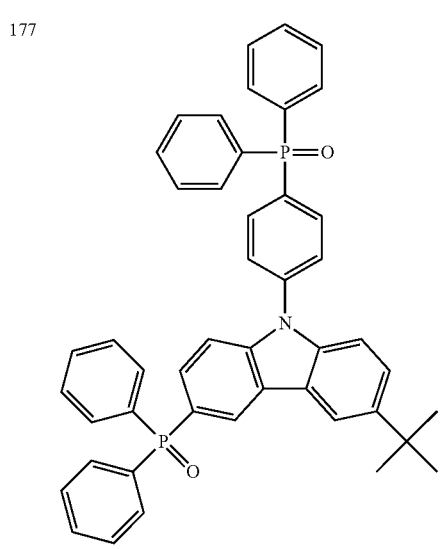 |

TABLE 20-continued
| Compound | Structural Formula |
|---|---|
| 178 | |
TABLE 21
| Compound | Structural Formula |
|---|---|
| 179 | |
TABLE 21-continued
| Compound | Structural Formula |
|---|---|
| 180 | 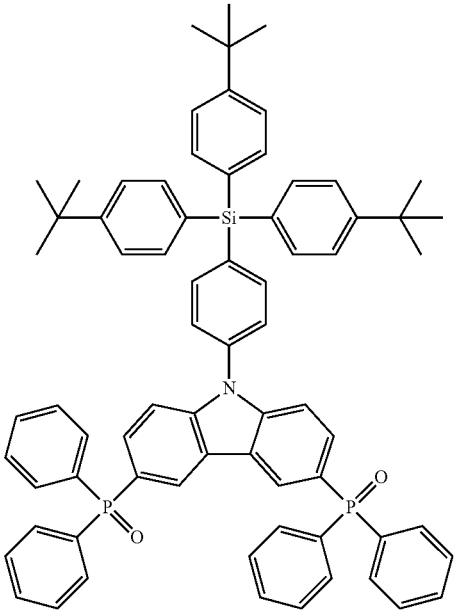 |
| 181 | 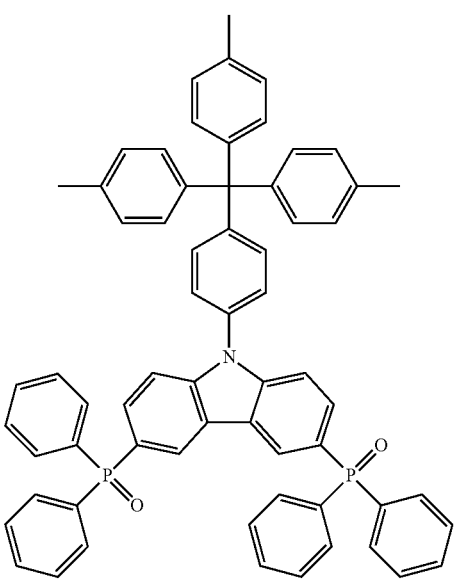 [SMILES: Cc1ccc(C(c2ccc(C)cc2)(c2ccc(C)cc2)c2ccc(-n3c4ccc(P(=O)(c5ccccc5)c5ccccc5)cc4c4cc(P(=O)(c5ccccc5)c5ccccc5)ccc43)cc2)cc1] |

TABLE 21-continued

| Compound | Structural Formula |
|---|---|
| 182 | |
| 183 | |
| 184 | |
| 185 | |
| 186 | |

TABLE 22

| Compound | Structural Formula |
|---|---|
| 187 | |

TABLE 22-continued

| Compound | Structural Formula |
|---|---|
| 188 | |
| 189 | |
| 190 | |
| 191 | |
| 192 | |
| 193 | |

TABLE 22-continued

| Compound | Structural Formula |
|---|---|
| 194 | 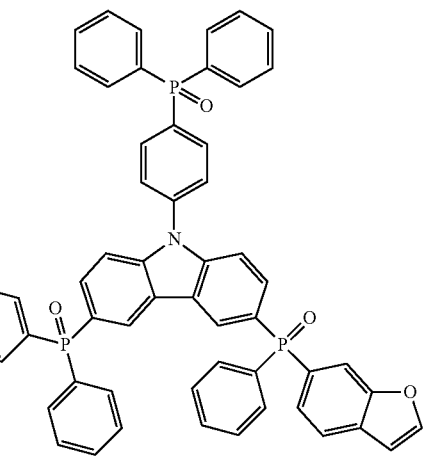 |

With reference to the appended drawings, the organic EL device according to the present invention is described below.

FIG. 1 schematically shows the structure of the organic EL device according to the present invention. The organic EL device including the compound represented by Chemical Formulas 1 to 8 may be embodied in a variety of structures.

As shown in FIG. 1, the organic EL device according to the present invention includes a first electrode 110; a second electrode 150; and a single organic layer or a plurality of organic layers 120, 130, 140 having at least one light-emitting layer 130 interposed between the first electrode and the second electrode, wherein the organic layers 120, 130, 140 may include part or all of the compounds of Chemical Formulas 1 to 8 as described above.

The number of the plurality of organic layers may be 10 or less, and preferably 8 or less. If the number of organic layers exceeds 10, it is difficult to form organic layers of the organic EL device and economic benefits are negated.

As typically illustrated in FIG. 1, the organic EL device according to an embodiment of the present invention is configured such that a light-emitting layer 130, a hole transport layer 120 and an electron transport layer 140 are disposed between an anode 110 as the first electrode and a cathode 150 as the second electrode. In addition to the light-emitting layer 130, the hole transport layer 120 or the electron transport layer 140, part or all of an electron injection layer, a hole injection layer, a hole blocking layer, or an electron blocking layer may be separately formed, thus enabling the luminous efficiency of the organic EL device to increase.

The organic EL device is preferably supported on a transparent substrate. The material for the transparent substrate is not particularly limited so long as it has good mechanical strength, thermal stability and transparency. Specific examples thereof include glass, a transparent plastic film, etc.

The anode material of the organic EL device according to the present invention may include a metal having a work function of 4 eV or more, an alloy, an electrical conductive compound, or a mixture thereof. Specific examples thereof include Au metal or a transparent conductive material such as CuI, ITO (Indium Tin Oxide), $SnO_2$ and ZnO. The thickness of the anode film may be 10 to 200 nm.

The cathode material of the organic EL device according to the present invention may include a metal having a work function of less than 4 eV, an alloy, an electrical conductive compound, or a mixture thereof. Specific examples thereof include Na, Na—K alloy, Ca, Mg, Li, Li alloy, In, Al, Mg alloy, Al alloy, etc. In addition, $Al/AlO_2$, Al/Li, Mg/Ag or Mg/In may be used. The thickness of the cathode film may be 10 to 200 nm. In order to increase the luminous efficiency of the organic EL device, one or more electrodes should have a light transmittance of 10% or more. The sheet resistance of the electrodes is preferably hundreds of Ω/mm or less. The thickness of the electrodes may range from 10 nm to 1 μm, and preferably from 10 to 400 nm. Such electrodes may be obtained by forming the above electrode material into a thin film using vapor deposition such as chemical vapor deposition (CVD) or physical vapor deposition (PVD) or sputtering.

Also, the hole transport material and the hole injection material may be optionally selected from materials typically used as a hole transport material among light conductive materials and materials known to be useful for forming a hole transport layer or a hole injection layer of an organic EL device, in addition to the compounds of Chemical Formulas 1 to 8 according to the present invention. Examples thereof include porphyrin compound derivatives including N,N'-diphenyl-N,N'-di(3-methylphenyl)-4,4'-diaminobiphenyl (TPD), N,N'-diphenyl-N,N'-dinaphthyl-4,4'-diaminobiphenyl, N,N,N',N'-tetra-p-tolyl-4,4'-diaminobiphenyl, N,N,N',N'-tetraphenyl-4,4'-diaminobiphenyl, copper (II) 1,10,15,20-tetraphenyl-21H,23H-porphyrin, etc., triarylamine derivatives including polymers having aromatic tertiary amines on the main chains or side chains thereof, 1,1-bis(4-di-p-tolylaminophenyl)cyclohexane, N,N,N-tri(p-tolyl) amine, 4,4',4'-tris[N-(3-methylphenyl)-N-phenylamino] triphenylamine, etc., carbazole derivatives including N-phenylcarbazole and polyvinylcarbazole, phthalocyanine derivatives including nonmetallic phthalocyanine, copper phthalocyanine, etc., starbust amine derivatives, enamine stilbene derivatives, derivatives of aromatic tertiary amines and styryl amine compounds, and polysilane.

Known materials for the electron transport layer include, for example, $AlQ_3$, a 2,5-diaryl silole derivative (Py-PySPyPy), a perfluorinated compound (PF-6P), octasubstituted cyclooctatetraene compounds (COTs), etc., which may be mixed.

In the organic EL device according to the present invention, the electron injection layer, the electron transport layer, the hole injection layer and the hole transport layer may be provided in the form of a single layer containing one or more kinds of the above compounds, or of a laminated plurality of layers containing different kinds of compounds.

Another light-emitting material employed in the organic EL device according to the present invention may include known light-emitting materials, for example, photoluminescent fluorescent materials, fluorescent brighteners, laser dyes, organic scintillators, and fluorescent analysis reagents. Specific examples thereof include polyaromatic compounds including $AlQ_3$, anthracene, phenanthrene, pyrene, crysene, perylene, coronene, rubrene and quinacridone, oligophenylene compounds including quaterphenyl, scintillators for liquid scintillation including 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl) benzene, 2,5-bis(5-t-butyl-2-benzoxazolyl)thiophene, 1,4-diphenyl-1,3-butadiene, 1,6-diphenyl-1,3,5-hexatriene, 1,1, 4,4-tetraphenyl-1,3-butadiene, etc., metal complexes of oxine derivatives, coumarin dyes, dicyanomethylenepyrane dyes, dicyanomethylenethiopyrane dyes, polymethine dyes, oxobenzanthracene dyes, xanthene dyes, carbostyryl dyes, perylene dyes, oxazine compounds, stilbene derivatives, spiro compounds, oxadiazole compounds, etc.

Respective layers of the organic EL device according to the present invention may be provided in the form of a thin film using a known process such as vacuum deposition, spin coating or casting, or may be prepared using materials therefor. The film thickness of respective layers is not particularly limited, and may be appropriately determined depending on the properties of the materials, and may be typically set in the range of 2 nm to 5000 nm.

Because the compound of Chemical Formulas 1 to 8 according to the present invention may be subjected to vacuum deposition, a thin-film forming process is simple and a uniform thin film having almost no pin holes may be easily obtained.

In FIG. 1, according to another embodiment of the present invention, the light-emitting layer 130 may include the compound for an organic EL device as represented by Chemical Formulas 1 to 8.

In FIG. 1, according to a further embodiment of the present invention, an organic EL device may be provided, wherein the organic layers 120, 130, 140 may include a hole transport layer 120, in which the hole transport layer 120 may include the compound for an organic EL device as represented by Chemical Formulas 1 to 8.

The preparation of the compounds for an organic EL device according to the present invention and the organic EL devices including the same is described in more detail via the following examples, which are merely illustrative but the scope of the present invention is not limited thereto.

EXAMPLE

According to the present invention, compounds for an organic EL device were prepared, and organic EL devices were manufactured using the same. The following preparation examples and examples are set to illustrate the present invention but are not construed to limit the present invention.

Preparation Example

Preparation Example 1

Synthesis of Intermediate 2.5 g of carbazole, 2 g of bromobenzene and 0.064 g of a palladium acetate catalyst were dissolved in 40 mL of toluene, and the resulting solution was heated to 60° C. Subsequently, a solution of 1.5 g of sodium butoxide and 0.385 g of tri-tert-butylphosphine dissolved in toluene was slowly added dropwise. The mixture was refluxed at a steady 100° C. After completion of the reaction, the reaction mixture was extracted with dichloromethane and distilled water, and the solvent was dried. The resulting solid was filtered and purified, yielding a 9-phenyl carbazole compound as an intermediate.

Preparation Example 2

Synthesis of Intermediate 2 g of 9-phenyl carbazole and 1.46 g of N-bromosuccinimide were dissolved in N,N-dimethylformamide, and the resulting solution was brominated, yielding a 3-bromo-9-phenyl carbazole compound as an intermediate. By the same method, a 3,6-dibromo-9-phenyl carbazole compound was synthesized.

Preparation Example 3

Synthesis of Intermediate 1.4 g of carbazole, 2.2 g of 1,4-dibromobenzene and 0.042 g of a palladium acetate catalyst were dissolved in 30 mL of toluene, and the resulting solution was heated to 60° C. Subsequently, a solution of 0.977 g of sodium butoxide and 0.257 g of tri-tert-butylphosphine dissolved in toluene was slowly added dropwise. The mixture was refluxed at a steady 100° C. After completion of the reaction, the reaction mixture was extracted with dichloromethane and distilled water, and the solvent was dried. The resulting solid was filtered and purified, yielding a 4-bromophenyl-9-carbazole compound as an intermediate.

Preparation Example 4

Synthesis of Intermediate

To 4.58 g of 3,6-dibromo-9-phenyl carbazole as the intermediate of Preparation Example 2 was added 60 mL of tetrahydrofuran, and the temperature was adjusted to −78° C. Subsequently, 1.26 mL of butyllithium was slowly added dropwise. The mixture was stirred for 2 hours while maintaining its temperature, and 3.71 g of chlorotriphenylsilane was slowly added dropwise, after which the temperature of the mixture was raised to room temperature. After completion of the reaction, triethylamine and methanol were added at a ratio of 1:10, and the reaction mixture was stirred and extracted, followed by drying the solvent. The resulting solid was filtered and purified, yielding 3-bromo-9-phenyl-6-(triphenylsilyl)-9-carbazole as a white intermediate.

Preparation Example 5

Synthesis of Intermediate 2 g of 4-bromophenyl-9-carbazole as the intermediate of Preparation Example 3, and 1.1 g of N-bromosuccinimide were dissolved in N,N-dimethylformamide, and the resulting solution was brominated, thus synthesizing a 3-bromo-9-(4-bromophenyl)carbazole compound as an intermediate.

Preparation Example 6

Synthesis of Intermediate 2 g of 9-phenyl-carbazole as the intermediate of Preparation Example 1, and 5.12 g of N-bromosuccinimide were dissolved in N,N-dimethylformamide, and the resulting solution was brominated, thus synthesizing a 3,6-dibromo-9-(4-bromophenyl)carbazole compound as an intermediate.

Preparation Example 7

Synthesis of Intermediate 0.5 g of iodo-3,5-dibromobenzene, 0.19 g of carbazole, a copper catalyst, 18-crown-6, and potassium carbonate were dissolved in dichlorobenzene, and the resulting solution was allowed to react while being heated to 150° C. After completion of the reaction, Cu powder was filtered, and the reaction mixture was extracted with distilled water and dichloromethane. The organic solvent was dried, and the resulting powder was purified using a column, thus synthesizing 9-(3,5-dibromophenyl)-9-carbazole as an intermediate.

Preparation Example 8

Synthesis of Intermediate 1.672 g of carbazole, 1.6 mL of 1-bromo-2-iodobenzene, 2.7646 g of potassium carbonate, 95 mg of copper iodide and 25 mL of xylene were refluxed in a nitrogen atmosphere. The mixture was cooled to room temperature, extracted with ethyl acetate, and dried with anhydrous magnesium sulfate to remove moisture, and the solvent was removed under reduced pressure. Silica gel column separation using a hexane solvent was conducted, thus obtaining a compound from which the solvent was then removed under reduced pressure, followed by vacuum drying, yielding 9-(2-bromophenyl)-9H-carbazole as a desired white solid intermediate.

Preparation Example 9

Synthesis of Intermediate 0.8 g of 9-(2-bromophenyl)-9H-carbazole as the intermediate of Preparation Example 8 was dissolved in 10 mL of purified tetrahydrofuran, and the resulting solution was cooled to −78° C., and 0.99 mL of butyllithium was slowly added dropwise. The mixture was stirred at the same temperature for 40 min and then further stirred at room temperature for an additional 3 hours. The reaction was terminated with aqueous ammonium chloride, and the reaction mixture was extracted with ethyl ether. The organic layer was dewatered using anhydrous magnesium sulfate, and the organic solvent was then removed. The resulting solid was dispersed in ethanol, stirred for one day, filtered, and vacuum dried, thus obtaining an intermediate material. The solid thus obtained was dispersed in 10 mL of acetic acid, and 10 drops of concentrated sulfuric acid were added, after which the mixture was refluxed for 4 hours. The resulting solid was filtered, washed with ethanol, and vacuum dried, yielding a 8-(4-bromophenyl)-8-phenyl-8H-indolo-[3,2,1-de]acridine compound.

Preparation Example 10

Synthesis of Intermediate 1.0 g of 9-(2-bromophenyl)-9H-carbazole as the intermediate of Preparation Example 8 was dissolved in 10 mL of purified tetrahydrofuran, and the resulting solution was cooled to −78° C., and 1.613 mL of butyllithium was slowly added dropwise. The mixture was stirred at the same temperature for 30 min, and 1.05 g of 4-bromobenzophenone was added. The mixture was stirred at the same temperature for 40 min and then further stirred at room temperature for an additional 3 hours. The reaction was terminated with aqueous ammonium chloride, and the reaction mixture was extracted with ethyl ether. The organic layer was dewatered using anhydrous magnesium sulfate, and the organic solvent was then removed. The resulting solid was dispersed in ethanol, stirred for one day, filtered, and vacuum dried, thus obtaining an intermediate material. The solid thus obtained was dispersed in 10 mL of acetic acid, and 10 drops of concentrated sulfuric acid were added, after which the mixture was refluxed for 4 hours. The resulting solid was filtered, washed with ethanol, and vacuum dried, yielding a 8-(4-bromophenyl)-8-phenyl-8H-indolo-[3,2,1-de]acridine compound.

Preparation Example 11

Synthesis of Intermediate 6.96 g of 9-(2-bromophenyl)-9H-carbazole as the intermediate of Preparation Example 8 was dissolved in 10 mL of purified tetrahydrofuran, and the resulting solution was cooled to −78° C. and 8.64 mL of butyllithium was slowly added dropwise. The mixture was stirred at the same temperature for 30 min, and 6.12 g of 4,4'-dibromobenzophenone was added. The mixture was stirred at the same temperature for 40 min and then further stirred at room temperature for an additional 3 hours. The reaction was terminated with aqueous ammonium chloride, and the reaction mixture was extracted with ethyl ether. The organic layer was dewatered using anhydrous magnesium sulfate, and the organic solvent was then removed. The resulting solid was dispersed in ethanol, stirred for one day, filtered, and vacuum dried, thus obtaining an intermediate material. The solid thus obtained was dispersed in 10 mL of acetic acid, and 10 drops of concentrated sulfuric acid were added, after which the mixture was refluxed for 4 hours. The resulting solid was filtered, washed with ethanol, and vacuum dried, yielding a 8,8-bis(4-bromophenyl)-8H-indolo[3,2,1-de]acridine compound.

Preparation Example 12

Synthesis of Compound 1

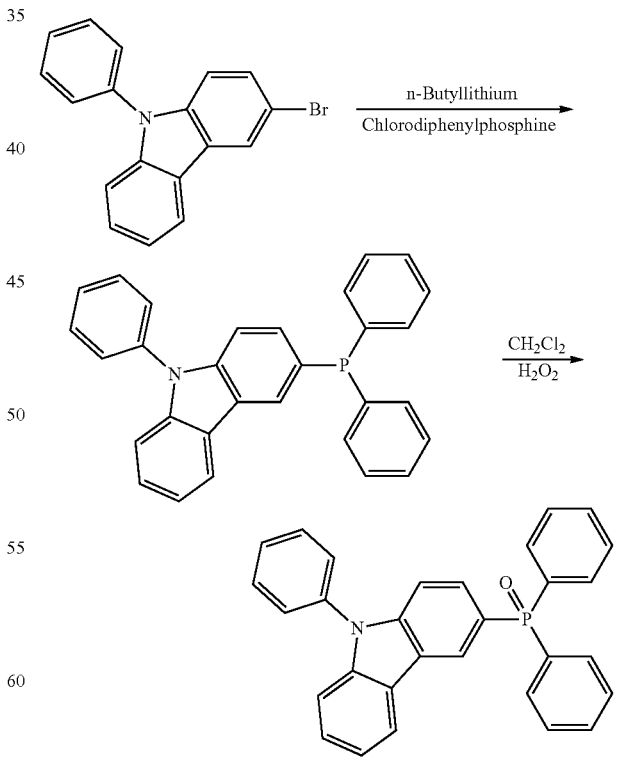

This compound was synthesized by reacting phosphonyl chloride with bromo(N-phenyl carbazole) and then performing oxidation.

30 mL of tetrahydrofuran was added to 2 g of 3-bromo-9-phenyl carbazole and the temperature was adjusted to −78° C. Subsequently, 0.8 mL of butyllithium was slowly added dropwise. While maintaining the temperature, the mixture was stirred for 2 hours, and 1.5 mL of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 3-(diphenylphosphonyl)-9-phenyl carbazole (PPO1) as white phosphine oxide corresponding to Compound 1 having the structure of the represented chemical formula. The glass transition temperature was 74° C., and the boiling point was 201° C.

Nuclear magnetic resonance analysis and mass analysis were performed, and the analytical results were as follows.

1H NMR-1H (200 MHz, CDCl$_3$): δ 8.59-8.53 (d, 1H), 8.12-8.08 (d, 1H), 7.78-7.68 (m, 5H), 7.62-7.42 (m, 14H), 7.35-7.31 (d, 1H). MS (FAB) m/z 443.48 [(M+1)$^+$].

Preparation Example 13

Synthesis of Compound 2

30 mL of tetrahydrofuran was added to 2 g of 3,6-dibromo-9-phenyl-carbazole, and the temperature was adjusted to −78° C. Subsequently, 0.84 mL of butyllithium was slowly added dropwise. While maintaining the temperature, the mixture was stirred for 2 hours, and 2.42 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 3,6-bis(diphenylphosphonyl)-9-phenyl carbazole (PPO2) having the structure of Compound 2 as white phosphine oxide. The glass transition temperature was 123° C., and the boiling point was 255° C.

Nuclear magnetic resonance analysis and mass analysis were performed, and the analytical results were as follows.

NMR-1H (200 MHz, CDCl$_3$): δ 8.48-8.41 (d, 3H), 7.76-7.64 (m, 8H), 7.59-7.54 (m, 7H), 7.52-7.42 (m, 13H). MS (FAB) m/z 643.65 [(M+1)$^+$].

Preparation Example 14

Synthesis of Compound 3

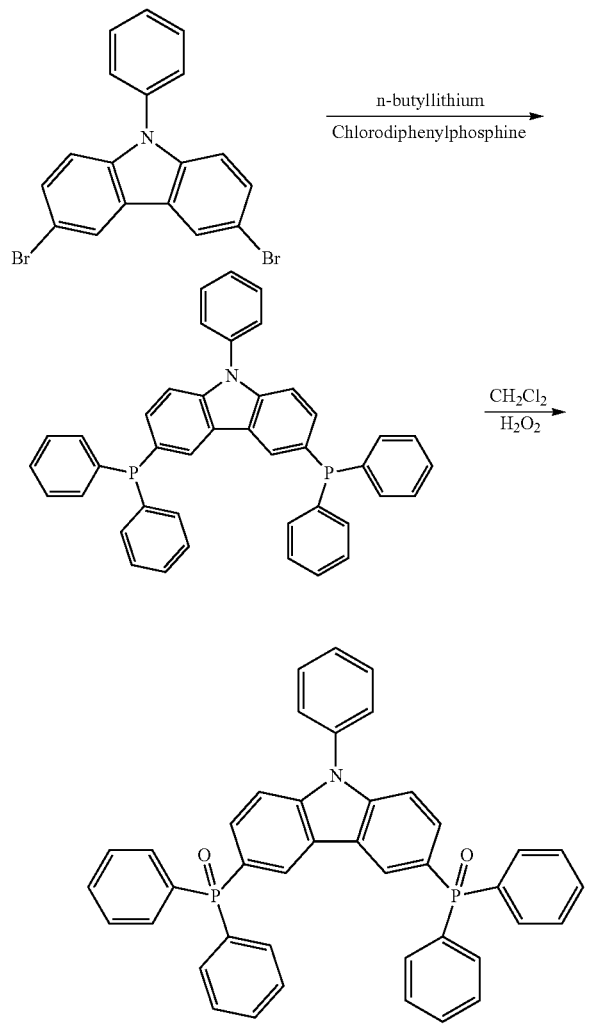

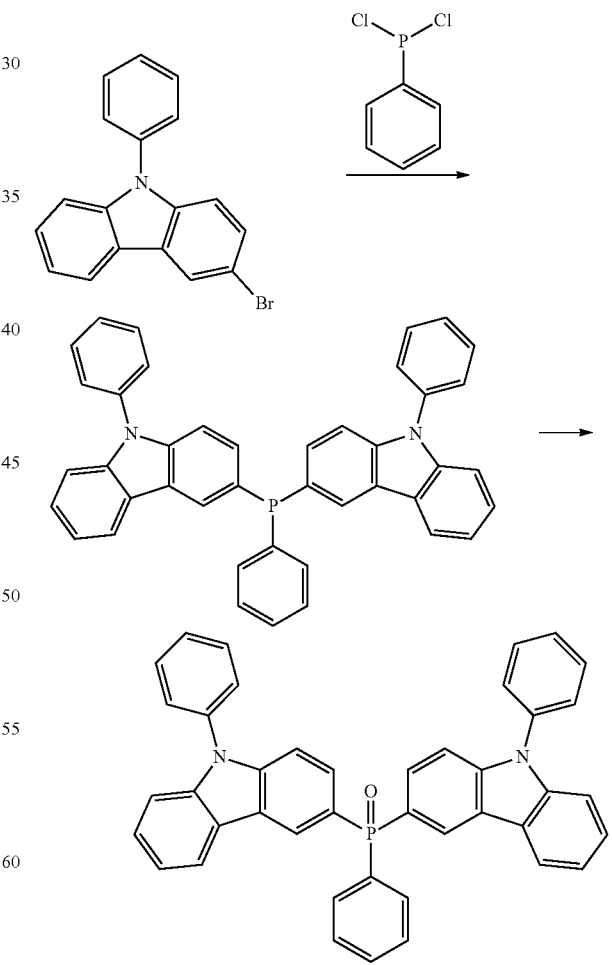

30 mL of tetrahydrofuran was added to 2 g of 3-bromo-9-phenyl carbazole, and the temperature was adjusted to −78°

C. Subsequently, 1.6 mL of butyllithium was slowly added dropwise. While maintaining the temperature, the mixture was stirred for 2 hours, and 3.0 mL of dichlorophenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 3,3'-(phenylphosphonyl)bis(9-phenyl-9-carbazole) as white phosphine oxide corresponding to Compound 3 having the structure of the represented chemical formula.

Nuclear magnetic resonance analysis and mass analysis were performed, and the analytical results were as follows.

1H NMR-1H (200 MHz, CDCl$_3$): δ 8.59-8.53 (d, 2H), 8.12-8.08 (m, 4H), 7.89-7.80 (d, 2H), 7.62-7.42 (m, 15H), 7.35-7.31 (m, 4H). MS (FAB) m/z 608.67 [(M+1)$^+$].

Preparation Example 15

Synthesis of Compound 9

30 mL of tetrahydrofuran was added to 2.57 g of 3-bromo-9-phenyl-6-(triphenylsilyl)-9-carbazole, and the temperature was adjusted to −78° C. Subsequently, 0.57 mL of butyllithium was slowly added dropwise. While maintaining the temperature, the mixture was stirred for 2 hours, and 1.06 mL of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 3-(diphenylphosphonyl)-9-phenyl-6-(triphenylsilyl)-9-carbazole (PPO23) having the structure of Compound 9 as white phosphine oxide. The glass transition temperature was 97.5° C.

Nuclear magnetic resonance analysis and mass analysis were performed, and the analytical results were as follows.

NMR-1H (200 MHz, CDCl$_3$): δ 8.59-8.32 (d, 3H), 7.73-7.67 (m, 5H), 7.63-7.58 (m, 8H), 7.56-7.40 (m, 13H), 7.36-7.33 (m, 7H). MS (FAB) m/z 701.86 [(M+1)$^+$].

Preparation Example 16

Synthesis of Compound 28

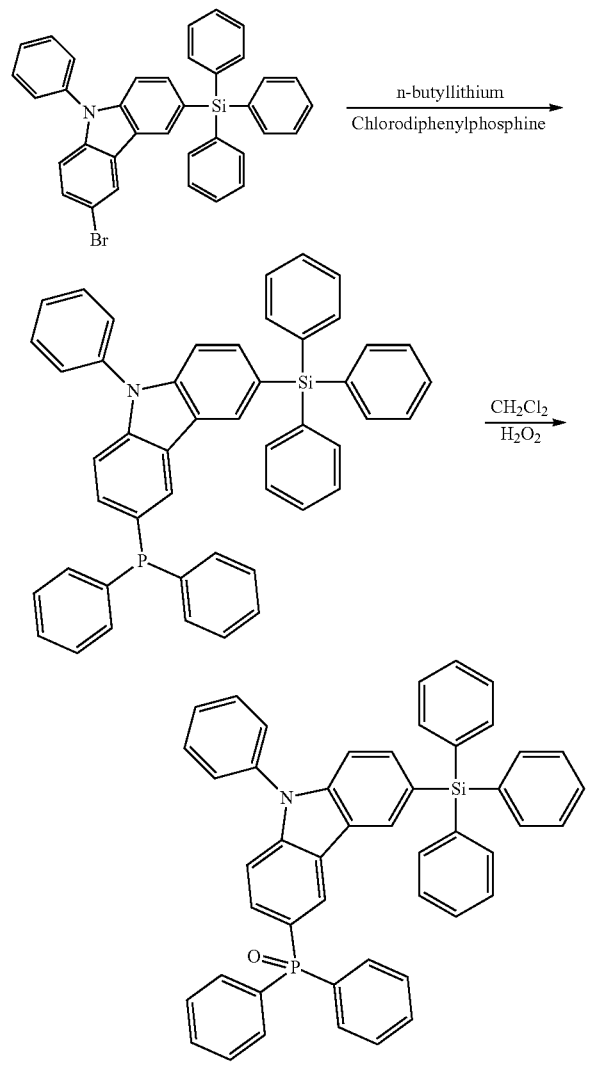

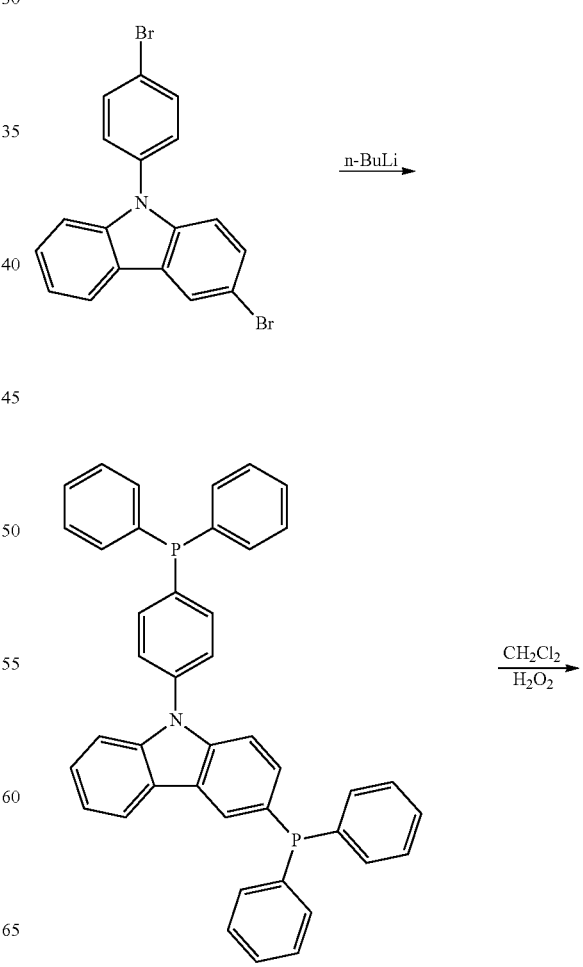

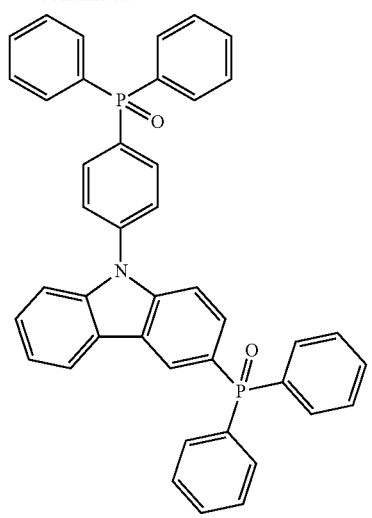

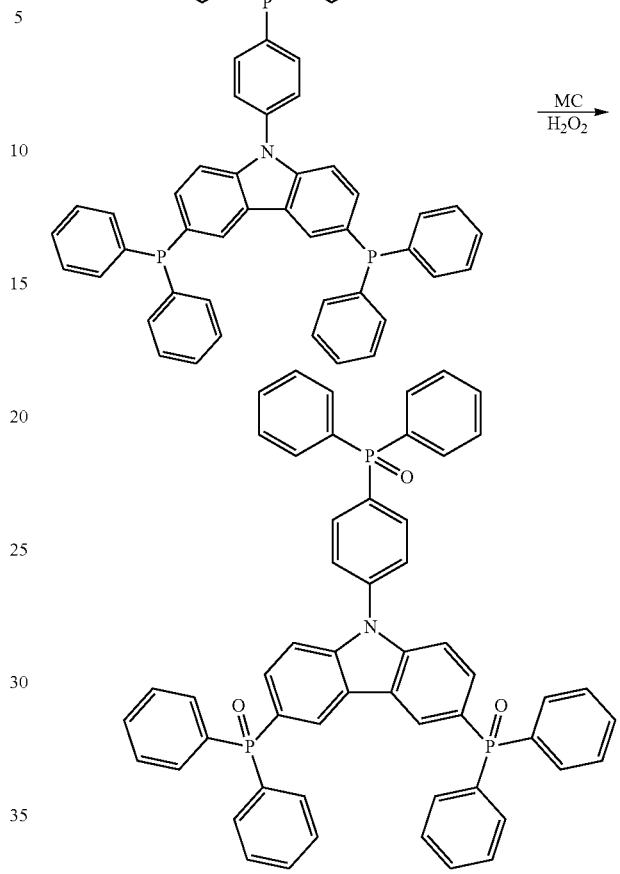

30 mL of tetrahydrofuran was added to 2.5 g of 3-bromo-9-(4-bromophenyl)carbazole, and the temperature was adjusted to −78° C. Subsequently, 1.44 mL of butyllithium was slowly added dropwise.

While maintaining the temperature, the mixture was stirred for 2 hours, and 2.66 mL of chlorodiphenylphosphine was slowly added dropwise, after which the temperature of the mixture was raised to room temperature. After completion of the reaction, methanol was added, and the reaction mixture was stirred and extracted, after which the solvent was dried. To the resulting solid was added dichloromethane, and while the mixture was being stirred, a small amount of hydrogen peroxide was added, yielding 3-(diphenylphosphonyl)-9-(4-diphenylphosphonyl)phenylcarbazole (PPO21) having the structure of Compound 28 as white phosphine oxide. The glass transition temperature was 111° C.

Nuclear magnetic resonance analysis and mass analysis were performed, and the analytical results were as follows.

NMR-1H (200 MHz, CDCl$_3$): δ 8.59-8.53 (d, 1H), 8.11-7.97 (d, 3H), 7.93-7.71 (m, 10H), 7.67 (m, 3H), 7.60-7.45, (m, 12H), 7.36-7.26 (m, 2H). MS (FAB) m/z 643 [(M+1)$^+$].

Preparation Example 17

Synthesis of Compound 30

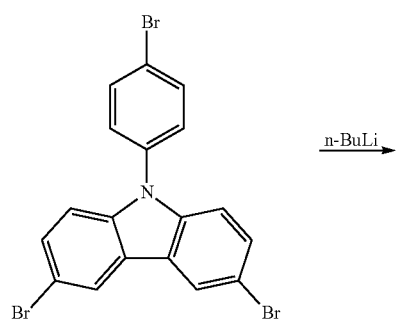

30 mL of tetrahydrofuran was added to 2 g of 3,6-dibromo-9-(4-bromophenyl)carbazole, and the temperature was adjusted to −78° C. Subsequently, 2.5 mL of butyllithium was slowly added dropwise. While maintaining the temperature, the mixture was stirred for 2 hours, and 5.06 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 3,6-bis(diphenylphosphonyl)-9-(4-diphenylphosphonyl)-9-carbazole (PPO3) having the above structure as white phosphine oxide.

Nuclear magnetic resonance analysis and mass analysis were performed, and the analytical results were as follows.

NMR-1H (200 MHz, CDCl$_3$): δ 7.98-7.94 (d, 3H), 7.77-7.64 (m, 14H), 7.63-7.54 (m, 3H), 7.52-7.45 (m, 20H). MS (FAB) m/z 843.8 [(M+1)$^+$].

Preparation Example 18

Synthesis of Compound 31

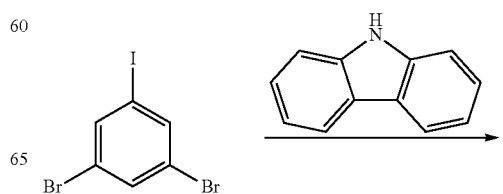

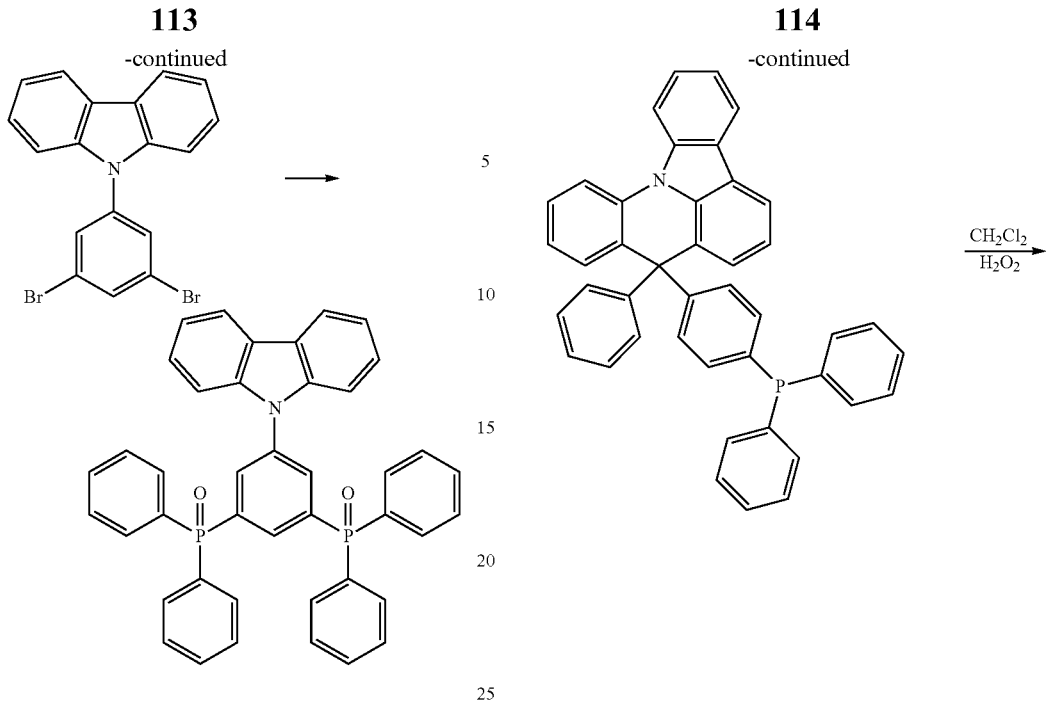

30 mL of tetrahydrofuran was added to 2 g of 9-(3,5-dibromophenyl)-9-carbazole, and the temperature was adjusted to −78° C. Subsequently, 1.14 mL of butyllithium was slowly added dropwise. While maintaining the temperature, the mixture was stirred for 2 hours, and 2.32 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 9-(3,5-bis(diphenylphosphonyl)phenyl-9-carbazole having the above structure as white phosphine oxide.

Nuclear magnetic resonance analysis and mass analysis were performed, and the analytical results were as follows.

NMR-1H (200 MHz, CDCl$_3$): δ 8.55-8.52 (d, 1H), 8.12-8.10 (d, 1H), 7.94-7.95 (d, 1H), 7.80-7.75 (m, 8H), 7.63-7.42 (m, 20H). MS (FAB) m/z 643.65 [(M+1)$^+$].

Preparation Example 19

Synthesis of Compound 103

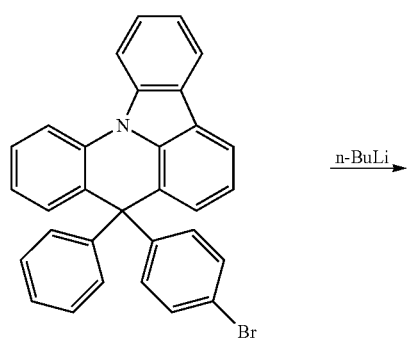

mL of tetrahydrofuran was added to 1 g of 8-(4-bromophenyl-8-phenyl-8H-indolo[3,2,1]acridine, and the temperature was adjusted to −78° C. Subsequently, 1.069 mL of butyllithium was slowly added dropwise. While maintaining the temperature, the mixture was stirred for 2 hours, and 0.589 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 8-(4-diphenylphosphonyl)phenyl)-8H-indolo[3,2,1]acridine having the above structure as white phosphine oxide.

Nuclear magnetic resonance analysis and mass analysis were performed, and the analytical results were as follows.

NMR-1H (200 MHz, CDCl$_3$): δ 8.48-8.46 (d, 1H), 8.21-8.18 (d, 1H), 7.98-7.93 (m, 4H), 7.77-7.65 (m, 3H), 7.55-7.23 (m, 20H), 7.13-7.10 (d, 1H).

MS (FAB) m/z 607.68 [(M+1)$^+$].

Preparation Example 20

Synthesis of Compound 132

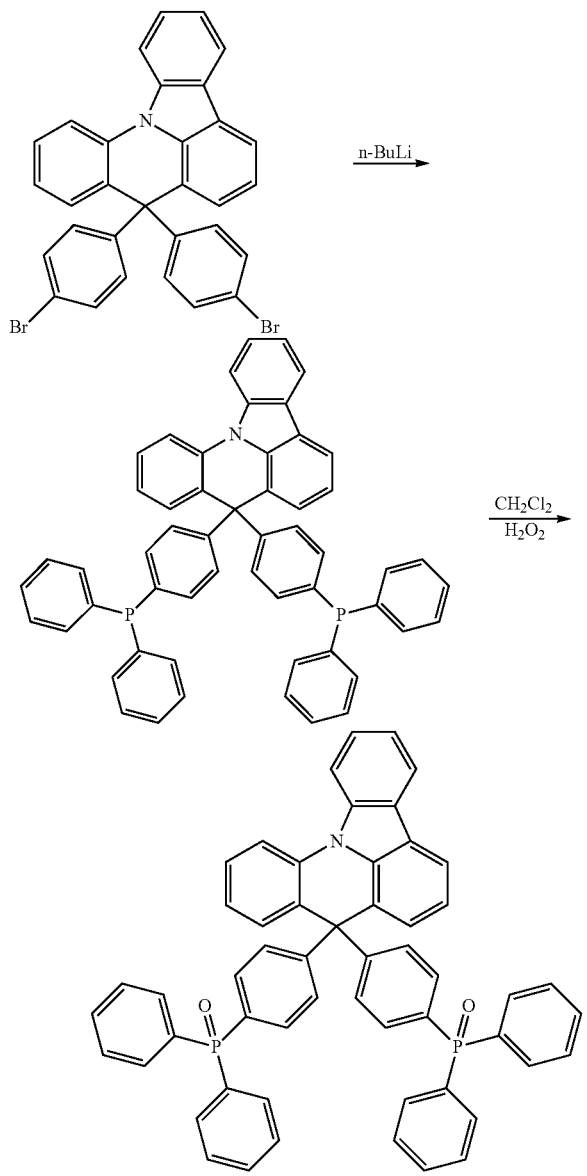

30 mL of tetrahydrofuran was added to 1 g of 8,8-bis(4-bromophenyl)-8H-indolo[3,2,1]acridine, and the temperature was adjusted to −78° C. Subsequently, 1.627 mL of butyllithium was slowly added dropwise. While maintaining the temperature, the mixture was stirred for 2 hours, and 0.895 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 8,8-bis(4-diphenylphosphonyl)phenyl)-8H-indolo[3,2,1]acridine having the above structure as white phosphine oxide.

Nuclear magnetic resonance analysis and mass analysis were performed, and the analytical results were as follows.
NMR-1H (200 MHz, CDCl$_3$): δ 8.48-8.46 (d, 1H), 8.21-8.18 (d, 1H), 7.98-7.93 (m, 13H), 7.55-7.10 (m, 23H), 7.13-7.10 (d, 1H). MS (FAB) m/z 807.85 [(M+1)$^+$].

Example 1

In Preparation Example 12 according to the present invention, a diphenylphosphine oxide compound (Compound 1) having a carbazole structure was synthesized as a compound having a carbazole structure and a phosphine oxide structure.

Compound 1 exhibited a triplet energy of 3.02 eV, a HOMO energy level of 6.16 eV, and a LUMO energy level of 2.6 eV. In order to apply the present compound as a host, a blue phosphorescent device was formed using FCNIr that is a blue dopant. By use of Compound 1 in Table 1, an organic EL device was manufactured. The structure of the device was ITO/DNTPD(60 nm)/NPD(20 nm)/mCP(10 nm)/Compound 1:FCNIr(30 nm, 15%)/Bphen(20 nm)/LiF/Al.

The device was manufactured in the following manner. Specifically, an ITO substrate was washed using ultrasound for 30 min in pure water and isopropyl alcohol, and the surface of the ITO substrate was treated using short-wavelength UV light, after which an organic material was vapor-deposited thereon at a pressure of 1×10$^{-6}$ torr. DNTPD, NPD, mCP, and Bphen were vapor-deposited at a rate of 0.1 nm/s, thus forming respective films having the corresponding thicknesses, and Compound 1 was vapor-deposited together with a FCNIr dopant. As such, Compound 1 was vapor-deposited at a rate of 0.1 nm/s, and FCNIr was vapor-deposited at a rate of 0.015 nm/s. LiF was formed to a thickness of 1 nm at a rate of 0.01 nm/s, and Al was formed to a thickness of 100 nm at a deposition rate of 0.5 nm/s. The device thus obtained was sealed using a CaO desiccant and a cover glass.

Figure 2:
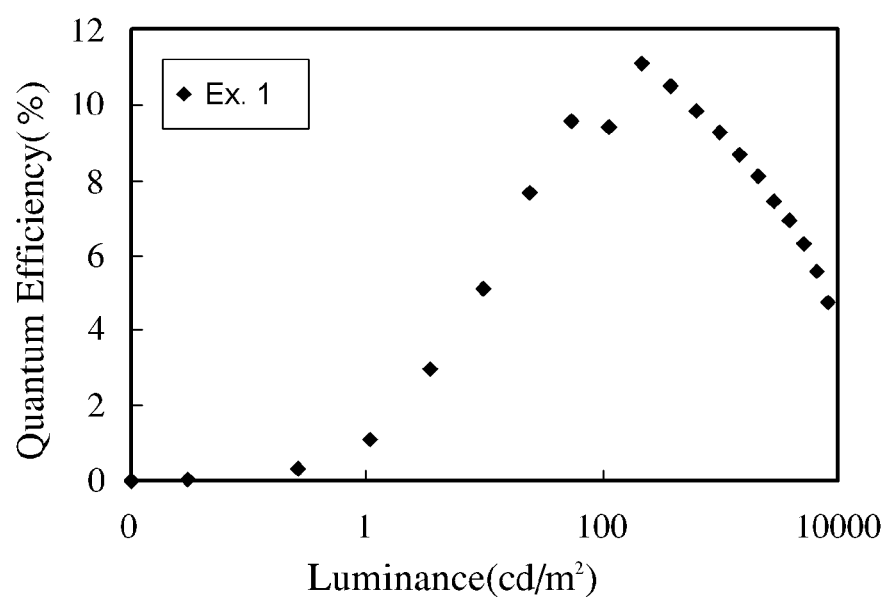
FIG. 2 is a graph showing the efficiency characteristics of the organic electroluminescent device of Example 1 according to the present invention.

The quantum efficiency and the color coordinates of the blue organic EL device thus manufactured are shown in Table 23. The quantum efficiency of Examples 1 to 9 and Comparative Examples 1 and 2 was measured in accordance with the description of literature by Forrest (G. Gu and S. R. Forrest, IEEE Journal of Selected Topics in Quantum Electronics, Vol. 4, No. 1, January/February 1998, p. 83-99). The blue organic EL device manufactured in the present invention manifested a maximum quantum efficiency of 11.1%. The quantum efficiency is graphed in FIG. 2. The color coordinates were (0.14, 0.15).

Example 2

A blue phosphorescent device including Compound 2 synthesized in the present invention was formed using FCNIr which is a known blue dopant. The present compound exhibited a triplet energy of 3.03 eV, a HOMO energy level of 6.31 eV, and a LUMO energy level of 2.77 eV. The structure of the device was ITO/DNTPD(60 nm)/NPD(20 nm)/mCP(10 nm)/Compound 2:FCNIr(30 nm, 15%)/Bphen(20 nm)/LiF/Al. The device was manufactured in the same manner as in Example 1, with the exception that Compound 2 was used in lieu of Compound 1.

Figure 3:
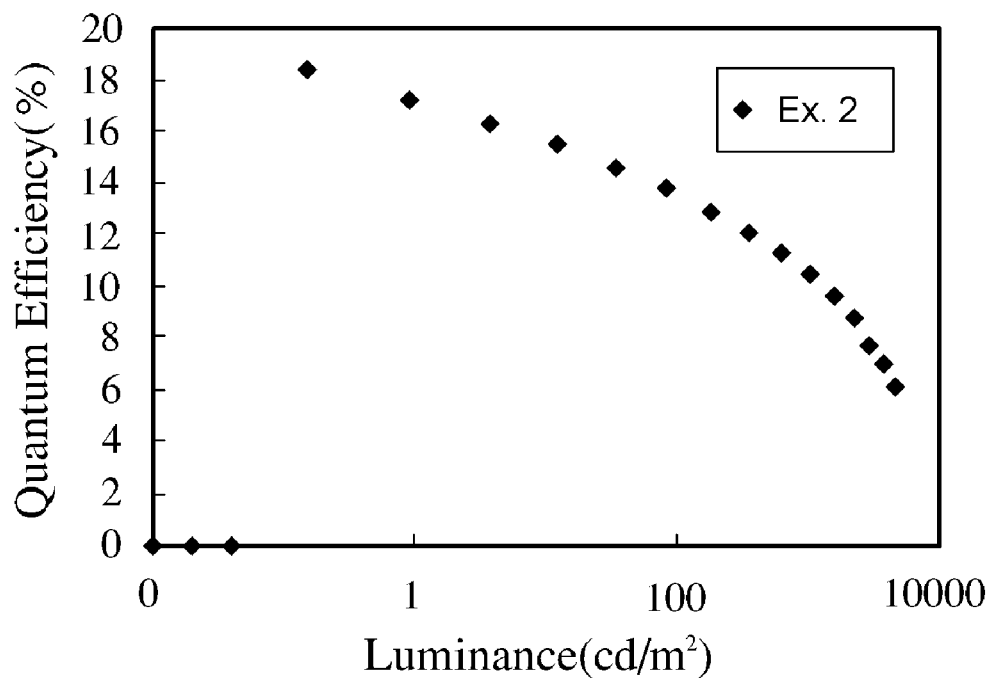
FIG. 3 is a graph showing the efficiency characteristics of the organic electroluminescent device of Example 2 according to the present invention.

The blue organic EL device manufactured in the present invention manifested a maximum quantum efficiency of 18.4%. The quantum efficiency is graphed in FIG. 3. The color coordinates were (0.14, 0.15).

Example 3

A blue phosphorescent device including Compound 3 synthesized in the present invention was formed using FCNIr which is a known blue dopant. The present compound exhibited a triplet energy of 3.0 eV, a HOMO energy level of 5.92 eV, and a LUMO energy level of 2.4 eV. The structure of the device was ITO/DNTPD(60 nm)/NPD(20 nm)/mCP(10 nm)/Compound 3:FCNIr(30 nm, 15%)/Bphen(20 nm)/LiF/Al. The device was manufactured in the same manner as in Example 1, with the exception that Compound 3 was used in lieu of Compound 1.

Figure 4:
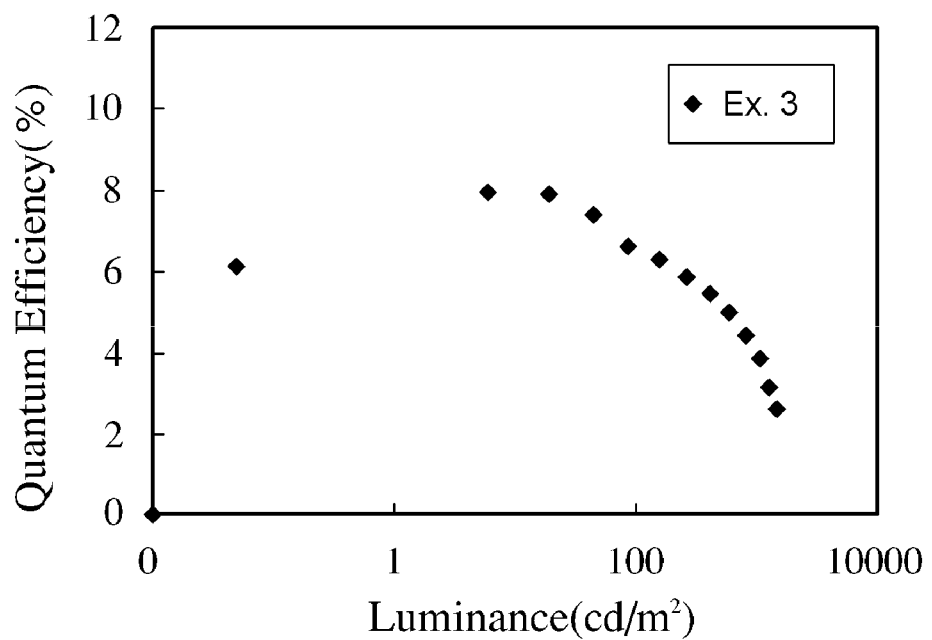
FIG. 4 is a graph showing the efficiency characteristics of the organic electroluminescent device of Example 3 according to the present invention.

The blue organic EL device manufactured in the present invention manifested a maximum quantum efficiency of 7.95%. The quantum efficiency is graphed in FIG. 4. The color coordinates were (0.14, 0.17).

Example 4

A blue phosphorescent device including Compound 9 synthesized in the present invention was formed using FCNIr which is a known blue dopant. The present compound exhibited a triplet energy of 3.02 eV, a HOMO energy level of 5.92 eV, and a LUMO energy level of 2.4 eV. The structure of the device was ITO/DNTPD(60 nm)/NPD(20 nm)/mCP(10 nm)/Compound 9:FCNIr(30 nm, 15%)/Bphen(20 nm)/LiF/Al. The device was manufactured in the same manner as in Example 1, with the exception that Compound 9 was used in lieu of Compound 1.

Figure 5:
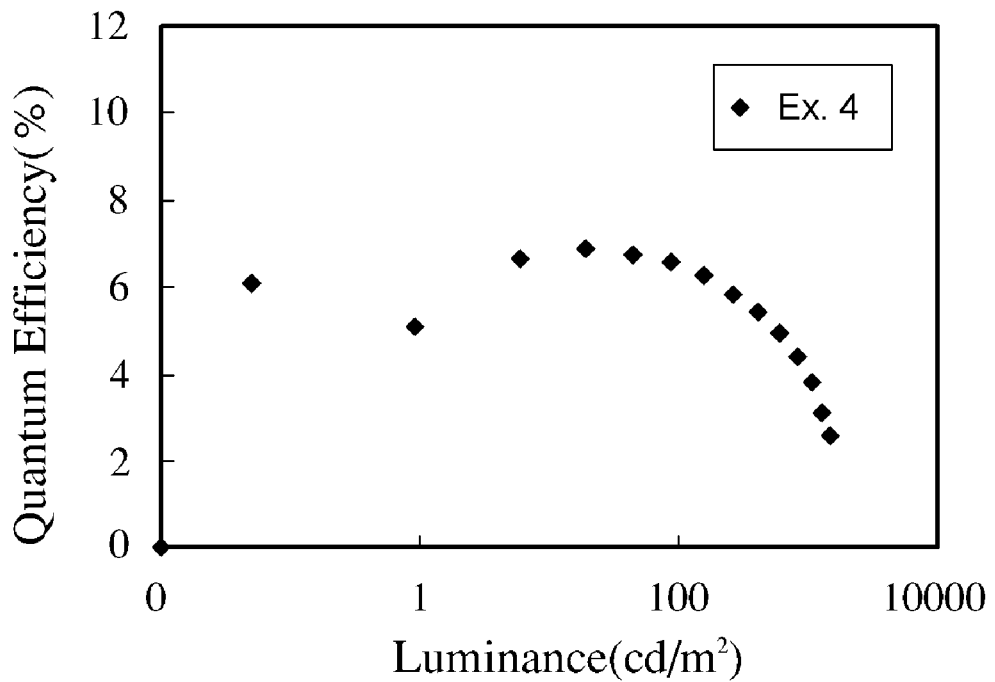
FIG. 5 is a graph showing the efficiency characteristics of the organic electroluminescent device of Example 4 according to the present invention.

The blue organic EL device manufactured in the present invention manifested a maximum quantum efficiency of 6.91%. The quantum efficiency is graphed in FIG. 5. The color coordinates were (0.14, 0.17).

Example 5

A blue phosphorescent device including Compound 28 (PPO21) synthesized in the present invention was formed using FCNIr which is a known blue dopant. The present compound exhibited a triplet energy of 3.01 eV, a HOMO energy level of 6.18 eV, and a LUMO energy level of 2.61 eV. The structure of the device was ITO/DNTPD(60 nm)/NPD (20 nm)/mCP(10 nm)/Compound 28:FCNIr(30 nm, 15%)/Bphen(20 nm)/LiF/Al. The device was manufactured in the same manner as in Example 1, with the exception that Compound 28 was used in lieu of Compound 1.

Figure 6:
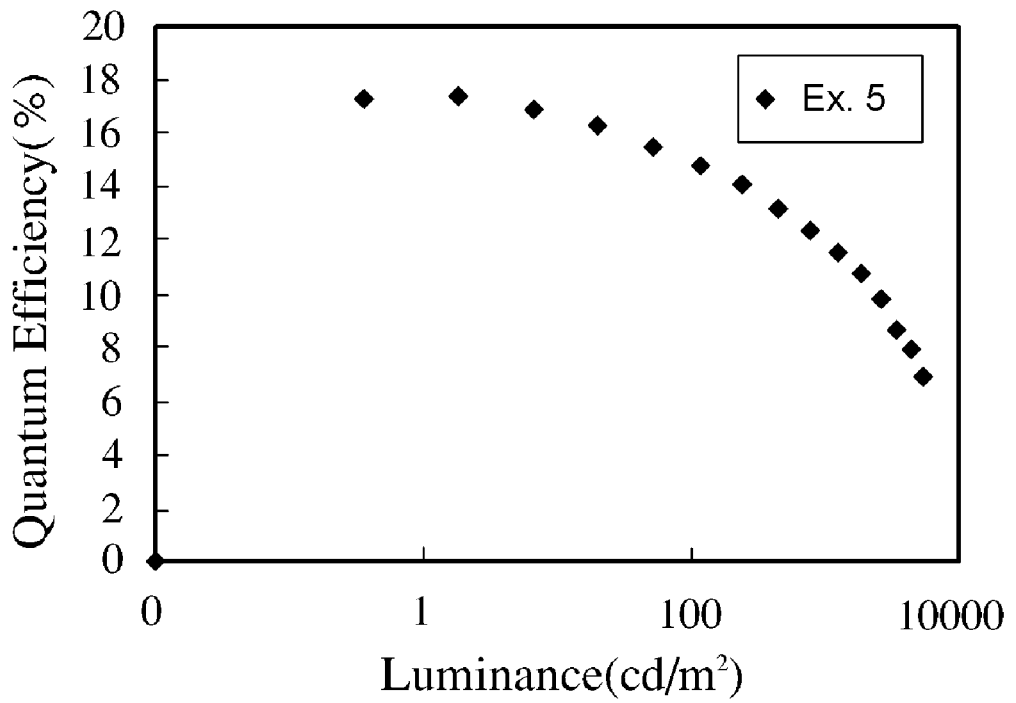
FIG. 6 is a graph showing the efficiency characteristics of the organic electroluminescent device of Example 5 according to the present invention.

The blue organic EL device manufactured in the present invention manifested a maximum quantum efficiency of 17.4%. The quantum efficiency is graphed in FIG. 6. The color coordinates were (0.14, 0.15).

Example 6

A blue phosphorescent device including Compound 30 (PPO3) synthesized in the present invention was formed using FCNIr which is a known blue dopant. The present compound exhibited a triplet energy of 3.03 eV, a HOMO energy level of 6.23 eV, and a LUMO energy level of 2.65 eV. The structure of the device was ITO/DNTPD(60 nm)/NPD (20 nm)/mCP(10 nm)/Compound 30:FCNIr(30 nm, 15%)/Bphen(20 nm)/LiF/Al. The device was manufactured in the same manner as in Example 1, with the exception that Compound 30 was used in lieu of Compound 1.

Figure 7:
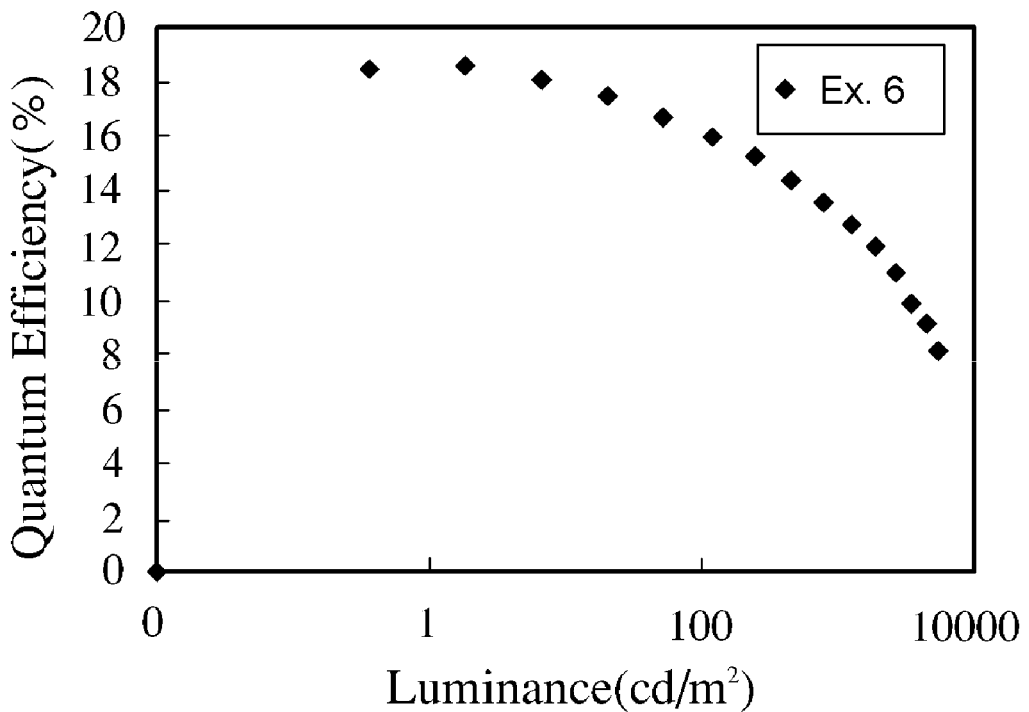
FIG. 7 is a graph showing the efficiency characteristics of the organic electroluminescent device of Example 6 according to the present invention.

The blue organic EL device manufactured in the present invention manifested a maximum quantum efficiency of 18.6%. The quantum efficiency is graphed in FIG. 7. The color coordinates were (0.15, 0.15).

Example 7

A blue phosphorescent device including Compound 31 (PPO4) synthesized in the present invention was formed using FCNIr which is a known blue dopant. The present compound exhibited a triplet energy of 3.01 eV, a HOMO energy level of 6.22 eV, and a LUMO energy level of 2.59 eV. The structure of the device was ITO/DNTPD(60 nm)/NPD (20 nm)/mCP(10 nm)/Compound 31:FCNIr(30 nm, 15%)/Bphen(20 nm)/LiF/Al. The device was manufactured in the same manner as in Example 1, with the exception that Compound 31 was used in lieu of Compound 1.

Figure 8:
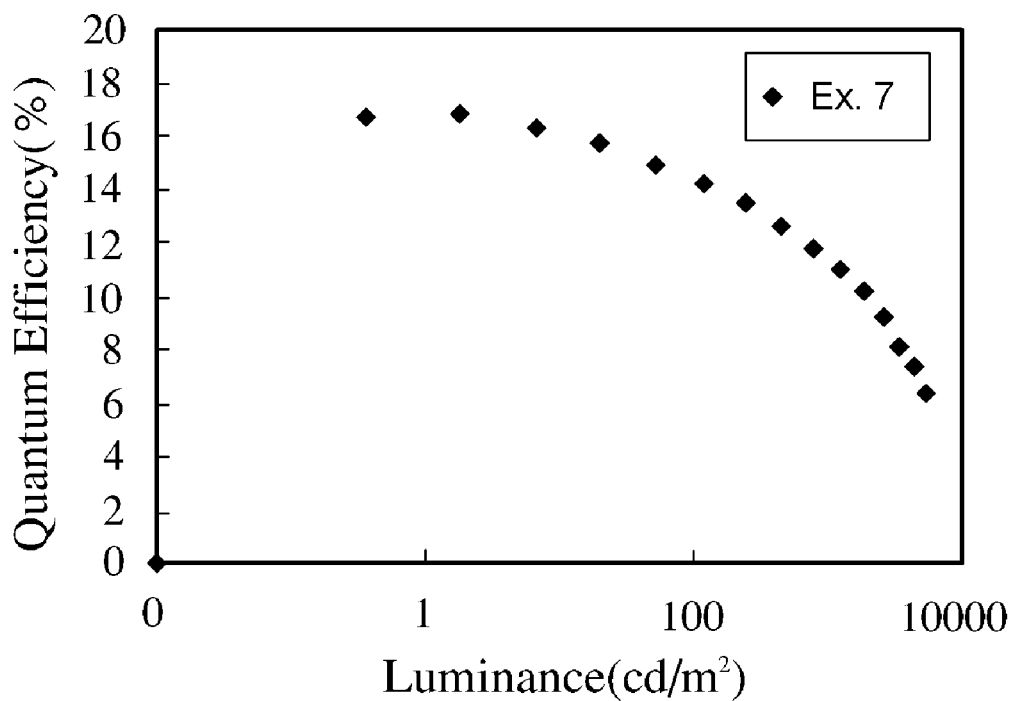
FIG. 8 is a graph showing the efficiency characteristics of the organic electroluminescent device of Example 7 according to the present invention.

The blue organic EL device manufactured in the present invention manifested a maximum quantum efficiency of 16.8%. The quantum efficiency is graphed in FIG. 8. The color coordinates were (0.14, 0.15).

Example 8

A blue phosphorescent device including Compound 103 synthesized in the present invention was formed using FCNIr which is a known blue dopant. The present compound exhibited a triplet energy of 2.96 eV, a HOMO energy level of 6.03 eV, and a LUMO energy level of 2.59 eV. The structure of the device was ITO/DNTPD(60 nm)/NPD(20 nm)/mCP(10 nm)/Compound 103:FCNIr(30 nm,15%)/Bphen(20 nm)/LiF/Al. The device was manufactured in the same manner as in Example 1, with the exception that Compound 103 was used in lieu of Compound 1.

Figure 9:
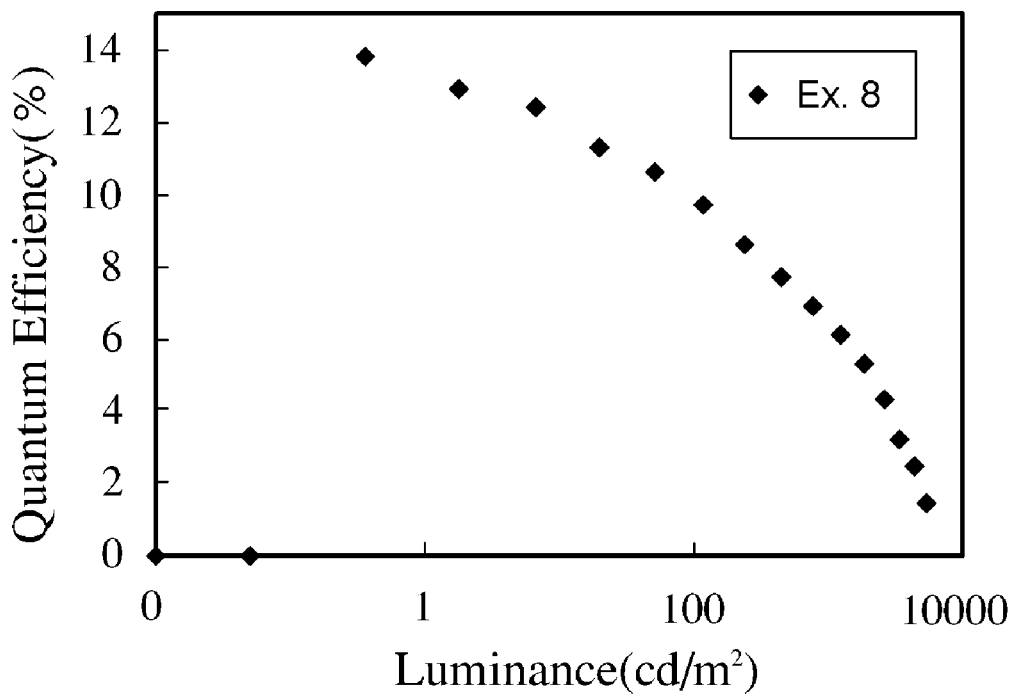
FIG. 9 is a graph showing the efficiency characteristics of the organic electroluminescent device of Example 8 according to the present invention.

The blue organic EL device manufactured in the present invention manifested a maximum quantum efficiency of 14.5%. The quantum efficiency is graphed in FIG. 9. The color coordinates were (0.15, 0.17).

Example 9

A blue phosphorescent device including Compound 132 synthesized in the present invention was formed using FCNIr which is a known blue dopant. The present compound exhibited a triplet energy of 2.97 eV, a HOMO energy level of 6.01 eV, and a LUMO energy level of 2.63 eV. The structure of the device was ITO/DNTPD(60 nm)/NPD(20 nm)/mCP(10 nm)/Compound 132:FCNIr (30 nm, 15%)/Bphen(20 nm)/LiF/Al. The device was manufactured in the same manner as in Example 1, with the exception that Compound 132 was used in lieu of Compound 1.

Figure 10:
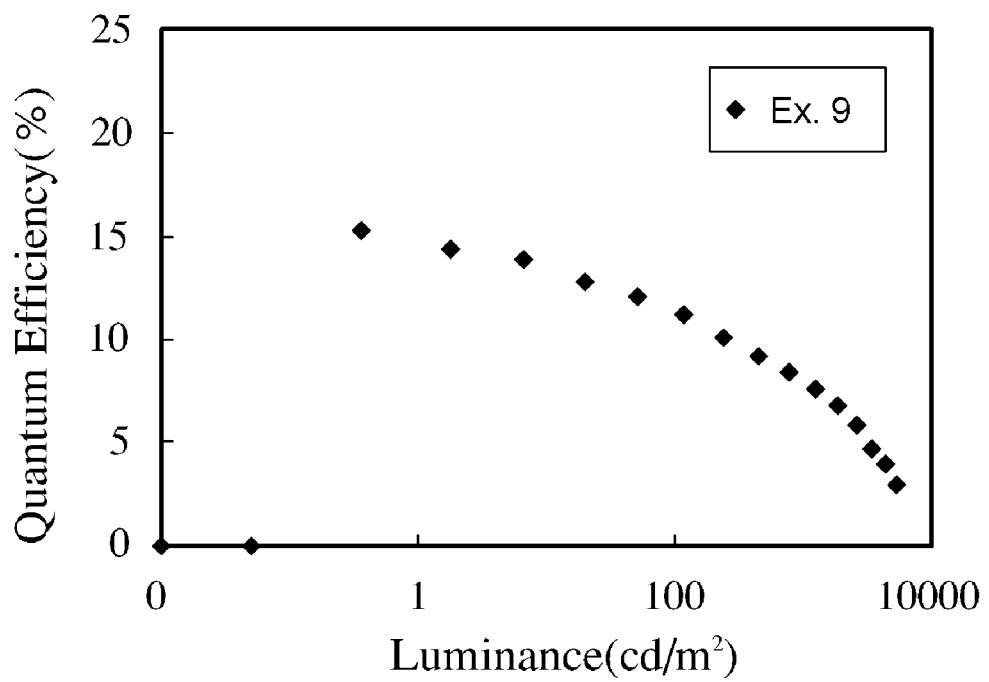
FIG. 10 is a graph showing the efficiency characteristics of the organic electroluminescent device of Example 9 according to the present invention.

The blue organic EL device manufactured in the present invention manifested a maximum quantum efficiency of 15.2%. The quantum efficiency is graphed in FIG. 10. The color coordinates were (0.15, 0.16).

Comparative Example 1

A typically known device having the structure of ITO/DNTPD(60 nm)/NPD(20 nm)/mCP(10 nm)/mCP:FCNIr(30 nm, 15%)/BCP(5 nm)/Alq3(20 nm)/LiF/Al was manufactured. The device was manufactured in the same manner as in Example 1, with the exception that a blue phosphorescent material mCP was used instead of Compound 1 as the host material for a light-emitting layer, and BCP/Alq3 was used instead of Bphen as the material for the electron transport layer.

Figure 11:
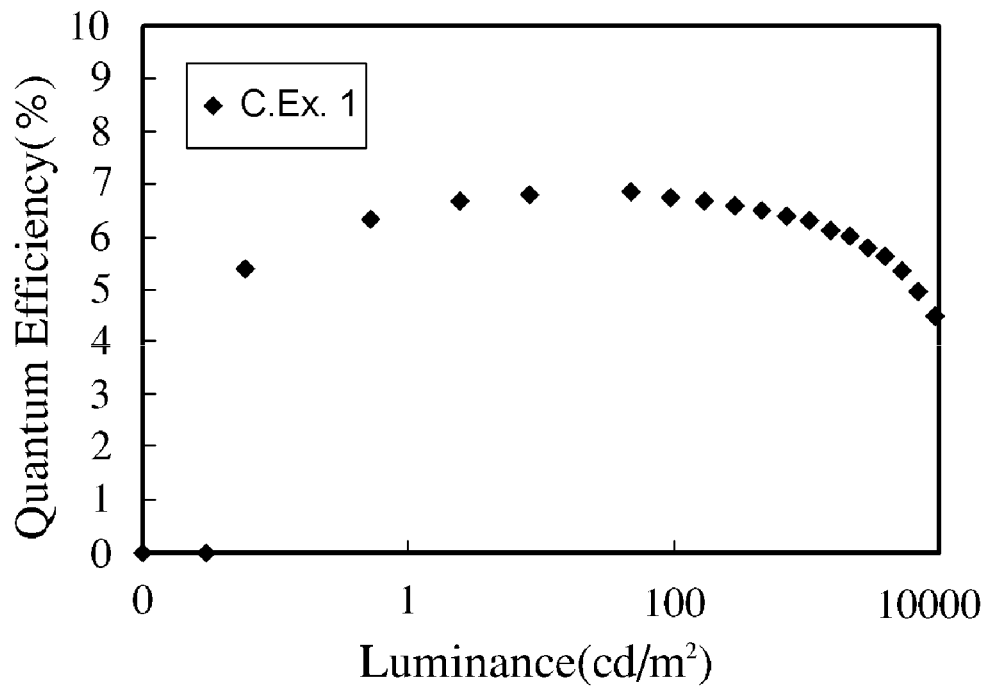
FIG. 11 is a graph showing the efficiency characteristics of the organic electroluminescent device of Comparative Example 1 according to the present invention.

This blue phosphorescent device manifested a low quantum efficiency of 6.87%. The quantum efficiency is graphed in FIG. 11. The color coordinates were (0.15, 0.22).

Comparative Example 2

A typically known device having the structure of ITO/DNTPD(60 nm)/NPD(20 nM)/mCP(10 nM)/mCP:FCNIr(30 nm, 15%)/Bphen(20 nm)/LiF/Al was manufactured. The device was manufactured in the same manner as in Example 1, with the exception that mCP was used instead of Compound 1.

Figure 12:
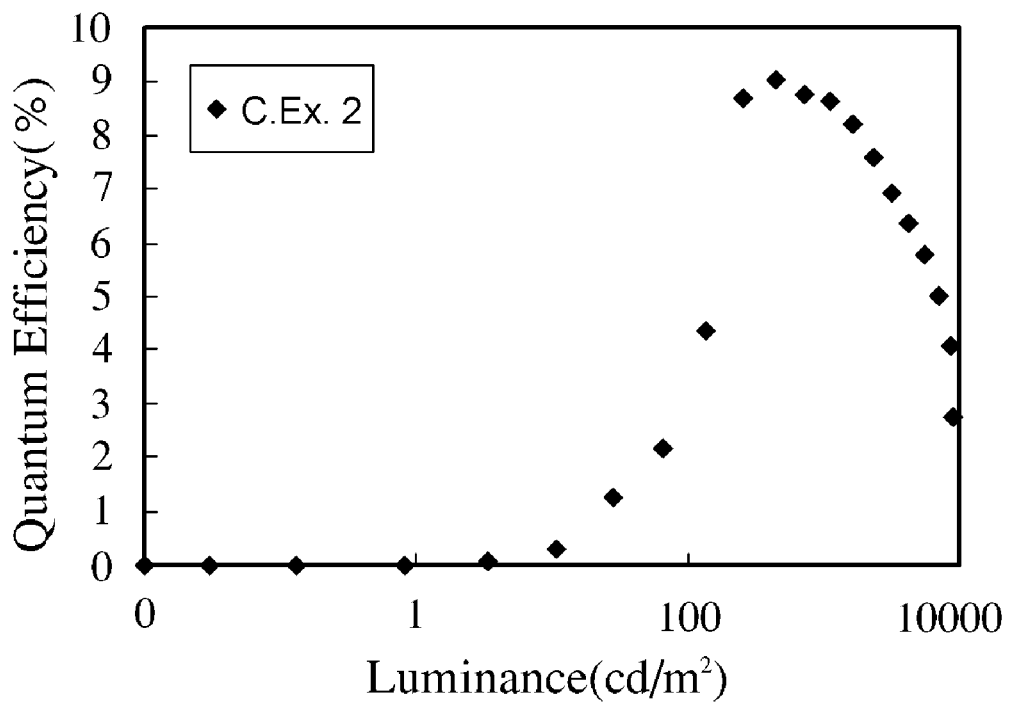
FIG. 12 is a graph showing the efficiency characteristics of the organic electroluminescent device of Comparative Example 2 according to the present invention.

This blue phosphorescent device manifested a low quantum efficiency of 9.06%. The quantum efficiency is graphed in FIG. 12. The color coordinates were (0.14, 0.16).

TABLE 23

Comparison of Device Characteristics of Comparative Examples and Examples

| | Quantum Efficiency (%) | Color Coordinates |
|---|---|---|
| Ex. 1 | 11.1 | (0.14, 0.15) |
| Ex. 2 | 18.4 | (0.14, 0.15) |
| Ex. 3 | 7.95 | (0.14, 0.17) |
| Ex. 4 | 6.91 | (0.14, 0.17) |
| Ex. 5 | 17.4 | (0.14, 0.15) |
| Ex. 6 | 18.6 | (0.15, 0.15) |
| Ex. 7 | 16.8 | (0.14, 0.15) |
| Ex. 8 | 14.5 | (0.15, 0.17) |
| Ex. 9 | 15.2 | (0.15, 0.16) |
| C. Ex. 1 | 6.87 | (0.15, 0.22) |
| C. Ex. 2 | 9.06 | (0.14, 0.16) |

INDUSTRIAL APPLICABILITY

As described above, the present invention adopts a carbazole-based phosphine oxide compound, and thereby an organic EL device can be provided, which solved the problems of thermal instability and the low efficiency of conventional organic EL devices and furthermore achieved superior efficiency characteristics in a pure blue phosphorescent device.

We claim:

1. A compound for an organic electroluminescent device, selected from the group consisting of Chemical Formula 1, 2, 3, 4, 5, 6, 7, and 8, represented by Chemical Formula below:

[Chemical Formula 1]

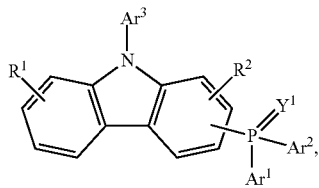

[Chemical Formula 2]

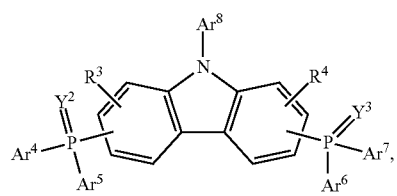

[Chemical Formula 3]

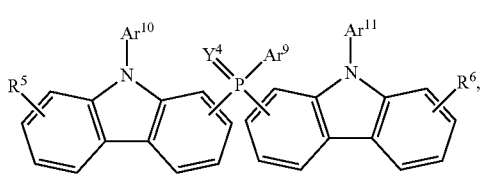

[Chemical Formula 4]

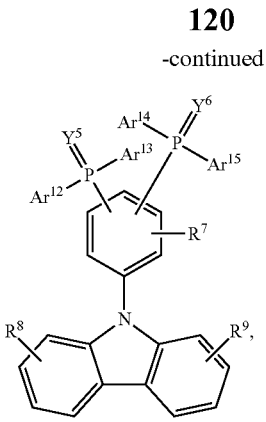

[Chemical Formula 5]

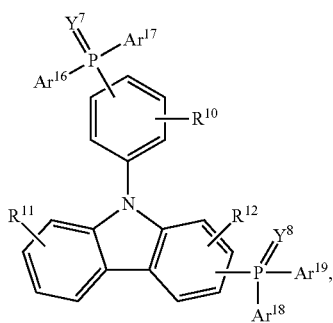

[Chemical Formula 6]

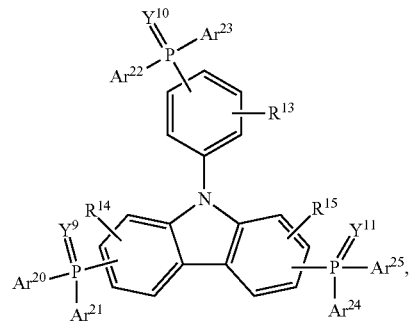

[Chemical Formula 7]

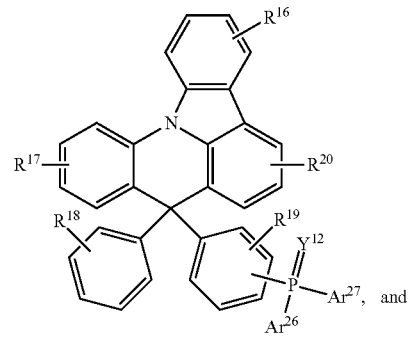

and

-continued

[Chemical Formula 8]

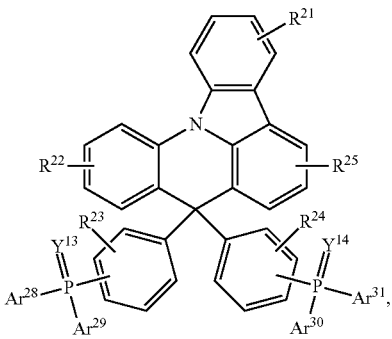

wherein
Y¹ represents an oxygen atom, a sulfur atom or a selenium atom,
Ar¹ and Ar² are identical or different substituents and each represent a substituted or unsubstituted aryl group having 6 to 50 ring carbons, or a substituted or unsubstituted heteroaryl group having 5 to 50 ring atoms,
Ar³ represents a substituted or unsubstituted aryl group having 6 to 50 ring carbons, or a substituted or unsubstituted heteroaryl group having 5 to 50 ring atoms,
when one of R¹ and R² is a hydrogen atom, the other of either R¹ or R² is a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons,
wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group,
or R¹ and R² are identical or different substituents and each represent a halogen atom, a cyano group, a nitro group, as bstituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons,
wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group,
wherein a suitable substituent on the Ar¹, Ar², Ar³, R¹ or R² is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, Y² and Y³ are identical or different substituents and each represent an oxygen atom, a sulfur atom or a selenium atom,
Ar⁴ to Ar⁷ are identical or different substituents and each represent a substituted or unsubstituted aryl group having 6 to 50 ring carbons, or a substituted or unsubstituted heteroaryl group having 5 to 50 ring atoms,
Ar⁸ represents a substituted or unsubstituted aryl group having 6 to 50 ring carbons, or a substituted or unsubstituted heteroaryl group having 5 to 50 ring atoms, and
when one of R³ and R⁴ is a hydrogen atom, the other of either R³ and R⁴ is a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons,
wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group,
or R³ and R⁴ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons,
wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group,
wherein a suitable substituent on the Ar⁴ to Ar⁸, R³ or R⁴ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons,
Y⁴ represents an oxygen atom, a sulfur atom or a selenium atom,
Ar⁹ represents a substituted or unsubstituted aryl group having 6 to 50 ring carbons, or a substituted or unsubstituted heteroaryl group having 5 to 50 ring atoms,
Ar¹⁰ and Ar¹¹ are identical or different substituents and each represent a substituted or unsubstituted aryl group having 6 to 50 ring carbons, or a substituted or unsubstituted heteroaryl group having 5 to 50 ring atoms, and
part or all of R⁵ and R⁶ are independently a hydrogen atom, or R⁵ and R⁶ are identical or different sub stituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^9$ to $Ar^{11}$, $R^5$ or $R^6$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, $Y^5$ and $Y^6$ are identical or different substituents and each represent an oxygen atom, a sulfur atom or a selenium atom, $Ar^{12}$ to $Ar^{15}$ are identical or different substituents and each represent a substituted or unsubstituted aryl group having 6 to 50 ring carbons, or a substituted or unsubstituted heteroaryl group having 5 to 50 ring atoms, and part or all of $R^7$ to $R^9$ are independently a hydrogen atom, or $R^7$ to $R^9$ are identical or different sub substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^{12}$ to $Ar^{15}$ and $R^7$ to $R^9$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, $Y^7$ and $Y^8$ are identical or different substituents and each represent an oxygen atom, a sulfur atom or a selenium atom, $Ar^{16}$ to $Ar^{19}$ are identical or different substituents and each represent a substituted or unsubstituted aryl group having 6 to 50 ring carbons, or a substituted or unsubstituted heteroaryl group having 5 to 50 ring atoms, and part or all of $R^{10}$ to $R^{12}$ are independently a hydrogen atom, or $R^{10}$ to $R^{12}$ are identical or different sub stituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^{16}$ to $Ar^{19}$ and $R^{10}$ to $R^{12}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, $Y^9$ to $Y^{11}$ are identical or different substituents and each represent an oxygen atom, a sulfur atom or a selenium atom, $Ar^{20}$ to $Ar^{25}$ are identical or different substituents and each represent a substituted or unsubstituted aryl group having 6 to 50 ring carbons, or a substituted or unsubstituted heteroaryl group having 5 to 50 ring atoms, and part or all of $R^{13}$ to $R^{15}$ are independently a hydrogen atom, or $R^{13}$ to $R^{15}$ are identical or different sub stituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^{20}$ to $Ar^{25}$ and $R^{13}$ to $R^{15}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, $Y^{12}$ represents an oxygen atom, a sulfur atom or a selenium atom, $Ar^{26}$ and $Ar^{27}$ are identical or different substituents and each represent a substituted or unsubstituted aryl group having 6 to 50 ring carbons, or a substituted or unsubstituted heteroaryl group having 5 to 50 ring atoms, and part or all of $R^{16}$ to $R^{20}$ are independently a hydrogen atom, or $R^{16}$ to $R^{20}$ are identical or different sub stituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^{26}$, $Ar^{27}$ and $R^{16}$ to $R^{20}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, $Y^{12}$ represents an oxygen atom, a sulfur atom or a selenium atom, $Ar^{26}$ and $Ar^{27}$ are identical or different substituents and each represent a substituted or unsubstituted aryl group having 6 to 50 ring carbons, or a substituted or unsubstituted heteroaryl group having 5 to 50 ring atoms, and part or all of $R^{16}$ to $R^{20}$ are independently a hydrogen atom, or $R^{16}$ to $R^{20}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^{26}$, $Ar^{27}$ and $R^{16}$ to $R^{20}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, $Y^{13}$ and $Y^{14}$ are identical or different substituents and each represent an oxygen atom, a sulfur atom or a selenium atom, $Ar^{28}$ to $Ar^{31}$ are identical or different substituents and each represent a substituted or unsubstituted aryl group having 6 to 50 ring carbons, or a substituted or unsubstituted heteroaryl group having 5 to 50 ring atoms, and part or all of $R^{21}$ to $R^{25}$ are independently a hydrogen atom, or $R^{21}$ to $R^{25}$ are identical or different substituents and each represent a halogen atom, a cyano group, a nitro group, a substituted or unsubstituted aryl group having 6 to 50 ring carbons, a substituted or unsubstituted heteroaryl group having 5 to 50 ring atoms, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the substituted or unsubstituted aryl group having 6 to 50 ring carbons, the substituted or unsubstituted heteroaryl group having 5 to 50 ring atoms, or the substituted or unsubstituted cycloalkyl group having 3 to 50 carbons forms a saturated or unsaturated ring independently or with an adjacent group, wherein a suitable substituent on the $Ar^{28}$ to $Al^{31}$ and $R^{21}$ to $R^{25}$ is a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons.

2. The compound of claim 1,
wherein
$Y^1$ represents an oxygen atom, $Ar^1$ and $Ar^2$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $Ar^3$ represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and when one of $R^1$ and $R^2$ is a hydrogen atom, the other of either $R^1$ or $R^2$ is a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, or $R^1$ and $R^2$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^1$ to $Ar^3$, $R^1$ or $R^2$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

3. The compound of claim 1, wherein $Y^1$ represents an oxygen atom, $Ar^1$ and $Ar^2$ each represent a phenyl group, $Ar^3$ represents a phenyl group, and $R^1$ and $R^2$ each represent a phenyl group.

4. The compound of claim 1,
wherein
$Y^2$ and $Y^3$ represent an oxygen atom, $Ar^4$ to $Ar^7$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $Ar^8$ represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and when one of $R^3$ and $R^4$ is a hydrogen atom, the other of either $R^3$ and $R^4$ is a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pryenyl group forms a saturated or unsaturated ring independently or with an adjacent group, or $R^3$ and $R^4$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^4$ to $Ar^8$, $R^3$ or $R^4$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

5. The compound of claim 1,
wherein
$Y^4$ represents an oxygen atom, $Ar^9$ represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $Ar^{10}$ and $Ar^{11}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^5$ and $R^6$ are independently a hydrogen atom, or $R^5$ and $R^6$ are identical or different sub stituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^9$ to $Ar^{11}$, $R^5$ and $R^6$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

6. The compound of claim 1,
wherein
$Y^5$ and $Y^6$ represent an oxygen atom, $Ar^{12}$ to $Ar^{15}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^7$ to $R^9$ are independently a hydrogen atom, or $R^7$ to $R^9$ are identical or different sub stituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^{12}$ to $Ar^{15}$ and $R^7$ to $R^9$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

7. The compound of claim 1,
wherein
$Y^7$ and $Y^8$ each represent an oxygen atom, $Ar^{16}$ to $Ar^{19}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{10}$ to $R^{12}$ are independently a hydrogen atom, or $R^{10}$ to $R^{12}$ are identical or different sub substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^{16}$ to $Ar^{19}$ and $R^{10}$ to $R^{12}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

8. The compound of claim 1,
wherein
$Y^9$ to $Y^{11}$ each represent an oxygen atom,
$Ar^{20}$ to $Ar^{25}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{13}$ to $R^{15}$ are independently a hydrogen atom, or $R^{13}$ to $R^{15}$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^{20}$ to $Ar^{25}$ and $R^{13}$ to $R^{15}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

9. The compound of claim 1,
wherein
$Y^{12}$ represents an oxygen atom,
$Ar^{26}$ and $Ar^{27}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{16}$ to $R^{20}$ are independently a hydrogen atom, or $R^{16}$ to $R^{20}$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^{26}$, $Ar^{27}$ and $R^{16}$ to $R^{20}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

10. The compound of claim 1,
wherein
$Y^{13}$ and $Y^{14}$ each represent an oxygen atom,
$Ar^{28}$ to $Ar^{31}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, and part or all of $R^{21}$ to $R^{25}$ are independently a hydrogen atom, or $R^{21}$ to $R^{25}$ are identical or different substituents and each represent a halogen atom, a cyano group, a nitro group, a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, wherein the substituted or unsubstituted phenyl group having 6 to 34 carbons, the substituted or unsubstituted biphenyl group, the substituted or unsubstituted terphenyl group, the substituted or unsubstituted naphthyl group, the substituted or unsubstituted anthryl group, or the substituted or unsubstituted pyrenyl group forms a saturated or unsaturated ring independently or with an adjacent group, wherein a suitable substituent on the $Ar^{28}$ to $Ar^{31}$ and $R^{21}$ to $R^{25}$ is a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons.

11. An organic electroluminescent device, comprising:
a first electrode;
a second electrode; and
a single organic layer or a plurality of organic layers having at least one light-emitting layer, formed between the first electrode and the second electrode,
wherein the organic layer includes a compound for an organic electroluminescent device selected from the group consisting of Chemical formula 1-8, represented by Chemical Formula below:

[Chemical Formula 1]
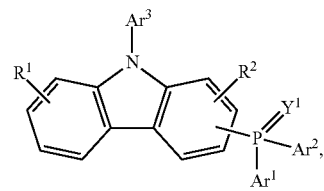

[Chemical Formula 2]
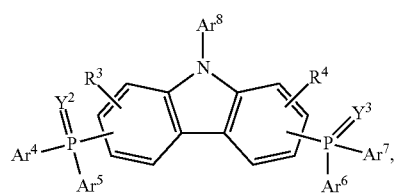

[Chemical Formula 3]
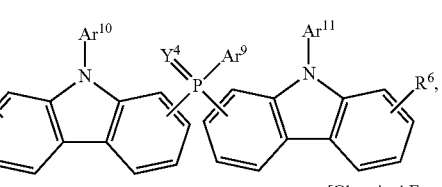

[Chemical Formula 4]
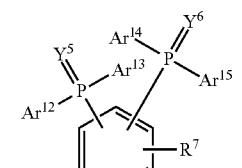

[Chemical Formula 5]
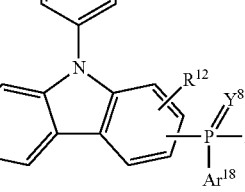

[Chemical Formula 6]
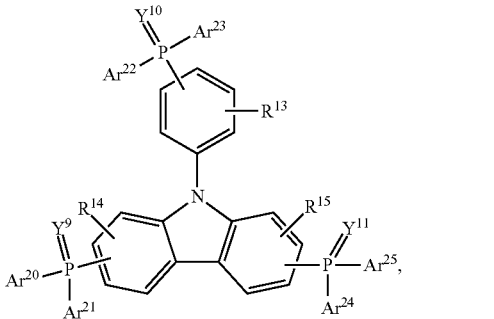

[Chemical Formula 7]
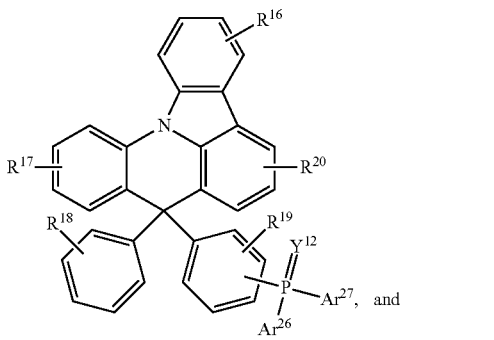

[Chemical Formula 8]
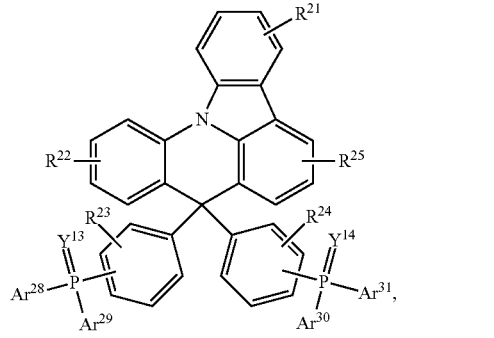

wherein, $Y^{1-14}$, $Ar^{1-31}$, and $R^{1-25}$ are as defined in claim 1.

12. The organic electroluminescent device of claim 11, wherein the light-emitting layer includes the compound for an organic electroluminescent device.

13. The organic electroluminescent device of claim 11, wherein the organic layer further includes a hole transport layer and the compound for an organic electroluminescent device is included in the hole transport layer.

* * * * *